(12) United States Patent
Sottile et al.

(10) Patent No.: US 9,364,516 B2
(45) Date of Patent: Jun. 14, 2016

(54) TREATMENT OF FIBROSIS-RELATED DISORDERS USING FIBRONECTIN BINDING PROTEINS AND POLYPEPTIDES

(75) Inventors: Jane Sottile, Rochester, NY (US); Burns C. Blaxall, Pittsford, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/576,900

(22) PCT Filed: Feb. 3, 2011

(86) PCT No.: PCT/US2011/023634
§ 371 (c)(1),
(2), (4) Date: Mar. 11, 2013

(87) PCT Pub. No.: WO2011/097401
PCT Pub. Date: Aug. 11, 2011

(65) Prior Publication Data
US 2013/0190224 A1    Jul. 25, 2013

Related U.S. Application Data

(60) Provisional application No. 61/301,075, filed on Feb. 3, 2010.

(51) Int. Cl.
*A61K 38/39* (2006.01)
*A61K 38/16* (2006.01)

(52) U.S. Cl.
CPC .................................. *A61K 38/164* (2013.01)

(58) Field of Classification Search
None
See application file for complete search history.

(56) References Cited

U.S. PATENT DOCUMENTS

| | | |
|---|---|---|
| 2002/0026236 A1 | 2/2002 | Helmus et al. |
| 2002/0169108 A1 | 11/2002 | Pilon |
| 2009/0126725 A1 | 5/2009 | Fajardo |

FOREIGN PATENT DOCUMENTS

| | | |
|---|---|---|
| EP | 0397633 A2 | 11/1990 |
| WO | 00/04863 A2 | 2/2000 |
| WO | 2009/126725 A1 | 10/2009 |
| WO | 2011/069090 A1 | 6/2011 |

OTHER PUBLICATIONS

Shi et al., "Collagen I matrix turnover is regulated by fibronectin polymerization," Am. J. Physiol. Cell Physiol. 298:C1265-C1275 (Jan. 27, 2010).*
Shi et al., "Collagen I matrix turnover is regulated by fibronectin polymerization," Am. J. Physiol. Cell Physiol. 298:C1265-C1275 (Jan. 2010).*
Chiang et al., "Fibronectin is an important regulator of flow-induced vascular remodeling," Arterioscler. Thromb. Vasc. Biol. 29:1074-1079 (Apr. 30, 2009).*
UniprotKB/Swiss-Prot Accession No. Q711C4 (accessed Jun. 15, 2014 at URL: uniprot.org/uniprot/Q711C4.*
UniprotKB/Swiss-Prot Accession No. P72416 (accessed Jun. 15, 2014 at URL: uniprot.org/uniprot/P72416).*
UniprotKB/Swiss-Prot Accession No. E9MXY5 (accessed Jun. 15, 2014 at URL: uniprot.org/uniprot/E9MXY5).*
Tomasini-Johansson et al., "A 49-residue peptide from adhesin F1 of *Streptococcus pyogenes* inhibits fibronectin matrix assembly," J. Biol. Chem. 276:23430-23439 (2001).*
Intengan et al., "Vascular Remodeling in Hypertension: Roles of Apoptosis, Inflammation, and Fibrosis," Hypertension 38:581-587 (2001).*
Frohlich, "Fibrosis and Ischemia: The Real Risks in Hypertensive Heart Disease," Amer. J. Hyperten. 14:194S-199S (2001).*
Tsuda et al., "Post-ischemic myocardial fibrosis occurs independent of hemodynamic changes," Cardiovasc. Res. 59: 926-933 (2003).*
Schennings et al., "Immunization with Fibronectin Binding Protein from *Staphylococcus aureus* Protects Against Experimental Endocarditis in Rats," Microb. Pathogen. 15:227-236 (1993).
Chernousov et al., "Monoclonal Antibody to Fibronectin Which Inhibits Extracellular Matrix Assembly," FEBS. Lett. 217(1):124-128 (1987).
Cho et al., "Enhancement of Thrombogenesis by Plasma Fibronectin Cross-Linked to Fibrin and Assembled in Platelet Thrombi," Blood 107:3555-3563 (2006).
Supplemental European Search Report for European Patent Application No. 11740368.3 dated Jun. 3, 2013.
Tomasini-Johansson et al., "A 49-Residue Peptide From Adhesin F1 of *Streptococcus pyogenes* Inhibits Fibronectin Matrix Assembly," J. Biol. Chem. 276(26):23430-23439 (2001).
Shi et al., "Collagen I Matrix Turnover Is Regulated by Fibronectin Polymerization," Am. J. Physiol. Cell Physiol. 298: C1265-C1275 (2010).
Chiang et al., "Fibronectin Is an Important Regulator of Flow-Induced Vascular Remodeling," Arterioscler. Thromb. Vasc. Biol. 29:1074-1079 (2009).
Sottile and Chandler, "Fibronectin Matrix Turnover Occurs Through a Caveolin-1-Dependent Process," Mol. Biol. Cell 16:757-768 (2005).
Sottile et al., "Fibronectin-Dependent Collagen 1 Deposition Modulates the Cell Response to Fibronectin," Am. J. Physiol. Cell Physiol. 293:C1934-C1946 (2007).
Hocking et al., "Stimulation of Integrin-Mediated Cell Contractility by Fibronectin Polymerization," J. Biol. Chem. 275(14):10673-10682 (2000).

(Continued)

*Primary Examiner* — Julie Ha
*Assistant Examiner* — Kristina M Hellman
(74) *Attorney, Agent, or Firm* — LeClairRyan, a Professional Corporation

(57) ABSTRACT

The present invention is directed to various uses of fibronectin binding proteins or polypeptides for treating and preventing fibrosis and fibrosis related conditions. The fibronectin binding proteins and polypeptides are also useful for treating conditions associated with vascular remodeling and cardiac dysfunction.

13 Claims, 18 Drawing Sheets

(56) References Cited

OTHER PUBLICATIONS

Sottile and Hocking, "Fibronectin Polymerization Regulates the Composition and Stability of Extracellular Matrix Fibrils and Cell-Matrix Adhesions," Mol. Biol. Cell 13:3546-3559 (2002).

George et al., "Fibronectins are Essential for Heart and Blood Vessel Morphogenesis but are Dispensable for Initial Specification of Precursor Cells," Blood 90(8):3073-3081 (1997).

Zhou et al., "Fibronectin Fibrillogenesis Regulates Three-Dimensional Neovessel Formation," Genes & Develop. 22:1231-1243 (2008).

International Search Report and Written Opinion for PCT/US11/23634 (Jun. 6, 2011).

Schwarz-Linek et al., "Fibronectin-Binding Proteins of Gram-Positive Cocci," Microbes and Infection 8:2291-2298 (2006).

Weber K., "Extracellular Matrix Remodeling in Heart Failure," Circulation 96:4065-4082 (1997).

Cleutjens et al., "The Infarcted Myocardium: Simply Dead Tissue, or a Lively Target for Therapeutic Interventions," Cardiovascular Research 44:232-241 (1999).

Creemers et al., Deficiency of TIMP-1 Exacerbates LV Remodeling after Myocardial Infarction in Mice, Am. J. Physiol Heart Circ. Physiol. 284: H364-371 (2003).

Yarbrough et al., "Selective Targeting and Timing of Matrix Metalloproteinase Inhibition in Post-Myocardial Infarction Remodeling," Circulation 108: 1753-1759 (2003).

Matsumura et al., "Targeted Deletion or Pharmacological Inhibition of MMP-2 Prevents Cardiac Rupture after Myocardial Infarction in Mice," J. Clin. Invest. 115: 599-609 (2005).

Heymans et al., "Inhibition of Plasminogen Activators or Matrix Metalloproteinases Prevents Cardiac Rupture but Impairs Therapeutic Angiogenesis and Causes Cardiac Failure," Nature Med. 5: 1135-1142 (1999).

Yamada K., "Fibronectin Peptides in Cell Migration and Wound Repair," J. Clin. Invest. 105(11): 1507-09 (2000).

Knowlton et al., "Rapid Expression of Fibronectin in the Rabbit Heart after Myocardial Infarction with and without Reperfusion," J. Clin. Invest. 89:1060-68 (1992).

Ulrich et al., "Increased Expression of Fibronectin Isoforms after Myocardial Infarction in Rats," J. Mol. Cell. Cardiol. 29(9): 2533-2543 (1997).

Willems et al., "Tenascin and Fibronectin Expression in Healing Human Myocardial Scars," J. Pathology 179(3): 321-325 (1996).

Ensenberger et al., "Specific Interactions Between F1 Adhesin of *Streptococcus pyogenes* and N-terminal Modules of Fibronectin," J. Biol. Chem. 276:35606-35613 (2001).

Ozeri et al., "A Two-Domain Mechanism for Group A Streptococcal Adherence Through Protein F to the Extracellular Matrix," Embo J. 15(5):989-998 (1996).

Meenan et al., "The Tandem β-Zipper Model Defines High Affinity Fibronectin-binding Repeats within *Staphylococcus aureus* FnBPA," J. Biol. Chem. 282:25893-25902 (2007).

European Examination Report for corresponding EP Application No. 11740368.3 (Dec. 22, 2014).

Chernousov et al., "Role of the I-9 and III-1 Modules of Fibronectin in Formation of an Extracellular Fibronectin Matrix," J. Biol. Chem. 266(17):10851-10858 (1991).

Dallas et al., "Fibronectin Regulates Latent Transforming Growth Factor-Beta (TGFBeta) by Controlling Matrix Assembly of Latent TGFBeta-Binding Protein-1," J. Biol. Chem. 280(19):18871-18880 (2005).

McKeown-Longo & Mosher, "Interaction of the 70,000-mol-wt Amino-Terminal Fragment of Fibronectin with the Matrix-Assembly Receptor of Fibroblasts," J. Cell Biol. 100:364-374 (1985).

Quade & McDonald, "Fibronectin's Amino-Terminal Matrix Assembly Site is Located Within the 29-kDa Amino-Terminal Domain Containing Five Type I Repeats," J. Biol. Chem. 263(36):19602-19609 (1988).

European Examination Report for corresponding EP Application No. 11740368.3 (May 26, 2014).

Cohn et al., "Cardiac Remodeling-Concepts and Clinical Implications: A Consensus Paper From an International Forum on Cardiac Remodeling," J. Am. Coll. Cardiol. 35(3):569-582 (2000).

Henderson et al., "Fibronectin: A Multidomain Host Adhesin Targeted by Bacterial Fibronectin-Binding Proteins," FEMS Microbiol. Rev. 35:147-200 (2011).

\* cited by examiner

A.

B.

TREATMENT OF FIBROSIS-RELATED DISORDERS USING FIBRONECTIN BINDING PROTEINS AND POLYPEPTIDES

This application claims the benefit of U.S. Provisional Patent Application Ser. No. 61/301,075 filed Feb. 3, 2010, which is hereby incorporated by reference in its entirety.

This invention was made with government support under grant numbers HL070261 and GM069729 awarded by the National Institutes of Health. The government has certain rights in this invention.

FIELD OF THE INVENTION

The present invention is directed to methods of treating and preventing fibrosis and fibrosis-related diseases in a subject.

BACKGROUND OF THE INVENTION

Normal tissue repair processes are critical for maintaining proper tissue function. Tissue fibrosis is characterized by the abnormal accumulation of extracellular matrix ("ECM") that is thought to arise from unresolved tissue repair (Selman et al., "Idiopathic Pulmonary Fibrosis: Prevailing and Evolving Hypotheses About its Pathogenesis and Implications for Therapy," *Ann. Intern. Med.* 134(2):136-151 (2001) and Mutsaers et al., "Mechanisms of Tissue Repair: From Wound Healing to Fibrosis," *Int. J. Biochem. Cell Biol.* 29(1):5-17 (1997)). Fibrosis affects many organ systems, including the lung, kidney, liver and heart; and many disease processes, including cardiomyopathies, hypertension, chronic hepatitis C infection, adult respiratory distress syndrome, and sarcoidosis are accompanied by fibrosis (Pugin et al., "The Alveolar Space is the Site of Intense Inflammatory and Profibrotic Reactions in the Early Phase of Acute Respiratory Distress Syndrome," *Crit. Care Med.* 27(2):304-312 (1999); Bedossa et al., "Liver Extracellular Matrix in Health and Disease," *J. Pathol.* 200(4):504-515 (2003); Heling et al., "Increased Expression of Cytoskeletal, Linkage, and Extracellular Proteins in Failing Human Myocardium," *Circ. Res.* 86(8):846-853 (2000); Intengan et al., "Vascular Remodeling in Hypertension: Roles of Apoptosis, Inflammation, and Fibrosis," *Hypertension.* 38(3 Pt 2):581-587 (2001); and Berk et al., "ECM Remodeling in Hypertensive Heart Disease," *J. Clin. Invest.* 117(3):568-575 (2007)). Current therapies to treat fibrotic conditions, including dermal fibrosis and liver fibrosis, have limited efficacy (Wolfram et al., Hypertrophic Scars and Keloids—A Review of Their Pathophysiology, Risk Factors, and Therapeutic Management," *Dermatol. Surg.* 35(2):171-181 (2009); Butler et al., "Current Progress in Keloid Research and Treatment," *J. Am. Coll. Surg.* 206(4):731-741 (2008); Muriel et al., "Beneficial Drugs for Liver Diseases," *J. Appl. Toxicol.* 28:93-103 (2008); Kisseleva et al., "Recent Advances in Liver Stem Cell Therapy," *Curr. Opin. Gastroenterol.* 26(4):395-402 (2010); and Thompson et al., "Antifibrotic Therapies: Will We Ever Get There?" *Curr. Gastroenterol. Rep.* 12:23-29 (2010)).

Tissue repair is a multi-step process that is initiated upon tissue injury and involves platelet activation, blood clotting, and the local release of inflammatory mediators and cytokines. Following injury, fibronectin is crosslinked into the fibrin clot (Hynes R., *Fibronectins* (Springer-Verlag 1990) and Colvin R., "Fibronectin in Wound Healing," *In Fibronectin* (Mosher D. ed., 1989), where it promotes the migration and attachment of fibroblasts, endothelial cells, monocytes and neutrophils (Hynes R., *Fibronectins* (Springer-Verlag 1990); Colvin R., "Fibronectin in Wound Healing," *In Fibronectin* (Mosher D. ed., 1989); and Grinnell et al., "Fibroblast Adhesion to Fibrinogen and Fibrin Substrata: Requirement for Cold-Isoluble Globulin (Plasma Fibronectin)," *Cell* 19:517-525 (1980)). In later stages of tissue repair, the fibronectin-rich provisional matrix is replaced by granulation tissue, which is rich in collagen. Fibronectin matrix polymerization is required for deposition of collagen I fibrils (Sottile et al., "Fibronectin Polymerization Regulates the Composition and Stability of Extracellular Matrix Fibrils and Cell-Matrix Adhesions," *Mol. Biol. Cell.* 13:3546-3559 (2002); Sottile et al., "Fibronectin-Dependent Collagen I Deposition Modulates the Cell Response to Fibronectin," *Am. J. Physiol. Cell Physiol.* 293:C1934-1946 (2007); Velling et al., "Polymerization of Type I and III Collagens is Dependent on Fibronectin and Enhanced by Integrins alpha 11-beta 1 and alpha 2-beta 1," *J. Biol. Chem.* 277(40):37377-37381 (2002); and McDonald et al., "Role of Fibronectin in Collagen Deposition: Fab' to the Gelatin-Binding Domain of Fibronectin Inhibits both Fibronectin and Collagen Organization in Fibroblast Extracellular Matrix," *J. Cell. Biol.* 92:485-492 (1982)). Contraction of myofibroblasts within the granulation tissue serves to reduce the area of the wound and to enhance the mechanical strength of regenerating tissue (Mutsaers et al., "Mechanisms of Tissue Repair: From Wound Healing to Fibrosis," *Int. J. Biochem. Cell Biol.* 29(1):5-17 (1997)). Fibronectin matrix polymerization is an important regulator of cell growth, cell migration, cell contractility, and ECM remodeling (Sottile et al., "Fibronectin Polymerization Regulates the Composition and Stability of Extracellular Matrix Fibrils and Cell-Matrix Adhesions," *Mol. Biol. Cell.* 13:3546-3559 (2002); Sottile et al., "Fibronectin-Dependent Collagen I Deposition Modulates the Cell Response to Fibronectin," *Am. J. Physiol. Cell Physiol.* 293:C1934-1946 (2007); Hocking et al., "Stimulation of Integrin-Mediated Cell Contractility by Fibronectin Polymerization," *J. Biol. Chem.* 275:10673-10682 (2000); Sottile et al., "Fibronectin Matrix Assembly Enhances Adhesion-Dependent Cell Growth," *J. Cell Sci.* 111:2933-2943 (1998)), and as such, is an important regulator of tissue repair.

Many of the processes that occur in normal tissue repair also occur during fibrosis (Selman et al., "Idiopathic Pulmonary Fibrosis: Prevailing and Evolving Hypotheses About its Pathogenesis and Implications for Therapy," *Ann. Intern. Med.* 134(2):136-151 (2001) and Mutsaers et al., "Mechanisms of Tissue Repair: From Wound Healing to Fibrosis," *Int. J. Biochem. Cell Biol.* 29(1):5-17 (1997)). In fibrotic disorders, abnormal, excessive deposition of ECM leads to a disruption of normal tissue architecture and impaired organ function (Selman et al., "Idiopathic Pulmonary Fibrosis: Prevailing and Evolving Hypotheses About its Pathogenesis and Implications for Therapy," *Ann. Intern. Med.* 134(2):136-151 (2001); Zeisberg et al., "Role of Fibroblast Activation in Inducing Interstitial Fibrosis," *J. Nephrol.* 13 Suppl 3:S111-120 (2000); Fang, K C., "Mesenchymal Regulation of Alveolar Repair in Pulmonary Fibrosis," *Am. J. Respir. Cell Mol. Biol.* 23(2):142-145 (2000)). Enhanced fibronectin and collagen deposition is associated with fibrotic diseases including interstitial pulmonary fibrosis (Selman et al., "Idiopathic Pulmonary Fibrosis: Prevailing and Evolving Hypotheses About its Pathogenesis and Implications for Therapy," *Ann. Intern. Med.* 134(2):136-151 (2001); McDonald J., "Fibronectin In the Lung," *In Fibronectin* (Mosher D. ed., 1989)); Demling R H., "The Modern Version of Adult Respiratory Distress Syndrome," *Ann. Rev. Med.* 46:193-202 (1995); Gauldie et al., "TGF-β, Smad3 and the Process of Progressive Fibrosis," *Biochem. Soc. Trans.* 35(Pt 4):661-664 (2007)), renal fibrosis (Zeisberg et al., "Role of Fibroblast Activation in Inducing Interstitial Fibrosis," *J. Nephrol.* 13 Suppl 3:S111-120 (2000)), dermal fibrosis (Singer et al., "Cutaneous Wound Healing," *N. Engl. J. Med.* 341(10):738-746 (1999); Wolfram et al., Hypertrophic Scars and Keloids—A Review of Their Pathophysiology, Risk Factors, and Therapeutic Management," *Dermatol. Surg.* 35(2):171-181 (2009); Kischer et al., "Fibronectin (FN) in Hypertrophic Scars and Keloids," *Cell Tissue Res.* 231(1):29-37 (1983); Kischer et al., "Increased Fibronectin Production by Cell Lines from Hypertrophic Scar and Keloid," *Connect. Tissue Res.* 23(4):279-288 (1989)), liver fibrosis (Brenner, D. A., "Molecular Pathogenesis of Liver Fibrosis," *Trans. Am. Clin. Climatol. Assoc.* 120:361-368 (2009); Friedman, S. L., "Hepatic Stellate Cells: Protean, Multifunctional, and Enigmatic Cells of the Liver," *Physiol. Rev.* 88:125-172 (2008); Bedossa et al., "Liver Extracellular Matrix in Health and Disease," *J. Pathol* 200:504-515 (2003)), and cardiac fibrosis (Heling et al., "Increased Expression of Cytoskeletal, Linkage, and Extracellular Proteins in Failing Human Myocardium," *Circ. Res.* 86(8):846-853 (2000); van Dijk et al., "Accumulation of Fibronectin in the Heart after Myocardial Infarction: A Putative Stimulator of Adhesion and Proliferation of Adipose-Derived Stem Cells," *Cell Tissue Res.* 332(2):289-298 (2008); Tsutsumi et al., "Angiotensin II Type 2 Receptor is Upregulated in Human Heart with Interstitial Fibrosis, and Cardiac Fibroblasts are the Major Cell Type for its Expression," *Circ. Res.* 83(10):1035-1046 (1998)). Persistent fibroblast "activation" is thought to lead to continued fibroblast proliferation, excessive ECM production, and aberrant ECM remodeling. The underlying cause of this fibroblast "activation" is unknown, but may result from chronic inflammation, abnormal fibroblast response to growth factors, altered cell response to ECM, an altered balance of matrix degradation and deposition, and/or aberrant interactions between epithelial and mesenchymal cells (Selman et al., "Idiopathic Pulmonary Fibrosis: Prevailing and Evolving Hypotheses About its Pathogenesis and Implications for Therapy," *Ann. Intern. Med.* 134(2):136-151 (2001); Butler et al., "Current Progress in Keloid Research and Treatment," *J. Am. Coll. Surg.* 206 (4):731-741 (2008); Zeisberg et al., "Role of Fibroblast Activation in Inducing Interstitial Fibrosis," *J. Nephrol.* 13 Suppl 3:S111-120 (2000); Gauldie et al., "TGF-β, Smad3 and the Process of Progressive Fibrosis," *Biochem. Soc. Trans.* 35(Pt 4):661-664 (2007); Eckes et al., "Fibroblast-Matrix Interactions in Wound Healing and Fibrosis," *Matrix Biol.* 19(4):325-332 (2000)).

While modulation of fibronectin deposition and ECM formation has been demonstrated in vitro, the ability to control fibronectin deposition and ECM formation in vivo and the therapeutic utility of doing so remains elusive. The reason for this is that, as noted above, fibronectin deposition and ECM formation is necessary for normal function. Indeed, fibronectin knockout mice and collagen I knockout mice both die in utero (Lohler et al., "Embryonic Lethal Mutation in Mouse Collagen I Gene Causes Rupture of Blood Vessels and is Associated with Erthropoietic and Mesenchymal Cell Death," *Cell* 38:597-607 (1984); George et al., "Defects in Mesoderm, Neural Tube, and Vascular Development in Mouse Embryos Lacking Fibronectin," *Dev.* 119:1079-1091 (1993); and George et al., "Fibronectins are Essential for Heart and Blood Vessel Morphogenesis But are Dispersible for Initial Specification of Precursor Cells," *Blood* 90(8):3073-3081), suggesting that modification of fibronectin deposition and ECM formation processes can have unintentional and undesirable consequences. It would be desirable to identify an approach for treating fibrosis, particularly cardiac, pulmonary, liver, and/or dermal fibrosis, that offers improvement over current therapies.

The present invention is directed to overcoming these and other deficiencies in the art.

SUMMARY OF THE INVENTION

One aspect of the present invention is directed to a method of treating a subject for fibrosis. This method involves administering to the subject a fibronectin binding protein or polypeptide, where the fibronectin binding protein or polypeptide binds fibronectin and inhibits fibronectin matrix deposition under conditions effective to treat the subject for fibrosis.

Another aspect of the present invention is directed to a method of preventing fibrosis in a subject. This method involves administering to the subject a fibronectin binding protein or polypeptide, where the fibronectin binding protein or polypeptide binds fibronectin, thereby inhibiting fibronectin matrix deposition to prevent fibrosis in the subject.

A further aspect of the present invention is directed to a method of improving heart function in a subject in need thereof. This method involves administering to the subject a fibronectin binding protein or polypeptide, where the fibronectin binding protein or polypeptide binds fibronectin thereby inhibiting deposition of fibronectin into the extracellular matrix under conditions effective to improve heart function in the subject.

Yet another aspect of the present invention is directed to a method of preventing overscarring of a wound in a subject. This method involves administering to the subject a fibronectin binding protein or polypeptide, wherein the fibronectin binding protein or polypeptide binds fibronectin under conditions effective to prevent overscarring in the subject.

A further aspect of the present invention is directed to a method of treating a subject for atherosclerosis. This method involves administering to the subject a fibronectin binding protein or polypeptide, where the fibronectin binding protein or polypeptide binds fibronectin and inhibits fibronectin matrix deposition under conditions effective to treat the subject for atherosclerosis.

Still another aspect of the present invention is directed to a method of treating a subject for asthma. This method involves administering to the subject a fibronectin binding protein or polypeptide, wherein the fibronectin binding protein or polypeptide binds fibronectin and inhibits fibronectin matrix deposition under conditions effective to treat the subject for asthma.

The data herein show that fibronectin polymerization is an important regulator of ECM remodeling in vitro and in vivo. Applicants have characterized adhesin based peptides that interfere with fibronectin polymerization and attenuate excess fibronectin and collagen matrix deposition, block inflammation, and improve organ function in an in vivo model of vascular remodeling. This data indicates that fibronectin polymerization inhibitors are excellent therapeutic candidates for not only the treatment of vascular occlusive diseases, but also fibrosis and heart failure subsequent to vascular remodeling or infarct, which similarly involve abnormal extracellular matrix remodeling and inflammatory events.

The demonstrated in vivo therapeutic utility of fibronectin polymerization inhibition was not accompanied by any observable detriment to the animal. These data were unexpected in view of the complexity of the vascular remodeling process and the important role that both fibronectin and collagen play in mediating normal tissue repair and wound healing processes (Colvin R., *Fibronectin in Wound Healing*, in Fibronectin (Mosher D. ed., 1989); Grinnell, F., "Fibronectin and Wound Healing," *J. Cell Biochem.* 26:107 (1984); Mutsaers et al., "Mechanisms of Tissue Repair: From Wound Healing to Fibrosis," *Int J Biochem Cell Biol* 29 (1):5 (1997); Singer et al., "Cutaneous Wound Healing," *N Engl J Med* 341(10):738 (1999), which are hereby incorporated by reference in their entirety). These results are further surprising in view of the embryonic lethality associated with loss of either collagen I (Lohler et al., "Embryonic Lethal Mutation in Mouse Collagen I Gene Causes Rupture of Blood Vessels and is Associated with Erthropoietic and Mesenchymal Cell Death," *Cell* 38:597-607 (1984), which is hereby incorporated by reference in their entirety) or fibronectin (George et al., "Defects in Mesoderm, Neural Tube, and Vascular Development in Mouse Embryos Lacking Fibronectin," *Dev.* 119:1079-1091 (1993) and George et al., "Fibronectins are Essential for Heart and Blood Vessel Morphogenesis But are Dispersible for Initial Specification of Precursor Cells," *Blood* 90(8):3073-3081, which are hereby incorporated by reference in their entirety), which indicate the importance of these proteins in mediating normal cellular and developmental processes.

BRIEF DESCRIPTION OF THE DRAWINGS

FIG. 2A is a panel of representative photomicrographs of the left carotid artery 14 days after ligation. Lumen (L), intima (I), media (M) and adventitia (A) in ligated vessels are shown. Bar, 100 µm. Morphometric analyses of the lumen (FIG. 2B), intima-media (FIG. 2C), the external elastic lamina compartment (EEL; FIG. 2D), and adventitia (FIG. 2E) at 7 and 14 days after ligation were performed. * indicates $p<0.05$, $p<0.01$ and *$p<0.001$.

FIG. 3A is a panel showing immunohistochemical detection of fibronectin and collagen 17 or 14 days post surgery in the left carotid artery. Intima (I), media (M), and adventitia (A) are shown. Quantitation of immunostaining intensity of fibronectin (FIGS. 3B-3C) and collagen (FIG. 3D-3E) in the media and adventitia 7 and 14 days after ligation. Bar, µm. * indicates $p<0.05$, $p<0.01$ and *$p<0.001$.

FIG. 4A is a panel showing the immunohistochemical detection of smooth muscle myosin heavy chain (SMMHC) and SM α-actin in the left carotid artery 7 days after ligation. The media is denoted by the "M". Quantitative results of immunostaining intensities of SMMHC (FIG. 4B) and SM α-actin (FIG. 4C) in the media. Bar, 25 µm. *$p<0.05$, **$p<0.01$.

FIGS. 5A and 5B show the quantitative IHC analysis of the proliferation index (PCNA (+) cells per total cell number) in the intima-media and adventitia, respectively, 7 days post ligation. Sections of the left carotid artery were stained with antibodies to CD45 7 days after ligation to assess leukocyte infiltration. Sections were counterstained with hematoxylin. Percentage of the area which is CD45 (+) was assessed in the intima-media (FIG. 5C) and adventitia (FIG. 5D) of the vessels as described in the Examples. * indicates $p<0.05$, ** indicates $p<0.01$.

FIG. 14A shows a representative M-mode tracing from echocardiography 4 weeks post-MI (note small difference in scale: III-11C heart is larger). FIG. 14B show the % fractional shortening (FS) in control (III-11C, n=8) and pUR4 (n=9) groups. FIG. 14C shows the heart weight to body weight ratio (HW:BW). *p<0.05

DETAILED DESCRIPTION OF THE INVENTION

Figures 1A, 1B, 1C, 1D, 1E, 1F, 1G, 1H, 1I:
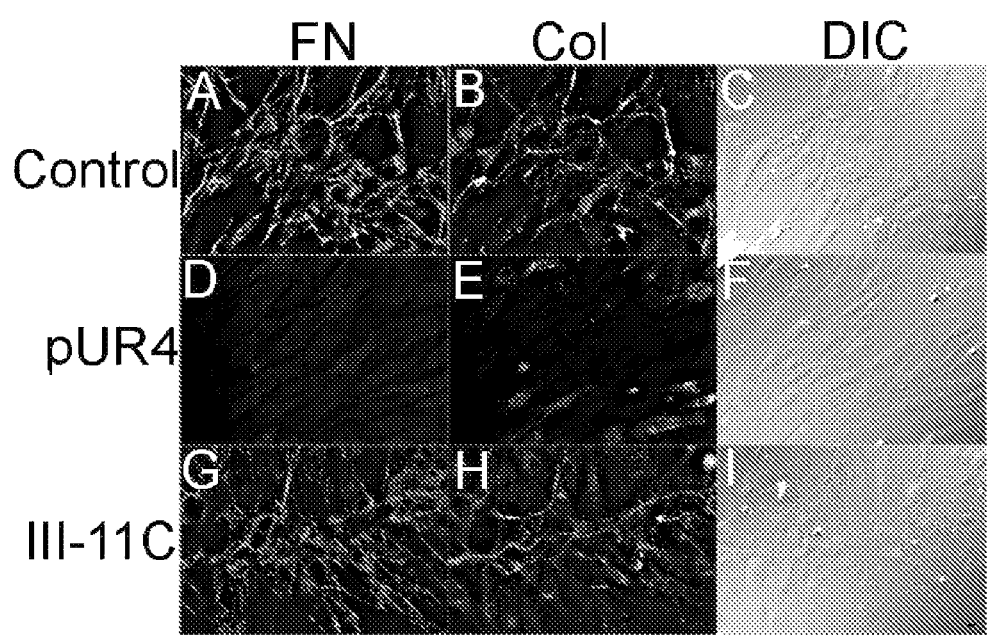
FIGS. 1A-1I depict the effect of pUR4 on fibronectin and collagen I deposition in smooth muscle cells (SMCs). Rat aortic SMCs were grown in serum containing media in the absence (FIGS. 1A-1C) or presence of 500 nM pUR4 (FIGS. 1D-1F) or control III-11C (FIGS. 1G-1I) peptides for 3 days. Cell were fixed, and then incubated with a polyclonal antibody to fibronectin (FIGS. 1A, 1D, and 1G) or collagen I (FIGS. 1B, 1E, and 1H). Corresponding differential interference contrast images are shown in FIGS. 1C, 1F, and 1I. Bar, 20 µm.

The present invention relates to various uses of fibronectin binding proteins or polypeptides, which are demonstrated herein as being capable of interfering with fibronectin deposition and extracellular matrix formation and stability in vivo (i.e., in a subject or patient). These uses include controlling fibrosis and fibrosis related disorders in a variety of tissues and organ systems, as discussed more fully below. As used herein, a "subject" or "patient" encompasses any animal, but preferably a mammal. More preferably, the subject or patient is a human Fibronectin binding proteins and polypeptides suitable for use in the methods of the present invention include, without limitation, those that inhibit fibronectin deposition and/or enhance fibronectin degradation and turnover. Preferably, the fibronectin binding proteins or polypeptides of the present invention also inhibit the deposition of one or more other extracellular matrix proteins such as collagen I, collagen III, thrombosponin-1, tenascin, fibulin, and fibrinogen and/or enhance the degradation and/or turnover of one or more other extracellular matrix proteins. The fibronectin binding proteins or polypeptides of the present invention preferably also inhibit inflammation associated with disease (i.e., heart failure, fibrosis, vascular occlusive disease).

The fibronectin binding proteins and polypeptides of the present invention may inhibit fibronectin (or other extracellular matrix protein) deposition directly or through inhibition of fibronectin polymerization Inhibition of fibronectin polymerization inhibits fibronectin and collagen deposition and enhances extracellular matrix fibronectin and collagen turnover in vitro (Sottile et al., "Fibronectin Polymerization Regulates the Composition and Stability of Extracellular Matrix Fibrils and Cell-Matrix Adhesions," *Mol. Biol. Cell.* 13:3546-3559 (2002) and Sottile et al., "Fibronectin Matrix Turnover Occurs Through a Caveolin-1-Dependent Process. *Mol. Biol. Cell.* 16(2):757-768 (2005), which are hereby incorporated by reference in their entirety). Peptides suitable for inhibiting fibronectin polymerization and, subsequently, fibronectin and collagen deposition include bacterial adhesin derived peptides. Class I bacterial adhesin based peptides that inhibit fibronectin polymerization include pUR4, $FNZ_{r2}$, and $FNBPA_{9-10}$ as shown in Table 1 below (Chiang et al., "Fibronectin Is an Important Regulator of Flow-Induced Vascular Remodeling," *Arterioscler. Thromb. Vasc. Biol.* 29(7): 1084-9 (2009), Tomasini-Johansson et al., "Peptide from Adhesin F1 Inhibits Fibronectin Matrix Assembly," *J. Biol. Chem.* 276:23430-23439 (2001), Ozeri et al., "A Two-Domain Mechanism for Group A Streptococcal Adherence Through Protein F to the Extracellular Matrix," *Embo J.* 15(5):989-998 (1996), Lindmark et al., "Fibronectin-Binding Protein of *Streptococcus equi* subsp. *Zooepidemicus*," *Infect. Immun.* 64(10):3993-3999 (1996), and Meenan et al., "The Tandem Beta-zipper Model Defines High Affinity Fibronectin-Binding Repeats within *Staphylococcus aureus* FNBPA," *J. Biol. Chem.* 282(35):25893-25902 (2007), which are hereby incorporated by reference in their entirety). The bold residues in each amino acid sequence are residues added to optimize cloning and expression and the non-bold amino acid residues define the active portion of each peptide. The bold residues can be modified (e.g., deleted or substituted) without altering the ability of the peptide to inhibit fibronectin polymerization.

TABLE 1

Bacterial Adhesin Derived Peptides

| Class I Inhibitor | pUR4 | MRGSHHHHHGSKDQSPLAGESGETEYITEVYGNQQNPVDIDKKLPNETGFSGNMVETEDT KLN (SEQ ID NO: 1) |
|---|---|---|
| | FNZr2 | GPLGSRNPHLMGIGGGLAGESGETTPKPGQTGGQGPVIETTEDTQKGMSGQSGGTIESENTKKPEVMIGGQGQTIETTEDTQKGMSGQSGGTIESEDTKKP (SEQ ID NO: 2) |
| | FNBPA 9-10 | GPLGSKYEQGGNIVDIDFDSVPQIHGQNKGNQSFEEDTEKDKPKYEHGGNIIDIDFDSVPHIHGFNKHTEIIEEDTNKDKP (SEQ ID NO: 3) |
| Class II Inhibitor | $R_1R_2$ | HHHHHHGSGLNGENQKEPEQGERGEAGPPLSGLSGNNQGRPSLPGLNGENQKEPEQGERGEAGPP KSN (SEQ ID NO: 4) |

Additional fibronectin binding proteins and polypeptides suitable for use in the methods of the present invention include, without limitation, those proteins or polypeptides that inhibit collagen deposition and/or extracellular matrix collagen degradation and turnover. Suitable proteins or peptides in accordance with this embodiment of the invention include peptides that interfere with fibronectin-collagen binding, including, for example, the class II bacterial adhesin derived peptide $R_1R_2$ (Table 1) (Sottile et al., "Fibronectin-Dependent Collagen I Deposition Modulates the Cell Response to Fibronectin," *Am. J. Physiol. Cell Physiol.* 293: C1934-1946 (2007) and Lindmark et al., "A Novel Fibronectin-Binding Protein from *Streptococcus equi*, Inhibits the Binding Between Fibronectin and Collagen," *Infect. Immun.* 67(5):2383-2388 (1999), which are hereby incorporated by reference in their entirety). The bold residues depicted in the $R_1R_2$ amino acid sequence of Table 1 are residues added to optimize cloning and expression (i.e., the non-bold amino acid residues define the active portion of the peptide). These residues can be modified (e.g., deleted or substituted) without altering the ability of the peptide to inhibit fibronectin-collagen interaction.

Fibronectin binding proteins or polypeptides that are homologous to the class I and class II bacterial adhesin peptides of Table 1 are also suitable for use in the methods of the present invention. Homologous proteins or polypeptides are preferably characterized by an amino acid sequence identity of at least about 60 percent, more preferably at least about 70 percent or 80 percent, most preferably at least about 85 percent or 90 percent or 95 percent as compared to the amino acid sequences of SEQ ID NOs 1-4 above.

Other fibronectin binding proteins and polypeptides that are suitable for use in the present invention include fibronectin-derived peptides that inhibit fibronectin polymerization, including the 70-kDa amino terminal fibronectin fragment described by Sottile et al., "Recombinant 70-kDa Protein from the Amino-Terminal Region of Rat Fibronectin Inhibits Binding of Fibronectin to Cells and Bacteria," *Protein Expr. Purif.* 1(2):104-110 (1990) and Sottile et al., "N-Terminal Type I Modules Required for Fibronectin Binding to Fibroblasts and to Fibronectin's III1 Module," *Biochem. J.* 323:51-60 (1997), which are hereby incorporated by reference in their entirety. The corresponding 70-kDa amino terminal fibronectin fragment derived from human fibronectin shown below as SEQ ID NO:5 is also suitable for use in the present invention. The first 18 amino acid residues of SEQ ID NO:5 (below) are not critical for inhibition of fibronectin polymerization. Accordingly, one or more of these amino acid residues can be deleted or modified without altering the desired activity of the peptide.

```
Gln Ala Gln Gln Met Val Gln Pro Gln Ser Pro Val Ala Val Ser Gln
1               5                   10                  15
Ser Lys Pro Gly Cys Tyr Asp Asn Gly Lys His Tyr Gln Ile Asn Gln
            20                  25                  30
Gln Trp Glu Arg Thr Tyr Leu Gly Asn Val Leu Val Cys Thr Cys Tyr
            35                  40                  45
Gly Gly Ser Arg Gly Phe Asn Cys Glu Ser Lys Pro Glu Ala Glu Glu
        50                  55                  60
Thr Cys Phe Asp Lys Tyr Thr Gly Asn Thr Tyr Arg Val Gly Asp Thr
65                  70                  75                  80
Tyr Glu Arg Pro Lys Asp Ser Met Ile Trp Asp Cys Thr Cys Ile Gly
            85                  90                  95
Ala Gly Arg Gly Arg Ile Ser Cys Thr Ile Ala Asn Arg Cys His Glu
            100                 105                 110
Gly Gly Gln Ser Tyr Lys Ile Gly Asp Thr Trp Arg Arg Pro His Glu
            115                 120                 125
Thr Gly Gly Tyr Met Leu Glu Cys Val Cys Leu Gly Asn Gly Lys Gly
        130                 135                 140
Glu Trp Thr Cys Lys Pro Ile Ala Glu Lys Cys Phe Asp His Ala Ala
145                 150                 155                 160
Gly Thr Ser Tyr Val Val Gly Glu Thr Trp Glu Lys Pro Tyr Gln Gly
            165                 170                 175
Trp Met Met Val Asp Cys Thr Cys Leu Gly Glu Gly Ser Gly Arg Ile
            180                 185                 190
```

-continued

```
Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
    210                 215                 220

Leu Gln Cys Ile Cys Thr Gly Asn Gly Arg Gly Glu Trp Lys Cys Glu
225                 230                 235                 240

Arg His Thr Ser Val Gln Thr Thr Ser Ser Gly Ser Gly Pro Phe Thr
                245                 250                 255

Asp Val Arg Ala Ala Val Tyr Gln Pro Gln Pro His Pro Gln Pro Pro
            260                 265                 270

Pro Tyr Gly His Cys Val Thr Asp Ser Gly Val Val Tyr Ser Val Gly
        275                 280                 285

Met Gln Trp Leu Lys Thr Gln Gly Asn Lys Gln Met Leu Cys Thr Cys
    290                 295                 300

Leu Gly Asn Gly Val Ser Cys Gln Glu Thr Ala Val Thr Gln Thr Tyr
305                 310                 315                 320

Gly Gly Asn Leu Asn Gly Glu Pro Cys Val Leu Pro Phe Thr Tyr Asn
                325                 330                 335

Gly Arg Thr Phe Tyr Ser Cys Thr Thr Glu Gly Arg Gln Asp Gly His
            340                 345                 350

Leu Trp Cys Ser Thr Thr Ser Asn Tyr Glu Gln Asp Gln Lys Tyr Ser
        355                 360                 365

Phe Cys Thr Asp His Thr Val Leu Val Gln Thr Gln Gly Gly Asn Ser
    370                 375                 380

Asn Gly Ala Leu Cys His Phe Pro Phe Leu Tyr Asn Asn His Asn Tyr
385                 390                 395                 400

Thr Asp Cys Thr Ser Glu Gly Arg Arg Asp Asn Met Lys Trp Cys Gly
                405                 410                 415

Thr Thr Gln Asn Tyr Asp Ala Asp Gln Lys Phe Gly Phe Cys Pro Met
            420                 425                 430

Ala Ala His Glu Glu Ile Cys Thr Thr Asn Glu Gly Val Met Tyr Arg
        435                 440                 445

Ile Gly Asp Gln Trp Asp Lys Gln His Asp Met Gly His Met Met Arg
    450                 455                 460

Cys Thr Cys Val Gly Asn Gly Arg Gly Glu Trp Thr Cys Ile Ala Tyr
465                 470                 475                 480

Ser Gln Leu Arg Asp Gln Cys Ile Val Asp Asp Ile Thr Tyr Asn Val
                485                 490                 495

Asn Asp Thr Phe His Lys Arg His Glu Glu Gly His Met Leu Asn Cys
            500                 505                 510

Thr Cys Phe Gly Gln Gly Arg Gly Arg Trp Lys Cys Asp Pro Val Asp
        515                 520                 525

Gln Cys Gln Asp Ser Glu Thr Gly Thr Phe Tyr Gln Ile Gly Asp Ser
    530                 535                 540

Trp Glu Lys Tyr Val His Gly Val Arg Tyr Gln Cys Tyr Cys Tyr Gly
545                 550                 555                 560

Arg Gly Ile Gly Glu Trp His Cys Gln Pro Leu Gln Thr Tyr Pro Ser
                565                 570                 575

Ser
```

Antibodies, including monoclonal, polyclonal, and fragments thereof, that bind to fibronectin and inhibit its deposition directly or inhibit its polymerization are also suitable for use in the methods of the present invention. Chernousov et al., "Role of the I-9 and III-1 Modules of Fibronectin in Formation of an Extracellular Fibronectin Matrix," *J. Bio. Chem.* 266(17):10851-58 (1991), which is hereby incorporated by reference in its entirety, describes the isolation and characterization of the 9D2 antibody, which recognizes the first type III module of fibronectin and inhibits fibronectin polymerization and deposition. The 92D antibody and other antibodies, or antibody fragments thereof, directed to similar epitopes of fibronectin are suitable for use in the methods of the present invention. The L8 antibody, which recognizes the region spanning the type I-9 and type III-1 modules of fibronectin, also inhibits fibronectin deposition (Chernousov et al., "Role of the I-9 and III-1 Modules of Fibronectin in Formation of an Extracellular Fibronectin Matrix," *J. Bio. Chem.* 266(17): 10851-58 (1991), which is hereby incorporated by reference in its entirety). The L8 antibody and other antibodies or antibody fragments thereof, recognizing similar epitopes of fibronectin are suitable for use in the methods of the present invention.

The fibronectin binding proteins or polypeptides of the present invention may be conjugated to a polymer that is stabilized to avoid enzymatic degradation of the conjugated protein or polypeptide upon administration. Conjugated proteins or peptides of this type are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., each of which is hereby incorporated by reference in its entirety.

Alternatively, the proteins or polypeptides of the present invention may be in the form of chimeric proteins, made in accordance with the methods disclosed in U.S. Pat. No. 5,817,789 to Heartlein et al., which is hereby incorporated by reference in its entirety. The chimeric protein can include a targeting domain and the fibronectin binding protein or polypeptide. The targeting domain comprises a signal peptide sequence that can direct the peptide to a specific cell- or tissue-type. The signaling peptide can include at least a portion of a ligand binding protein. The ligand domain is specific for receptors located on a cellular target, e.g., cardiocytes, smooth muscle cells, endothelial cells, and fibroblasts. Suitable ligand binding proteins include high-affinity antibody fragments (e.g., Fab, Fab' and F(ab')$_2$), single-chain Fv antibody fragments), nanobodies or nanobody fragments, fluorobodies, or aptamers. Other ligand binding proteins include biotin-binding proteins, lipid-binding proteins, periplasmic binding proteins, lectins, serum albumins, enzymes, phosphate and sulfate binding proteins, immunophilins, metallothionein, or various other receptor proteins. For cell specific targeting, the signaling peptide is preferably a ligand binding domain of a cell specific membrane receptor. Thus, when the modified peptide is delivered intravenously or otherwise introduced into blood or lymph, the peptide will be targeted to a desired tissue or cell. For targeting a peptide to a cardiac cell, the peptide may be conjugated to an antibody recognizing elastin microfibril interfacer (EMILIN2) (Van Hoof et al., "Identification of Cell Surface for Antibody-Based Selection of Human Embryonic Stem Cell-Derived Cardiomyocytes," *J Proteom Res* 9:1610-18 (2010), which is hereby incorporated by reference in its entirety), cardiac troponin I, connexin-43, or any cardiac cell-surface membrane receptor that is known in the art. Methods of preparing such chimeric proteins and peptides are described in U.S. Pat. No. 5,817,789 to Heartlein et al., which is hereby incorporated by reference in its entirety.

A first aspect of the present invention relates to a method of improving heart function in a subject in need thereof. This method involves administering to the subject a fibronectin binding protein or polypeptide, where the fibronectin binding protein or polypeptide binds fibronectin thereby inhibiting deposition of fibronectin into the extracellular matrix under conditions effective to improve heart function in the subject.

A subject suitable for treatment in accordance with this aspect of the present invention includes any subject having impaired cardiac function that may or may not be accompanied by progressive cardiac remodeling. Impaired cardiac function and ensuing heart failure may have an ischemic or non-ischemic origin. Subjects having ischemic heart injury, arising from a reduced supply of blood to the heart, may suffer from angina pectoris (pain in the chest), myocardial infarction or acute myocardial infarction (resulting from acute coronary artery occlusion causing a damaged myocardium with scar tissue), and chronic congestive heart failure, including chronic ischemic cardiomyopathy. Subjects having non-ischemic heart disease include those subjects suffering from idiopathic dilated cardiomyopathy and cardiomyopathy due to hypertension, valvular disease, including cardiac fibrosis, and congenital defects. Cardiac remodeling includes any alteration in the structure and function of the heart in response to hemodynamic load and/or cardiac injury. Pathological cardiac remodeling may occur with pressure overload (e.g., aortic stenosis, hypertension), volume overload (e.g., valvular regurgitation), or following cardiac injury (e.g., myocardial infarction, myocarditis, or idiopathic dilated cardiomyopathy).

Another aspect of the present invention relates to methods of treating and preventing fibrosis and fibrosis related conditions in a subject. These methods involve administering to a subject having fibrosis, or a fibrosis related condition, a fibronectin binding protein or polypeptide that inhibits fibronectin matrix deposition under conditions effective to treat the subject for fibrosis. Treating a subject for fibrosis or a fibrosis related condition according to the methods of the present invention includes reducing, inhibiting, or preventing the progression of fibrosis or the fibrosis related condition.

Fibrosis is the abnormal accumulation of fibrous tissue that can occur as a part of the wound-healing process in damaged tissue. Such tissue damage may result from physical injury, inflammation, infection, exposure to toxins, and other causes. Examples of fibrosis include, without limitation, dermal scar formation, keloids, liver fibrosis, lung fibrosis, kidney fibrosis, and glomerulosclerosis.

Liver (hepatic) fibrosis, for example, occurs as a part of the wound-healing response to chronic liver injury. Such damage may be the result of viral activity (e.g., chronic hepatitis types B or C) or other infections (e.g., parasites, bacteria), chemicals (e.g., pharmaceuticals, alcohol, pollutants), immune processes (e.g., autoimmune hepatitis), metabolic disorders (e.g., lipid, glycogen, or metal storage disorders), or cancer growth. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver failure, and death.

Fibrotic disorders of the kidney include, without limitation, glomerulonephritis (including membranoproliferative, diffuse proliferative, rapidly progressive, post-infectious, and chronic forms), diabetic glomerulosclerosis, focal glomerulosclerosis, diabetic nephropathy, lupus nephritis, tubulointerstitial fibrosis, membranous nephropathy, amyloidosis (which affects the kidney among other tissues), renal arteriosclerosis, nephrotic syndrome, renal interstitial fibrosis, renal fibrosis in patients receiving cyclosporin, and HIV associated nephropathy. The glomerulus is a major target of many types of renal injury, including immunologic (e.g., immune-complex- or T-cell-mediated), hemodynamic (systemic or renal hypertension), metabolic (e.g., diabetes), "atherosclerotic"

(accumulation of lipids in the glomerulus), infiltrative (e.g., amyloid), and toxicant (e.g., snake venom). The renal structural changes in patients with diabetic nephropathy include hypertrophy of the glomerulus, thickening of the glomerular and tubular membranes (due to accumulated matrix), and increased amounts of matrix in the measangium and tubulointerstitium. Glomerular hypertension due to intrarenal hemodynamic changes in diabetes can contribute to the progression of diabetic nephropathy. Autoimmune nephritis can also lead to altered mesangial cell growth responses. Infection by hepatitis-C virus can also result in idiopathic membranoproliferative glomerulonephritis.

Fibrotic disorders of the lung include, without limitation, silicosis, asbestosis, idiopathic pulmonary fibrosis, bronchiolitis obliterans-organizing pneumonia, pulmonary fibrosis associated with high-dose chemotherapy, idiopathic pulmonary fibrosis, and pulmonary hypertension. These diseases are characterized by cell proliferation and increased production of extracellular matrix components, such as collagens, elastin, fibronectin, and tenascin-C. The methods of the present invention can also be utilized to treat a subject having asthma and other conditions of the lung associated with airway remodeling.

Pancreatic fibrosis occurs in chronic pancreatitis. This condition is characterized by duct calcification and fibrosis of the pancreatic parenchyma. Like liver cirrhosis, chronic pancreatitis is associated with alcohol abuse.

The methods of the present invention are also suitable for the treatment of intestinal fibrosis, particularly fibrosis associated with inflammatory bowl diseases (e.g., Crohn's disease and ulcerative colitis).

Dermal fibrotic conditions which may be treated by the methods of the present invention include, but are not limited to, scleroderma, morphea, keloids, hypertrophic scars, familial cutaneous collagenoma, and connective tissue nevi of the collagen type. In addition, the methods of the present invention are suitable for inhibiting overproduction of scarring in patients who are known to form keloids or hypertrophic scars, inhibiting or preventing scarring or overproduction of scarring during healing of various types of wounds including surgical incisions, surgical abdominal wounds and traumatic lacerations, preventing or inhibiting scarring and reclosing of arteries following coronary angioplasty, and preventing or inhibiting excess scar or fibrous tissue formation associated with cardiac fibrosis after infarction and in hypersensitive vasculopathy.

Fibrotic conditions of the eye include conditions such as diabetic retinopathy, postsurgical scarring (for example, after glaucoma filtering surgery and after cross-eye surgery), and proliferative vitreoretinopathy.

Fibroproliferative disorders of bone are characterized by aberrant and ectopic bone formation, commonly seen as active proliferation of the major cell types participating in bone formation as well as elaboration by those cells of a complex bone matrix. Exemplary of such bone disorders is the fibrosis that occurs with prostate tumor metastases to the axial skeleton. In prostate tumor-related cancellous bone growth, prostate carcinoma cells can interact reciprocally with osteoblasts to produce enhanced tumor growth and osteoblastic action when they are deposited in bone. Fibroproliferative responses of the bone originating in the skeleton per se include ostepetrosis and hyperstosis. A defect in osteoblast differentiation and function is thought to be a major cause in osteopetrosis, an inherited disorder characterized by bone sclerosis due to reduced bone resorption, marrow cavities fail to develop, resulting in extramedullary hematopoiesis and severe hematologic abnormalities associated with optic atrophy, deafibronectiness, and mental retardation. In osteoarthritis, bone changes are known to occur, and bone collagen metabolism is increased within osteoarthritic femoral heads. The greatest changes occur within the subchondral zone, supporting a greater proportion of osteoid in the diseased tissue.

Fibroproliferative disorders of the vasculature include, for example, transplant vasculopathy, which is a major cause of chronic rejection of heart transplantation. Transplant vasculopathy is characterized by accelerated atherosclerotic plaque formation with diffuse occlusion of the coronary arteries, which is a classic fibroproliferative disease.

Additional fibrotic conditions which may be treated by the methods of the present invention include: rheumatoid arthritis, diseases associated with prolonged joint pain and deteriorated joints, progressive systemic sclerosis, polymyositis, dermatomyositis, eosinophilic fascitis, morphea, Raynaud's syndrome, and nasal polyposis.

Another aspect of the present invention is directed to a method of treating a condition associated with vascular remodeling. This method involves administering to the subject a fibronectin binding protein or polypeptide, where the fibronectin binding protein or polypeptide binds fibronectin thereby inhibiting fibronectin matrix deposition under conditions effective to treat the vascular remodeling. As used herein, "vascular remodeling" means a diminution in vessel lumen volume, diameter, or area that is the result of neointimal thickening or smooth muscle cell proliferation, and which may occur as the result of disease, infection, or procedural vascular trauma. Vascular remodeling also encompasses compensatory enlargement of a vessel which accompanies neointimal proliferation.

In accordance with this embodiment of the present invention, procedural vascular traumas resulting in vascular remodeling that can be treated using the methods of the present invention include, without limitation, organ transplantation, such as heart, kidney, liver and the like that involve vessel anastomosis; vascular surgery (e.g., coronary bypass surgery, biopsy, heart valve replacement, atheroectomy, thrombectomy); transcatheter vascular therapies including angioplasty; vascular grafting using natural or synthetic materials, (e.g., saphenous vein coronary bypass grafts, dacron and venous grafts used for peripheral arterial reconstruction); placement of a mechanical shunt (e.g., a PTFE hemodialysis shunt used for arteriovenous communications); and placement of an intravascular stent, staple, or suture, which may be metallic, plastic, or a biodegradable polymer.

Non-limiting examples of pathological vascular remodeling that can be treated using the methods of the present invention include vascular smooth muscle cell (VSMC) proliferation, neointima hyperplasia, thrombosis, vascular narrowing, vascular occlusion, injury-induced vascular narrowing, injury-induced vascular occlusion, arterial dilation, hypertension, restenosis, aneurism, allograft vasculopathy, arteriosclerosis, ischemia, injury-induced ischemia, myocardial infarction, cerebrovascular infarction, graft stenosis, and combinations thereof.

Vascular occlusive diseases that can be treated in accordance with this aspect of the invention include, without limitation, venous thromboembolic disorders (e.g., deep vein thrombosis, sickle cell diseases, and pulmonary embolism), arterial thromboembolic disorders (e.g., coronary artery diseases, including atherosclerosis, cerebrovascular disorders, and peripheral artery diseases), aortoiliac occlusive disease or Leriche's syndrome, Buerger's disease, carotid occlusive disease, and chronic arterial occlusive disease.

In accordance with the methods of the present invention, the fibronectin binding proteins or polypeptides can be administered alone or in combination with other therapeutic agents depending upon the nature of the condition being treated. In one embodiment of the present invention, the fibronectin binding proteins or polypeptides are administered in combination with one or more agents that are useful in treating fibrosis or the fibrosis related disorders, or agents that can treat or prevent symptoms associated with or caused by fibrosis related disorders. In accordance with this embodiment, suitable combination therapies may include, for example and without limitation, fibronectin binding proteins or polypeptides with anti-inflammatory and anti-fibrotic agents such as, corticosteroids, mycophenolate mofetil (Cellcept), cyclophosphamide, azathioprine, methotrexate, cyclosporine, prednisolone, pirfenidone, Medrol, penicillamine and colchicine.

In another embodiment of the present invention, the fibronectin binding proteins or polypeptides are administered in combination with one or more agents that are useful in treating a subject having impaired cardiac function. In accordance with this embodiment, suitable combination therapies may include, for example and without limitation, fibronectin binding proteins or polypeptides with: Angiotensin converting enzyme (ACE) inhibitors, angiotensin receptor blockers, aldosterone inhibitors, beta-adrenergic receptor blockers, diuretics, statins, mTOR inhibitors, anticoagulant drugs, and angiotensin II receptor antagonists, all standard of care pharmacological therapy for heart failure against which the fibronectin peptides would need to be tested for comparative efficacy. Alternatively, the fibronectin binding protein or polypeptides may be used in combination with surgical intervention (e.g., implantation of a left ventricular assist device, coronary artery bypass graft, etc) and administered at the time of or immediately following surgical intervention.

Examples of suitable ACE inhibitors include, without limitation, AB-103, ancovenin, benazeprilat, BRL-36378, BW-A575C, CGS-13928C, CL242817, CV-5975, Equaten, EU4865, EU-4867, EU-5476, foroxymithine, FPL 66564, FR-900456, Hoe-065, 15B2, indolapril, ketomethylureas, KR1-1177, KR1-1230, L681176, libenzapril, MCD, MDL-27088, MDL-27467A, moveltipril, MS41, nicotianamine, pentopril, phenacein, pivopril, rentiapril, RG-5975, RG-6134, RG-6207, RGH0399, ROO-911, RS-10085-197, RS-2039, RS 5139, RS 86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y-23785, Yissum, P-0154, zabicipril, AB-47, alatriopril, BMS 182657, Dainippon DU-1777, mixanpril, Prentyl, zofenoprilat, idrapril, perindoprilat, alacepril, benazepril, captopril, Cilazapril, delapril, enalapril, enalaprilat, fosinopril, fosinoprilat, imidapril, lisinopril, perindopril, and combinations thereof.

Examples of suitable statins include, without limitation, lovastatin, amlodipine, rosuvastatin, fluvastatin, atorvastatin, pravastatin, and simvastatin.

Anticoagulants suitable for use in the present invention include, without limitation, warfarin, heparin, clopidogrel, ticlopidine, enoxaparin, fondaparinux, idraparinux, sodium citrate, acid-citrate-dextrose, ethanedioate, EDTA, argatroban, lepirudin, bivalirudin, dabigatran, acenocoumarol, phenprocoumon, coumadin, and dicumarol.

Examples of suitable angiotensin II antagonists include, without limitation, saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E-4177, EMD-73495, eprosartan, HN-65021, irbesartan, L-159282, ME3221, Tasosartan, Telmisartan, and combinations thereof.

In another embodiment of the present invention, the fibronectin binding proteins or polypeptides are administered in combination with one or more agents that are useful in treating a subject having a vascular occlusive disease. In accordance with this embodiment, suitable combination therapies may include, for example and without limitation, fibronectin binding proteins or polypeptides with anti-platelet drugs, aspirin, clopidogrel, and statins. Alternatively, the fibronectin binding protein or polypeptides may be used in combination with angioplasty, plaque excision, or bypass grafting, and administered at the time of or immediately following such procedures.

The mode of affecting delivery of the fibronectin binding proteins and polypeptides of the present invention to modulate fibronectin deposition and thereby achieve therapeutic utility, vary depending on the type of therapeutic agent (e.g., a fibronectin peptide or a nucleic acid encoding a fibronectin peptide) and the condition to be treated.

Fibronectin binding proteins or polypeptides can be administered orally, parenterally, for example, subcutaneously, intravenously, intramuscularly, intraperitoneally, periadventitially, by inhalation, by intranasal instillation, by implantation, by intracavitary or intravesical instillation, intraocularly, intraarterially, intracardially (intracardiac), intralesionally, transdermally, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

In one embodiment of the present invention, the fibronectin binding proteins or polypeptides are delivered by implantation via a synthetic material, where the fibronectin binding protein or polypeptide is dispersed throughout the synthetic material and the synthetic material releases or elutes the therapeutic protein or polypeptide at the target tissue over a sustained period of time (e.g., hours, days, weeks, etc.). In accordance with this aspect of the invention, the synthetic material can be, without limitation, a biocompatible polymer, stents, implantable surgical products (e.g., staples, sutures, fasteners, etc.), adventitial wrap, mesh, synthetic graft or covering, biological matrix support material, or a biological dermal substitute. The synthetic material containing the fibronectin binding protein or polypeptide is implanted, inserted, grafted, or injected into the target tissue for effectuating localized delivery.

For treating a subject having impaired cardiac function or treating a subject having a vascular occlusive disease, it may be desirable to deliver the fibronectin binding protein or polypeptide using a biocompatible polymer, a stent e.g., coronary vascular stents, peripheral vascular stents, arotic stents, etc.), or sutures, or other implantable formulation. As used herein, a biocompatible polymer refers to a compound that is biostable, bioerodable, and/or bioresorbable. A biocompatible polymer may be a homopolymer or a copolymer and may contain a reactive chemical functionality that allows for grafting. A biocompatible copolymer may contain both hydrophobic and hydrophilic portions and may be a synthetic polymer, derived from naturally occurring polymers, e.g., cellulose, collagen, gelatin, fibrin, chitosan, etc. Suitable biocompatible polymers include those disclosed in U.S. Pat. No. 7,709,439 to Helmus et al., which is hereby incorporated by reference in its entirety. Other implantable delivery systems include, without limitation, microspheres, hydrogels, polymeric reservoirs, cholesterol matrices, polymeric systems and non-polymeric systems. A number of suitable implantable delivery systems are also disclosed by U.S. Pat. No. 6,464,687 to Ishikawa et al. and U.S. Pat. No. 6,074,673 to Guillen, which are hereby incorporated by reference in their entirety. Use of a biocompatible polymer or implantable formulation may be desirable for achieving periadventitial delivery of the fibronectin binding protein or polypeptide as described in the Examples herein. Release of the drug(s) can be controlled via selection of materials and the amount of drug loaded into the vehicle.

For treating or preventing dermal fibrosis or inhibiting overscarring in a subject, it may be desirable to deliver the fibronectin binding protein or polypeptide using a biological dermal substitute. As used herein, biological dermal substitute refers to a skin substitute or artificial dermal replacement. The dermal substitute comprises a scaffold into which cells can migrate and repair a wound. Several biological dermal substitutes are known in the art, including, without limitation, acellular dermal substitute (ADM), a dermal collagen matrix derived from banked human skin that has been treated to remove all cellular component (see Takami et al., "Dispase/ Detergent Treated Dermal Matrix as a Dermal Substitute," *Burns* 22:182-90 (1996), which is hereby incorporated by reference in its entirety; Alloderm® (LifeCell Corporation, Branchburg, N.J.), also a dermal collagen matrix derived from banked human skin that is treated to remove most cellular components; Dermagraft TC® (Advanced Tissue Sciences, La Jolla, Calif.), a woven bioabsorable polymer membrane within which human dermal fibroblasts are grown and devitalized; Dermalogen® (Collagenesis, Beverely, Mass.), a powdered human dermal collagen matrix that is treated to remove some cellular components; Integra® (Integra Life Sciences Corp., Plainsboro, N.J.), a bilayer artificial skin replacement with a dermal layer composed of bovine collagen gel cross-linked with shark chondroitin-6-sulfate. Other biological dermal substitutes known in the art are suitable for use in the present invention.

Fibronectin binding proteins or polypeptides may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, fibronectin binding proteins or polypeptides may be incorporated with excipients and used in the form of tablets, capsules, elixirs, suspensions, syrups, and the like. Such compositions and preparations should contain at least 0.1% of active fibronectin binding proteins or polypeptides. The percentage of the fibronectin binding proteins or polypeptides in these compositions may, of course, be varied and may conveniently be between about 2% to about 60% of the weight of the unit. The amount of fibronectin binding proteins or polypeptides in such therapeutically useful compositions is such that a suitable dosage will be obtained. Preferred compositions according to the present invention are prepared so that an oral dosage unit contains between about 1 and 250 mg of active compound (i.e., fibronectin binding protein or polypeptide).

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The fibronectin binding proteins and polypeptides can also be formulated as a cream or gel for topical or direct application to skin (e.g., for the treatment of dermal fibrosis) or to a wound (e.g., for the inhibition of overscarring).

The fibronectin binding proteins and polypeptides may also be administered parenterally. Solutions or suspensions of fibronectin binding proteins or polypeptides can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Fibronectin binding proteins or polypeptides may also be administered directly to the airways in the form of an aerosol (e.g., for the treatment of asthma). For use as aerosols, the compounds of the present invention in solution or suspension may be packaged in a pressurized aerosol container together with suitable propellants, for example, hydrocarbon propellants like propane, butane, or isobutane with conventional adjuvants. The fibronectin binding proteins or polypeptides also may be administered in a non-pressurized form such as in a nebulizer or atomizer.

The fibronectin protein or polypeptide of the invention can be administered before injury (i.e., cardiac or vascular remodeling event or injury) or at or before the onset of a disease condition (i.e., fibrosis) and after injury or onset of disease. Alternatively, the protein or polypeptide of the invention is administered only after injury or onset of disease. In accordance with this embodiment of the invention, when the protein or polypeptide is administered following cardiac or vascular injury (e.g., procedural trauma or infarct) it is administered 1 day after injury, 2 days after injury, 3-5 days after injury, etc. In yet another embodiment, the fibronectin protein or polypeptides of the invention are administered after diagnosis of fibrotic disorder or related condition to inhibit the progression of the disease. Administration of fibronectin binding proteins and polypeptides may be repeated periodically, e.g. every 6 hours, every 12 hours, daily, every other day, weekly, etc.

In an alternative embodiment of the present invention, a nucleic acid molecule encoding a fibronectin binding protein or polypeptide operably linked to a secretory signal sequence may be incorporated into a gene therapy vector to facilitate delivery. A secretory signal sequence comprises a DNA sequence that encodes a secretory peptide that, as a component of a larger polypeptide, directs the larger polypeptide through a secretory pathway of a cell in which it is synthesized. The larger polypeptide is commonly cleaved to remove the secretory peptide during transit through the secretory pathway. Examples of suitable secretory signal sequences include, without limitation, sequences encoding the fibronectin secretory signal peptide as described in U.S. Pat. No. 7,071,172 to McCown et al., which is hereby incorporated by reference, and sequences encoding the t-PA or MAPP (mammalian adhesion protease peptide) secretory signal peptides as described in U.S. Pat. No. 6,420,154 to Sheppard et al., which is hereby incorporated by reference in its entirety. Other secretory signals (also known as signal peptides, leader sequences, prepro sequences or pre sequences) known in the art are suitable for use in this embodiment of the invention. While secretory signal sequences are commonly positioned 5' to the nucleotide sequence encoding the polypeptide of interest, certain secretory signal sequences may be positioned elsewhere in the nucleotide sequence of interest (see e.g., U.S. Pat. No. 5,037,743 to Welch et al and U.S. Pat. No. 5,143,830 to Holland et al, which are hereby incorporated by reference in their entirety).

Suitable gene therapy vectors include viral expression vectors such as, adenovirus, adeno-associated virus, retrovirus, lentivirus, or herpes virus.

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant α1-Antitrypsin Gene to the Lung Epithelium In Vivo," *Science* 252:431-434 (1991), WO 1993/007283 to Curiel et al., WO 1993/006223 to Perricaudet et al., and WO1993/007282 to Curiel et al., which are hereby incorporated by reference in their entirety. Additional types of adenovirus vectors are described in U.S. Pat. No. 6,057,155 to Wickham et al., U.S. Pat. No. 6,033,908 to Bout & Hoeben, U.S. Pat. No. 6,001,557 to Wilson et al., U.S. Pat. No. 5,994,132 to Chamberlain & Kumar-Singh, U.S. Pat. No. 5,981,225 to Kochanek & Schniedner, U.S. Pat. No. 5,885,808 to Spooner & Epenetos, and U.S. Pat. No. 5,871,727 to Curiel, which are hereby incorporated by reference in their entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-Target Inhibition of HIV-1 in vitro by Means of an Adeno-associated Virus Antisense Vector," *Science* 258:1485-8 (1992), Walsh et al., "Regulated High Level Expression of a Human γ-Globin Gene Introduced into Erythroid Cells by an Adeno-Associated Virus Vector," *Proc. Nat'l. Acad. Sci. USA* 89:7257-61 (1992), Walsh et al., "Phenotypic Correction of Fanconi Anemia in Human Hematopoietic Cells with a Recombinant Adeno-Associated Virus Vector," *J. Clin. Invest.* 94:1440-8 (1994), Flotte et al., "Expression of the Cystic Fibrosis Transmembrane Conductance Regulator from a Novel Adeno-Associated Virus Promoter," *J. Biol. Chem.* 268:3781-90 (1993), Ponnazhagan et al., "Suppression of Human α-Globin Gene Expression Mediated by the Recombinant Adeno-Associated Virus 2-based Antisense Vectors," *J. Exp. Med.* 179:733-8 (1994), Miller et al., "Recombinant Adeno-Associated Virus (rAAV)-Mediated Expression of a Human γ-Globin Gene in Human Progenitor-Derived Erythroid Cells," *Proc. Nat'l. Acad. Sci. USA* 91:10183-7 (1994), Einerhand et al., "Regulated High-Level Human β-Globin Gene Expression in Erythroid Cells Following Recombinant Adeno-Associated Virus-Mediated Gene Transfer," *Gene. Ther.* 2:336-43 (1995), Luo et al., "Adeno-Associated Virus 2-Mediated Gene Transfer and Functional Expression of the Human Granulocyte-Macrophage Colony-Stimulating Factor," *Exp. Hematol.* 23:1261-7 (1995), and Zhou et al., "Adeno-Associated Virus 2-Mediated Transduction and Erythroid Cell-Specific Expression of a Human β-Globin Gene," *Gene Ther.* 3:223-9 (1996), which are hereby incorporated by reference in their entirety. In vivo use of these vehicles is described in Flotte et al., "Stable In Vivo Expression of the Cystic Fibrosis Transmembrane Conductance Regulator with an Adeno-Associated Virus Vector," *Proc Nat'l Acad Sci USA* 90:10613-7 (1993), and Kaplitt et al., "Long-Term Gene Expression and Phenotypic Correction Using Adeno-Associated Virus Vectors in the Mammalian Brain," *Nat. Genet.* 8:148-54 (1994), which are hereby incorporated by reference in their entirety.

Retroviral vectors which have been modified to form infective transformation systems can also be used to deliver a recombinant gene encoding a fibronectin binding protein or polypeptide product to a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, U.S. Patent Application Publication No. 2004/0170962 to Kafri et al., and U.S. Patent Application Publication No. 2004/0147026 to Arya, which are hereby incorporated by reference in their entirety.

Regardless of the type of infective transformation system employed, it should be targeted for delivery of the nucleic acid to a specific cell type. For example, for delivery of the nucleic acid into a cluster of cells (e.g., cardiac cells, fibroblasts, smooth muscle cells, endothelial cells) a high titer of the infective transformation system can be injected directly within the site of those cells so as to enhance the likelihood of cell infection. The infected cells will then express and secrete the desired product, in this case, a fibronectin binding protein or polypeptide to inhibit fibronectin polymerization and deposition in the surrounding extracellular matrix The expression system can further contain a promoter to control or regulate the strength and specificity of expression of the fibronectin binding protein or polypeptide in the target tissue.

One of skill in the art can readily select appropriate constitutive mammalian promoters based on their strength as a promoter. As an alternative to constitutive promoters, a mammalian tissue-specific promoter can be utilized. Any of a variety of tissue specific promoters are known in the art and can be selected based upon the tissue or cell type to be treated. For example, in one aspect of the invention it is desirable to decrease fibronectin deposition involved in cardiac dysfunction. Cardiac cell specific expression can be achieved using a cardiomyocyte-specific promoter such as the alpha-myosin heavy chain promoter (Akaiwa et al., "Cardiomyocyte-specific Gene Expression Following Recombinant Adeno-associated Viral Vector Transduction," *J. Biol. Chem.* 277(21): 18979-18985 (2002), which is hereby incorporated by reference in its entirety) or a VSMC-specific promoter such as a synthetic promoter containing the aortic preferentially expressed gene-1 (APEG-1) E box motif (Hsieh et al., "Genomic Cloning and Promoter Analysis of Aortic Preferentially Expressed Gene-1: Identification of a Vascular Smooth Muscle-Specific Promoter Mediated by an E Box Motif," *J Biol Chem* 274(20):14344-14351 (1999), which is hereby incorporated by reference in its entirety) can be utilized. Also, a promoter specific for microvascular endothelial cells can be used, such as the promoter of calcitonin receptor-like receptor (CRLR) (Nikitenko et al., "Transcriptional Regulation of the CRLR Gene in Human Microvascular Endothelial Cells by Hypoxia," *FASEB J.* 17(11):1499-501 (2003), which is hereby incorporated by reference in its entirety).

Gene expression can be regulated to achieve optimal expression levels and reduce side effects associated with constitutive gene expression. Whether the promoter is tissue-specific or not, the promoter can also be made inducible for purposes of controlling when expression or suppression of the fibronectin binding protein or polypeptide is desired. One of skill in the art can readily select appropriate inducible mammalian promoters from those known in the art. One exemplary inducible promoter includes a Tet-O response element (Farson et al., "A New-Generation Stable Inducible Packaging Cell Line for Lentiviral Vectors," *Hum. Gene Ther* 12(8):981-97 (2001), which is hereby incorporated by reference in its entirety). When used in combination with a tissue-specific promoter, the Tet-O response elements can render a tissue-specific promoter inducible to tetracycline and its derivatives (see e.g., Michalon et al., "Inducible and Neuron-Specific Gene Expression in the Adult Mouse Brain with the rtTA2S-M2 System," *Genesis* 43(4):205-12 (2005), which is hereby incorporated by reference in its entirety).

Another approach that is appropriate for cardiac protection against ischemia/reperfusion injury may involve turning on gene expression with the onset of ischemia (hypoxia), so that the gene product is already present during reperfusion. Many transcription factors are modified by hypoxic and oxidative stress. Studies of molecular responses to hypoxia have identified HIF-1α as the master regulator of hypoxia-inducible gene expression. Under hypoxic conditions, HIF-1α binds to the hypoxia-responsive element (HRE) in the enhancer region of its target genes and turns on gene transcription. Additionally, reperfusion or reoxygenation after ischemia increases the transactivating ability of NFκB. Genes regulated by NFκB include cytokines and adhesion molecules. Accordingly, in one aspect of the invention, at least one HRE is utilized as an enhancer to drive transgene expression in the expression system encoding the desired fibronectin binding protein or polypeptide. Suitable HRE nucleic acid constructs and expression systems are described in U.S. Pat. No. 5,942,434 to Ratcliffe et al., which is hereby incorporated by reference in its entirety. To assure sufficient duration of the transgene expression to achieve myocardial protection during the reperfusion period, a second regulatory element that is activated by oxidative stress such as NFκB responsive element is employed.

Recombinant cell therapy, which is a form of gene therapy, can also be utilized for the delivery of nucleic acid molecule encoding the desired fibronectin binding protein or polypeptide to cardiac tissue, for example, for the treatment of coronary disorders. In this approach, a target cell is transfected (i.e., transformed or transduced) with a nucleic acid encoding the fibronectin binding protein or polypeptide and, in turn, the target cell produces and secretes the gene product that exerts a therapeutic effect. Target cell transfection can be transient or stable (i.e., the nucleic acid becomes integrated into the genome of the target cell), and the target cell can be heterologous, or preferably autologous to the patient. Once the target cell or cells are producing and secreting the fibronectin binding protein or polypeptide, they are administered to the patient.

The fibronectin proteins or polypeptides of the present invention may be prepared using standard methods of synthesis known in the art, including solid phase peptide synthesis (Fmoc or Boc strategies) or solution phase peptide synthesis. Alternatively, peptides of the present invention may be prepared using recombinant expression systems.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by Joseph Sambrook et al., Molecular Cloning: A Laboratory Manual (Cold Springs Harbor 1989), which is hereby incorporated by reference in its entirety. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR.

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated peptide of the present invention, a promoter molecule of choice, including, without limitation, enhancers, and leader sequences, a suitable 3' regulatory region to allow transcription in the host, and any additional desired components, such as reporter or marker genes, are cloned into the vector of choice using standard cloning procedures in the art, such as described in Joseph Sambrook et al., MOLECULAR CLONING: A LABORATORY MANUAL (Cold Springs Harbor 1989); Frederick M. Ausubel, SHORT PROTOCOLS IN MOLECULAR BIOLOGY (Wiley 1999), and U.S. Pat. No. 4,237,224 to Cohen and Boyer, which are hereby incorporated by reference in their entirety.

Once the nucleic acid molecule encoding the peptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by Joseph Sambrook et al., Molecular Cloning: A Laboratory Manual (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purification of peptide produced via recombinant methods may be achieved by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC. Alternatively, the peptide can be isolated without precipitation using affinity chromatography or other chromatographic techniques.

EXAMPLES

The following examples are provided to illustrate embodiments of the present invention but they are by no means intended to limit its scope.

Materials and Methods for Examples 1-6

Proteins:

Human fibronectin was purified as described (Miekka et al., "Rapid Methods for Isolation of Human Plasma Fibronectin," *Thromb Res.* 27:1-14 (1982), which is hereby incorporated by reference in its entirety). Recombinant vitronectin was produced as described (Mercurius et al., "Inhibition of Vascular Smooth Muscle Cell Growth by Inhibition of Fibronectin Matrix Assembly," *Circulation Research* 82:548-556 (1998), which is hereby incorporated by reference in its entirety). Laminin was purchased from BD Biosciences (San Jose, Calif.), collagen type I from UBI (Lake Placid, N.Y.), and fibrinogen from Enzyme Research Laboratories (South Bend, Ind.). pUR4 cDNA was a generous gift from Dr. Hanski, and was provided by Dr. Mosher (University of Wisconsin, Madison, Wis.). pUR4 (also known as FUD, functional upstream domain) is a 49-mer peptide derived from the bacterial F1 adhesin. pUR4 cDNA was modified to remove the coding region for a Cys residue that was present in the N-terminal portion of the peptide. This Cys is not part of the adhesin F1, but was added as a consequence of the original cloning strategy. The sequence of pUR4 is provided in Table 1 supra as SEQ ID NO:1. The control peptide is a His tagged carboxyl terminal fragment (68-mer) of fibronectin's III-11 module (III-11C) and was produced as described (Sottile et al., "Fibronectin Matrix Assembly Enhances Adhesion-Dependent Cell Growth," *J. Cell Sci.* 111:2933-2943 (1998), which is hereby incorporated by reference in its entirety). III-11C has been used in in vivo studies by others (Zhou et al., "Fibronectin Fibrillogenesis Regulates Three-Dimensional Neovessel Formation," *Genes Dev.* 22:1231-1243 (2008); Sottile et al., "Fibronectin Polymerization Regulates the Composition and Stability of Extracellular Matrix Fibrils and Cell-Matrix Adhesions," *Mol. Biol. Cell.* 13:3546-3559 (2002), which are hereby incorporated by reference in their entirety) and has no known biological effects in vitro or in vivo.

Endotoxin was removed from peptides using Detoxi-Gel (Pierce, Rockford, Ill.). Endotoxin levels were measured with a *Limulus amebocyte* lysate assay kit (QCL-1000, Lonza, Basel, Switzerland). Endotoxin levels were less than 0.1 endotoxin units (EU) per mg of peptide.

Enzyme Linked Immunosorbant Assay (ELISA):

96-well tissue culture plates were coated with 10 μg/mL type I collagen, fibronectin, laminin, fibrinogen, or vitronectin overnight at 4° C. Denatured collagens were generated as described (George et al., "Fibronectins are Essential for Heart and Blood Vessel Morphogenesis but are Dispensable for Initial Specification of Precursor Cells," *Blood* 90:3073-3081 (1997), which is hereby incorporated by reference in its entirety). Plates were blocked with 1% bovine serum albumin (BSA) in Tris buffered saline (TBS) for 1 hour, then washed with TBS. pUR4 was serially diluted into coated wells, then incubated at room temperature for 90 min. Wells were washed with TBS containing 0.1% Tween 20. An anti-His antibody (HisG, Invitrogen, Carlsbad, Calif.) that recognizes the His tag on pUR4 was added for 1.5 hour at room temperature. Wells were washed, then incubated with a horseradish peroxidase (HRPO) conjugated secondary antibody. After washing, peroxidase activity was quantified by using 2,2'-azino-bis-(3-ethylbenthiazoline-g-sulfonic acid). Measurements were done at 405 nm on a Wallac 1420 multilabel counter.

Cell Culture:

Rat aortic smooth muscle cells (RASM) were obtained from Cell Applications (San Diego, Calif.) and maintained in serum containing media (Cell Applications). SMC were used at passages 4-6.

Animal Studies:

Both sexes of FVB transgenic mice were used for the carotid ligation experiments, since no significant differences in their modeling response were reported between male and female mice. All procedures were approved by the University of Rochester Animal Care Committee, and were performed in accordance with the guidelines of the National Institutes of Health for the care and use of laboratory animals.

Morphometry:

Digital images of Verhoeff-van Gieson elastic stained cross-sections were captured and morphometric analysis was performed using Image-Pro Plus software (Media Cybernetics, Md.). The circumferences of the lumen, internal elastic lamina (IEL) and external elastic lamina (EEL) in the sections were identified using the automatic trace mode in Image-Pro. The accuracy of the automated tracing was verified by visual inspection of the images. Cross-sectional areas of the lumen, neointima, media, adventitia, and the area encompassed by the EEL were measured. Vessel compartment volumes were calculated as described (Intengan et al., "Vascular Remodeling in Hypertension: Roles of Apoptosis, Inflammation, and Fibrosis," *Hypertension* 38:581-587 (2001), which is hereby incorporated by reference in its entirety). Briefly, starting with the carotid bifurcation as the origin, a series of cross-sections of 5 µm were cut every 200 µm through the first mm length of the carotid artery. Morphometric analysis was performed at each point, and the average of each division was calculated, summed, and reported as the volume.

Immunohistochemistry and Quantitative Analysis:

Sections selected from the first millimeter of the carotid artery in each group were used for immunohistochemistry (IHC). Endogenous peroxidase activity was blocked with 3% $H_2O_2$, followed by incubation with Dako serum-free blocking solution (Dako; Glostrup, Denmark). The primary antibodies used were: polyclonal anti-fibronectin (Chemicon/Millipore, Billerica, Mass.), polyclonal anti-collagen type I (LF-67; a gift from Dr. Fisher, NIH, Bethesda, Md.), monoclonal anti-proliferating cell nuclear antigen (PCNA) (Sigma, St. Louis, Mo.), polyclonal anti-smooth muscle myosin heavy chain (SMMHC) (Biomedical Technologies Inc., Stoughton, Mass.), monoclonal smooth muscle-actin (SM-actin) (Dako), anti-leukocyte common antigen, CD45 (BD Pharmingen, San Jose, Calif.), monoclonal anti-intercellular adhesion molecule-1 (ICAM-1) (BD Pharmingen), and polyclonal anti-vascular cell adhesion molecule-1 (VCAM-1) (Santa Cruz Biotechnology, Santa Cruz, Calif.). Antigen retrieval for anti-fibronectin and anti-collagen type I antibodies was performed by incubating sections with proteinase K in 0.05M Tris-HCL buffer. Antigen retrieval for CD 45 antibody was performed by incubating sections with 10 mM citrate buffer (pH=6) at 120° C. Sections were then incubated with appropriate biotinylated secondary antibodies followed by avidin-biotin immunoperoxidase system (Vector Laboratories, Burlingame, Calif.). Liquid DAB Substrate Chromogen system (Dako) or Vector Red (Vector) was used for detection. PCNA, CD45, ICAM-1, and VCAM-1-immunostained sections were counterstained with hematoxylin.

Quantitative IHC analysis was performed using Image-Pro Plus software. Data from 3-5 mice were averaged, and the average values ±s.e.m. determined. For fibronectin, collagen type I, SMMHC, and SMα-actin, color digital images were captured using a 40× objective and transformed into gray scale. Sixteen fields of view of equal size per section in the media or adventitia were randomly chosen, and the mean of the optical densities from the sixteen fields of view was determined. Three sections were analyzed per animal. For quantitative comparison of leukocyte infiltration and cell adhesion molecule expression, images were acquired using a 60× objective. The CD45, ICAM-1, and VCAM-1-positive areas were obtained using an automated programmed segmentation procedure in ImagePro. The intima plus media or adventitial regions were traced manually. The percent of the positively stained area to the total traced area was determined. For evaluation of proliferating cells, the percent of PCNA (+) cells to total cells was determined by counting cell numbers in PCNA-stained sections that had been counterstained with hematoxylin. The percent positive cells is reported as the proliferation index. To determine the SMC density, sections were stained with hematoxylin, and cells present in the media were counted. The data is expressed as number of cells/$\mu m^2$.

Detection of Peptides in Vessel Wall:

pUR4 and III-11C were conjugated to Texas-Red, as per the manufacturer's instructions (Molecular Probes/Invitrogen). 20 µM Texas-Red (TR) conjugated proteins were embedded in pluronic gel and applied to the vessel following ligation surgery. Mice were sacrificed 1, 3, or 7 days after surgery. Longitudinal frozen sections (20 µm thickness) were cut and immunostained with a polyclonal anti-TR antibody (Molecular Probes/Invitrogen). For quantitatively evaluating the efficacy of peptide delivery to the common carotid artery, 15-18 fields of view in the media from 2-3 mice at each time point were analyzed. The TR (+) areas were quantitated using an automated programmed segmentation procedure in ImagePro. The percentage of TR (+) area to the total medial area was determined.

Quantitative Reverse-Transcription Polymerase Chain Reaction (qRT-PCR).

mRNA was isolated from RASMs 24 hours after incubation with 500 nM pUR4 or III-11C control peptides using RNAzol as per the manufacturer's instructions (Invitrogen). cDNA was prepared using a Superscript First Strand cDNA kit as per the manufacturer's instructions (Invitrogen). Mouse carotid arteries were harvested and frozen in liquid nitrogen. RNA was isolated using Trizol and purified using a QIAgen RNeasy Micro Kit. RNA integrity was examined with an Agilent 2100 Bioanalyser using RNA6000 NanoAssay (Agilent Technology). Whole transcriptome amplification was performed using Qiagen's QuantiTect Whole Transcriptome Amplification Kit. Quantitative RT-PCR analyses were performed using ABI Prism 7900HT sequence detection system (Applied Biosystems). The qRT-PCR primers for 3 mouse genes were obtained from ABI: GADPH (4352932E), fibronectin (Mm01256744_m1), and collagen Ia1 (Mm00801666_g1). TaqMan probe chemistry was used according to the manufacturer's instructions. qRT-PCR reactions were run in triplicate for each sample. The data was normalized to the levels of GAPDH in each sample, and the results were averaged.

Carotid Ligation Surgery:

Blood flow in the left carotid artery of 10-week-old FVB/NJ (FVB) mice was reduced by ligating the external and internal carotid arterial branches as described (Korshunov et al., "Flow-Induced Vascular Remodeling in the Mouse: A Model for Carotid Intima-Media Thickening," *Arterioscler. Thromb. Vasc. Biol.* 23:2185-2191 (2003), which is hereby incorporated by reference in its entirety). Mice were anesthetized with an intraperitoneal injection of ketamine (80 mg/kg) and xylazine (5 mg/kg) as described in the above-cited referenced. The left common carotid artery was dissected free of the surrounding connective tissue and 50 µL of F-127 pluronic gel (BASF) containing 20 µmol/L pUR4 or III-11C was applied around the carotid artery. Animals were separated into 5 groups containing 5 to 10 animals each: (1) sham-operated, in which the branches of the left carotid artery were exposed and dissected out, but not ligated; (2) ligation; (3) ligation with pluronic gel; (4) ligation with pluronic gel containing III-11C; (5) ligation with pluronic gel containing pUR4.

Tissue Collection and Processing:

Blood flow in the left and right common carotid artery was measured using an ultrasonic transit-time volume flowmeter (Transonic Systems) before sacrifice. Animals were perfusion-fixed with 10% formalin 7 or 14 days after surgery. The common carotid arteries were harvested and embedded in paraffin. Cross-sections of 5 μm were cut from the bifurcation every 200 μm through the first mm length of the carotid artery as described (Korshunov et al., "Flow-Induced Vascular Remodeling in the Mouse: a Model for Carotid Intima-Media Thickening," *Arterioscler. Thromb. Vasc. Biol.* 23:2185-2191 (2003), which is hereby incorporated by reference in its entirety). Sections were stained with Verhoeff-van Gieson elastic stain, and then subjected to morphometric analysis.

Statistical Analysis:

For animal studies, data are presented as the mean±s.e.m. Comparisons were made with an unpaired, 2-tailed Student's t test, or one-way ANOVA with GraphPad Prism software (San Diego, Calif.). A difference between the means was considered significant when $p<0.05$.

Example 1

Peptide pUR4 Blocks In Vitro Fibronectin and Collagen Deposition in SMCs

Figure 7:
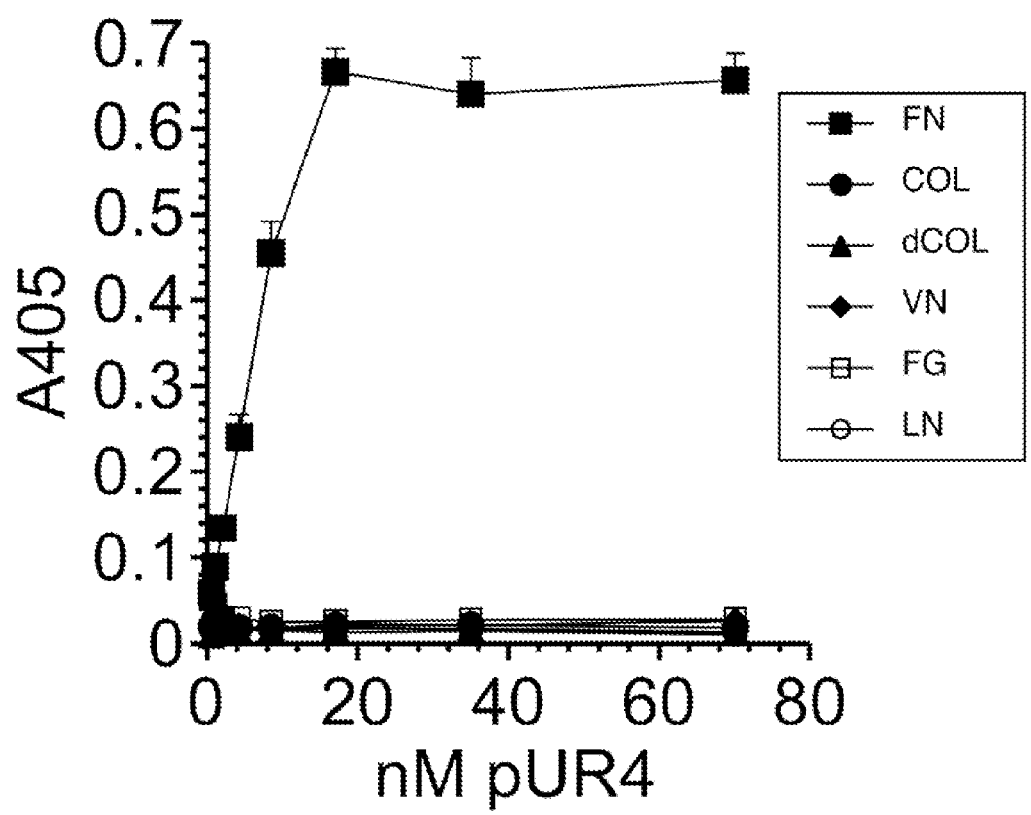
FIG. 7 is a graph depicting the binding of pUR4 to ECM Proteins. 96-well plates were coated with 10 µg/mL type I collagen (COL), denatured type I collagen (dCOL), fibronectin (FN), laminin (LN), vitronectin (VN), or fibrinogen (FG) at 4° C. overnight. pUR4 was added to the wells and serially diluted. Bound pUR4 was detected as described herein. Measurements were done at 405 nm on a Wallac 1420 multilabel counter. Data represents the average of duplicate determinations, and the error bars the range.

The ability of pUR4 to inhibit SMCs deposition of fibronectin and collage was investigated. pUR4 has been shown to inhibit fibronectin polymerization in vitro in fibroblasts, osteosarcoma cells, and endothelial cells, but it was not known whether this peptide would have any effect on SMCs (Zhou et al., "Fibronectin Fibrillogenesis Regulates Three-Dimensional Neovessel Formation," *Genes Dev.* 22:1231-1243 (2008); Tomasini-Johansson et al., "Peptide from Adhesin F1 Inhibits Fibronectin Matrix Assembly," *J. Biol. Chem.* 276:23430-23439 (2001), which are hereby incorporated by reference in their entirety). As shown in FIG. 1D, when compared to 1A, addition of pUR4 to cultured SMCs inhibited the deposition of endogenous fibronectin into the ECM. Previous data has shown that fibronectin regulates the deposition of other proteins into the ECM, including type I collagen (Sottile et al., "Fibronectin Polymerization Regulates the Composition and Stability of Extracellular Matrix Fibrils and Cell-Matrix Adhesions," *Mol. Biol. Cell.* 13:3546-3559 (2002), which is hereby incorporated by reference in its entirety). When SMCs were cultured in the presence of pUR4, deposition of endogenous collagen I into matrix fibrils was also inhibited (FIG. 1E; compare FIG. 1B). The control peptide had no effect on fibronectin or collagen I deposition (FIGS. 1G and 1H). pUR4 binds to fibronectin, (Ensenberger et al., "Specific Interactions Between F1 Adhesin of *Streptococcus Pyogenes* and N-Terminal Modules of Fibronectin," *J. Biol. Chem.* 276:35606-35613 (2001), which is hereby incorporated by reference in its entirety) and inhibits fibronectin deposition by interfering with the binding of fibronectin to matrix assembly sites on the cell surface (Tomasini-Johansson et al., "Peptide from Adhesin F1 Inhibits Fibronectin Matrix Assembly," *J. Biol. Chem.* 276:23430-23439 (2001), which is hereby incorporated by reference in its entirety). pUR4 does not inhibit cell spreading or adhesion to collagen or fibronectin (Tomasini-Johansson et al., "Peptide from Adhesin F1 Inhibits Fibronectin Matrix Assembly," *J. Biol. Chem.* 276:23430-23439 (2001), which is hereby incorporated by reference in its entirety) and does not bind to other ECM proteins, including collagen I, fibrinogen, and laminin (FIG. 7). In addition, pUR4 does not inhibit fibronectin or collagen mRNA synthesis in SMCs (Table 2). However, there was a trend toward decreased fibronectin and collagen I mRNA in the carotid artery of animals treated with pUR4 in comparison with control peptide-treated animals (Table 3).

TABLE 2 qRT-PCR of Fibronectin and Collagen I in SMC

| Sample | Treatment | Fibronectin | Col Ia1 |
|---|---|---|---|
| SMC | PBS | 1.00 ± 0.28 | 1.00 ± 0.08 |
|  | 111-11C | 1.16 ± 0.12 | 1.27 ± 0.13 |
|  | pUR4 | 1.43 ± 0.02 | 1.42 ± 0.06 |

Confluent cultures of rat aortic SMCs were incubated in the presence of 500 nM pUR4, control III-11C peptide or an equivalent volume of PBS for 24 h. qRT-PCR was performed in triplicate for each sample using TaqMan chemistry as described supra. Data represent the average of duplicate samples, and the error bars the range. The relative levels of fibronectin and collagen are shown; the PBS control was set equal to 1.

TABLE 3 qRT-PCR of Fibronectin and Collagen I in Carotid Arteries

| Sample | Treatment | Fibronectin | | Col Ia1 | |
|---|---|---|---|---|---|
|  |  | Day 4 | Day 7 | Day 4 | Day 7 |
| Carotid Arteries | 111-11C | 1.00 ± 0.34 | 1.00 ± 0.09 | 1.00 ± 0.32 | 1.00 ± 0.16 |
|  | pUR4 | 0.70 ± 0.23 | 0.41 ± 0.23 | 0.60 ± 0.30 | 0.58 ± 0.36 |

Mouse carotid arteries were harvested from pUR4 and III-11C treated animals 4 or 7 days post surgery. qRT-PCR was performed as described supra. qRT-PCR reactions were run in triplicate for each arterial sample. Three arteries were analyzed for each condition. The data represent the average of these 3 samples, and the error bars the s.e.m. The relative levels of fibronectin and collagen are shown; III-11C was set equal to 1. A two tailed homoscedastic (two sample equal variance) t test was used to analyze the data. No statistically significant differences ($p < 0.05$) were found between the groups.

Example 2

Peptide pUR4 Blocks Vascular Remodeling

Figures 8A, 8B, 8C, 8D, 8E:
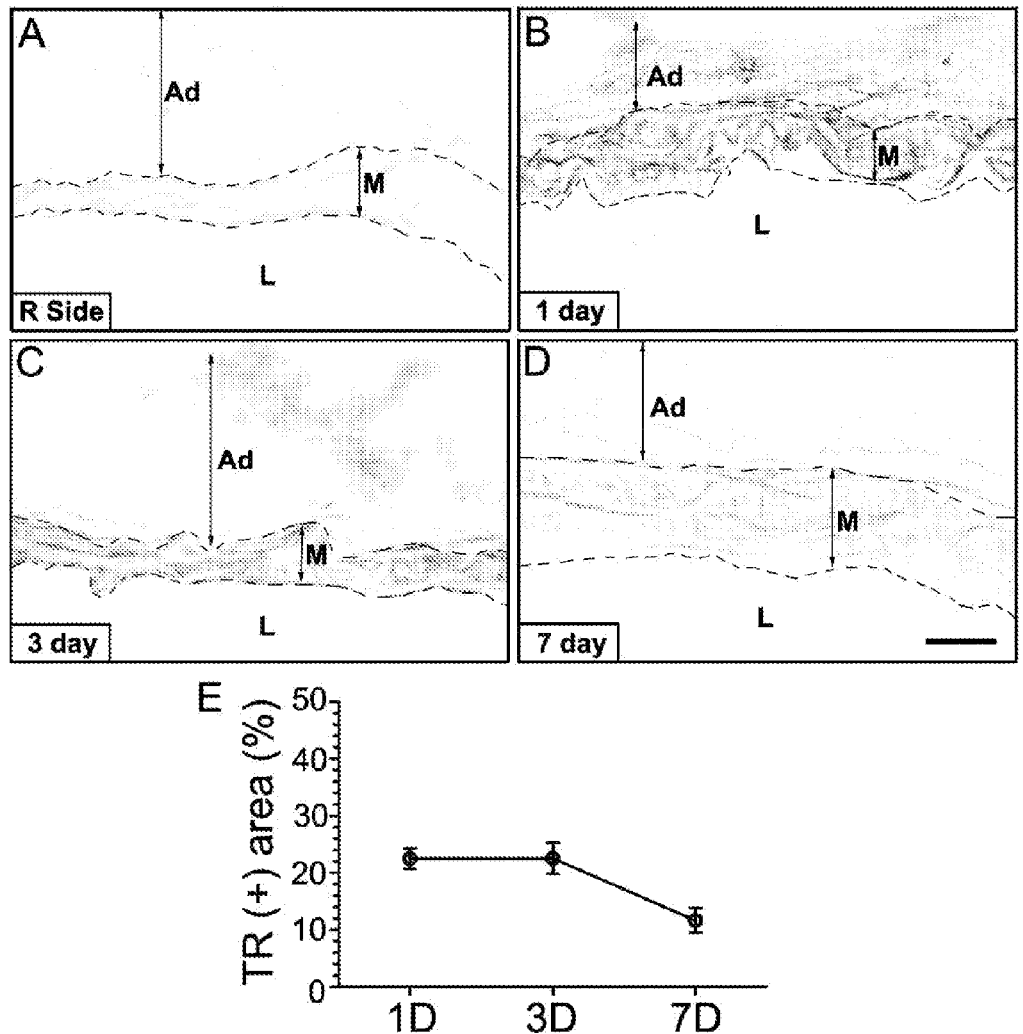
FIGS. 8A-8E provide visualization of pUR4 in the vessel wall. Texas-Red (TR) conjugated pUR4 (20 µM) was embedded in pluronic gel and periadventitially delivered to the left carotid artery following ligation surgery as described infra. The right carotid artery from the same animal was used as a control. Mice were sacrificed 1, 3, and 7 days after surgery, and the carotid arteries were harvested and flash frozen. Longitudinal sections (20 µm) were immunostained with an anti-TR antibody. Representative images from the right common carotid artery (FIG. 8A), and left common carotid artery of 1 day (FIG. 8B), 3 day (FIG. 8C), and 7 day (FIG. 8D) animals are shown. The percentage area which is TR (+) (FIG. 8E) was assessed in the media of the vessels. Media=M; adventitia=Ad; lumen=L. Bar, 20 µm.

Fibronectin is known to affect SMC growth, migration, and differentiation in vitro (Mercurius et al., "Inhibition of Vascular Smooth Muscle Cell Growth by Inhibition of Fibronectin Matrix Assembly," *Circulation Research* 82:548-556 (1998); DiMilla et al., "Maximal Migration of Human Smooth Muscle Cells on Fibronectin and Type IV Collagen Occurs at an Intermediate Attachment Strength," *J. Cell. Biol.* 122:729-737 (1993); String a et al., "Role of Newly Synthesized Fibronectin in Vascular Smooth Muscle Cell Migration on Matrix-Metalloproteinase-Degraded Collagen," *Biochem. Soc. Trans.* 30:102-111 (2002); Hedin et al., "Diverse Effects of Fibronectin and Laminin on Phenotypic Properties of Cultured Arterial Smooth Muscle Cells," *J. Cell. Biol.* 107:307-319 (1988), which are hereby incorporated by reference in their entirety). Hence, fibronectin could promote vascular remodeling by multiple mechanisms. To determine whether peptide pUR4 blocks intima-media thickening (IMT), a flow-induced model of vascular remodeling was used in which the internal and external branches of the common carotid artery are ligated (Korshunov et al., "Flow-Induced Vascular Remodeling in the Mouse: a Model for Carotid Intima-Media Thickening," *Arterioscler. Thromb. Vasc. Biol.* 23:2185-2191 (2003); Korshunov et al., "Strain-Dependent Vascular Remodeling: the "Glagov Phenomenon" is Genetically Determined," *Circulation* 110:220-226 (2004), which are hereby incorporated by reference in their entirety). Blood flow in the common carotid artery was significantly reduced after ligation (0.13±0.01 mL/min) compared to shams (0.59±0.07 mL/min). There were no differences among experimental groups treated with pluronic gel. After ligation of the carotid artery, pUR4 and the control peptide were embedded in pluronic gel, and applied periadventitially. FIGS. 8A-8D demonstrate that the pUR4 peptide can be readily detected in the vessel wall in both the media and adventitia 1 to 3 days after periadventitial application. The levels of the peptide were significantly reduced by day 7 (FIG. 8E). The control peptide could also be detected in the vessel wall.

Figures 2A, 2B, 2C, 2D, 2E:
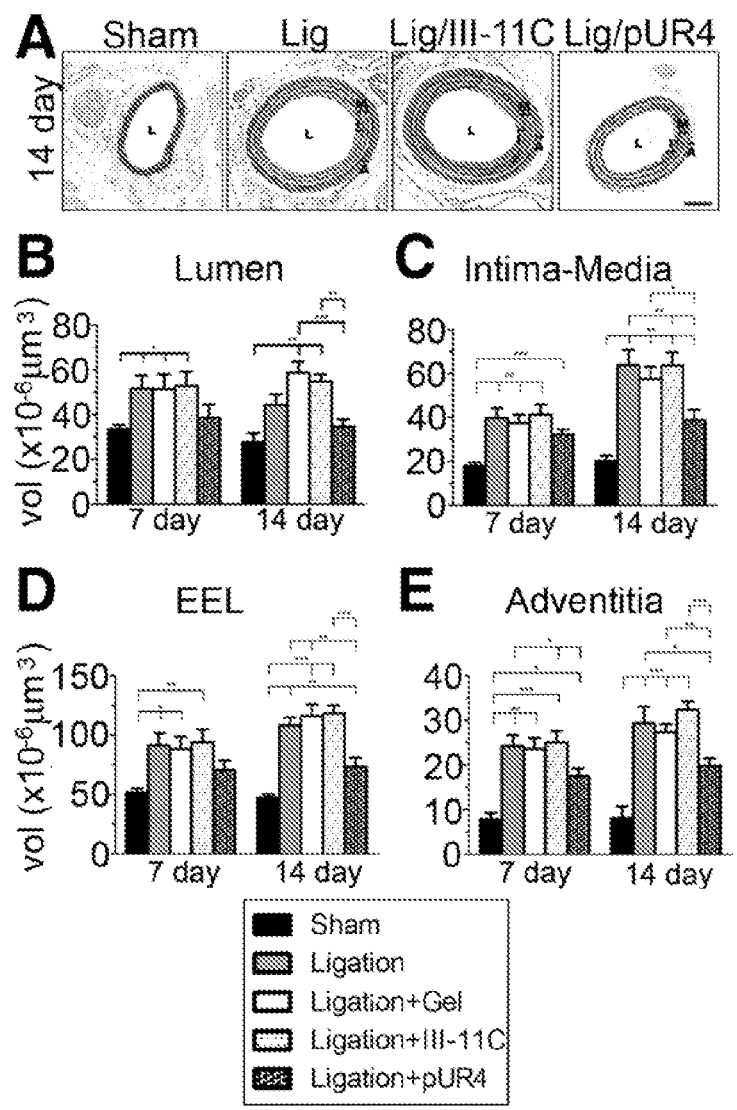
FIGS. 2A-2E show that the pUR4 fibronectin inhibitor decreases vascular remodeling in the carotid artery.
Figures 9A, 9B:
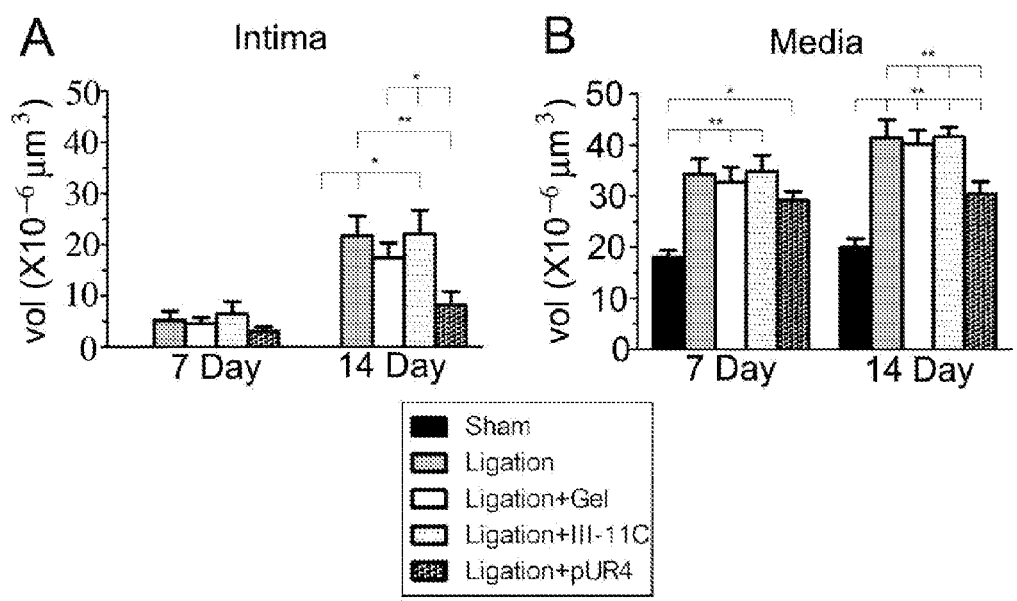
FIGS. 9A-9B show pUR4 decreases intima and media thickening. Morphometric analysis of the intima (FIG. 9A) and media (FIG. 9B) 7 and 14 days after ligation. * indicates $p<0.05$, and ** indicates $p<0.01$.

FVB mice exhibited significant IMT 14 days after ligation (compare sham versus ligated; FIG. 2A) (Korshunov et al., "Strain-Dependent Vascular Remodeling: the "Glagov Phenomenon" is Genetically Determined," *Circulation* 110:220-226 (2004); Korshunov et al., "Plasminogen Activator Expression Correlates with Genetic Differences in Vascular Remodeling," *J. Vasc. Res.* 41:481-490 (2004), which are hereby incorporated by reference in their entirety). Application of pluronic gel in the absence or presence of the control peptide had no effect on vascular remodeling. Periadventitial administration of pUR4, but not the control peptide, dramatically reduced carotid remodeling (FIG. 2A). Morphometry of the carotid compartment was performed 7 and 14 days after ligation (FIG. 2B-2E). Lumen volume was significantly increased after ligation in control peptide-treated mice in comparison to shams (FIG. 2B), consistent with published data in FVB mice (Korshunov et al., "Strain-Dependent Vascular Remodeling: the "Glagov Phenomenon" is Genetically Determined," *Circulation* 110:220-226 (2004), which is hereby incorporated by reference in its entirety). This increase was prevented by pUR4 treatment. There was a dramatic effect of pUR4 on vascular wall remodeling (FIG. 2C-2E). Ligation of the carotid artery resulted in a 3-fold increase in intima-media volume at 14 days (FIG. 2C). The pUR4 peptide reduced the extent of IMT by 40% in comparison with control peptide-treated animals at 14 days (FIG. 2C). When vessel compartments were analyzed separately (FIGS. 9A-9B), pUR4 was found to reduce intima thickening by 63%, and media thickening by 27%. Interestingly, there was no statistical effect of pUR4 on IMT at 7 days. The reduction of IMT by pUR4 at 14 days was attributable to prevention of both intimal and medial thickening compared to 7 day changes in control peptide treated animals (FIGS. 9A-9B). Similarly, pUR4 inhibited adventitial thickening by 38% compared to III-11C at 14 days (FIG. 2E). Finally, pUR4 treatment prevented outward remodeling over the time course, as there was no difference in EEL volume between pUR4 and shams 7 days post ligation (FIG. 2D). However, the remodeling index was not different between pUR4 and III-11C. These data are the first to demonstrate that fibronectin is an important regulator of vascular remodeling in vivo.

Example 3

Peptide pUR4 Decreases ECM Accumulation

Figures 3A, 3B, 3C, 3D, 3E:
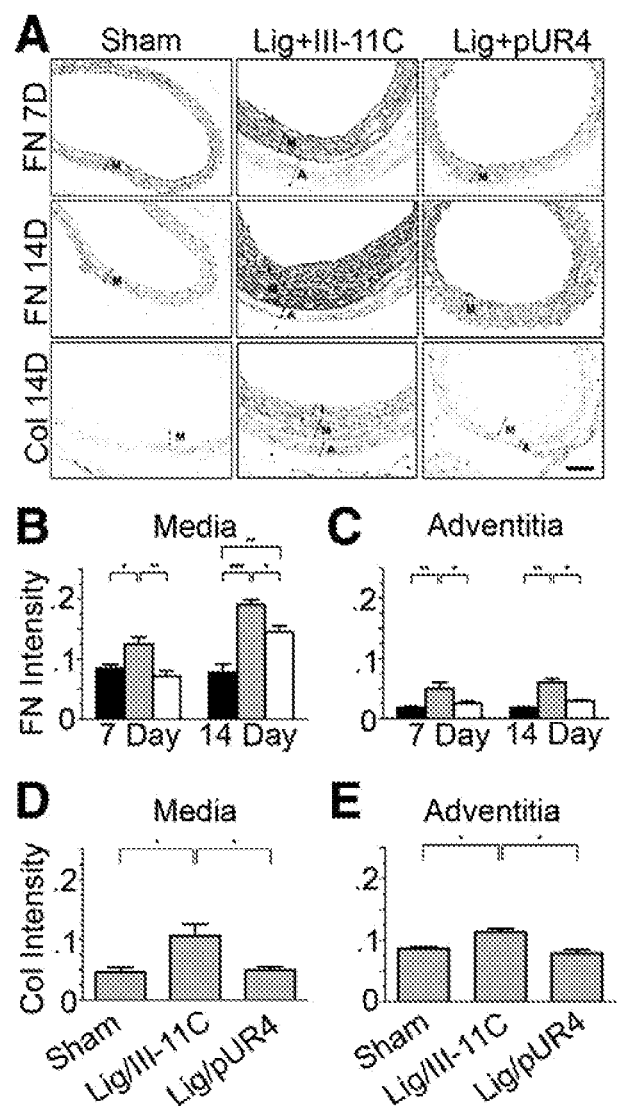
FIGS. 3A-3E demonstrate pUR4 mediated decrease in fibronectin and collagen I deposition in the left carotid artery after ligation.

Immunohistochemistry (IHC) was used to determine whether pUR4 caused a reduction in fibronectin and collagen I deposition in the left carotid artery. IHC analysis indicates that there was a dramatic reduction in the accumulation of collagen I and fibronectin in the media and adventitia 7 and 14 days after surgery in pUR4 treated animals in comparison with control animals (FIG. 3A). At 7 days after surgery, pUR4 totally prevented increased fibronectin deposition (FIGS. 3B and 3C). At 14 days after surgery, fibronectin and collagen levels were still decreased in pUR4-treated animals in comparison to control peptide-treated animals. The decrease in collagen deposition parallels the decrease in fibronectin deposition (FIGS. 3D and 3E).

Example 4

Peptide pUR4 Decreases SMC Phenotypic Modulation

Figures 4A, 4B, 4C:
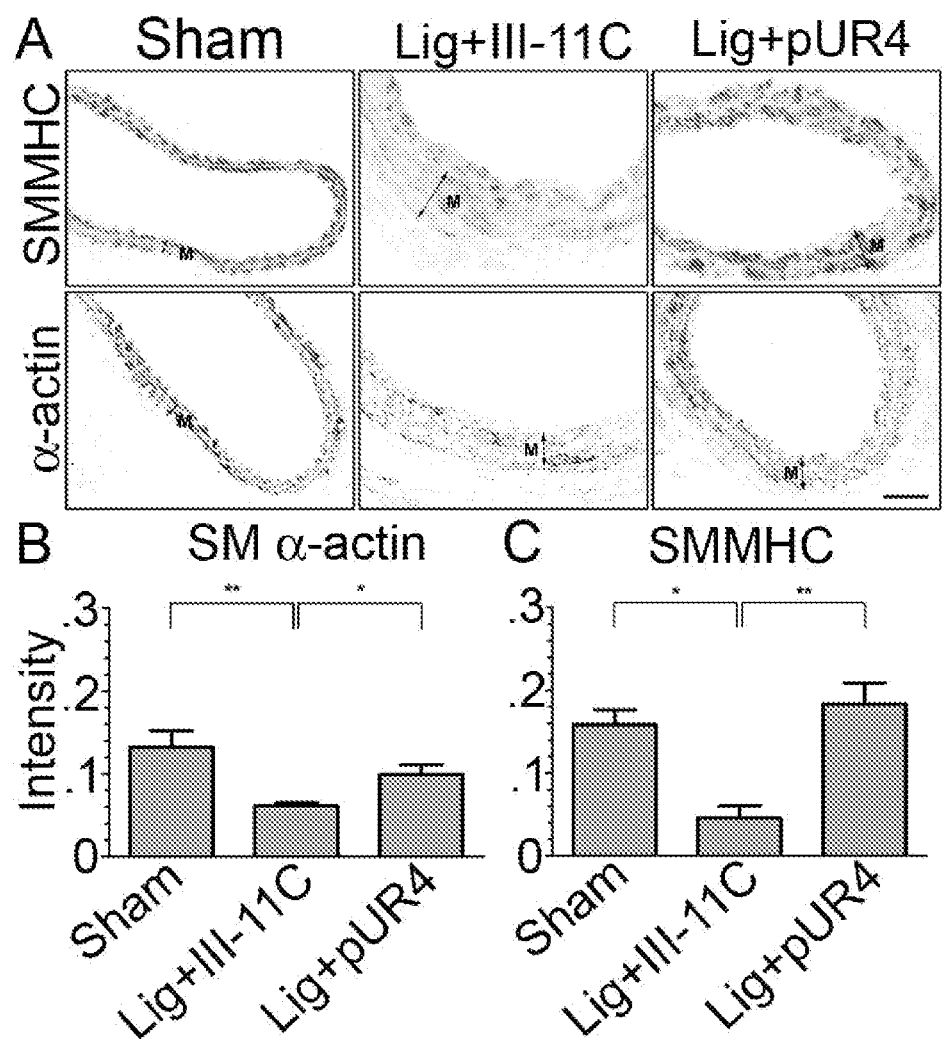
FIGS. 4A-4C shows pUR4 treatment maintains smooth muscle cell (SMC) differentiation.

To begin to define the mechanism(s) by which fibronectin regulates vascular remodeling, carotid artery sections were analyzed by IHC to determine the effect of pUR4 on SMC differentiation, cell proliferation, and leukocyte infiltration. Arterial injury is known to decrease SMC differentiation markers at early times after injury or in response to decreased blood flow (Owens, G. K., "Regulation of Differentiation of Vascular Smooth Muscle Cells," *Physiol. Rev.* 75:487-517 (1995); Kumar et al., "Remodeling with Neointima Formation in the Mouse Carotid Artery after Cessation of Blood Flow," *Arterioscler. Thromb. Vasc. Biol.* 17:2238-2244 (1997), which are hereby incorporated by reference in their entirety). This decline in SMC differentiation is thought to contribute to increased SMC migration and proliferation. The quantitative data show that reduced flow in the left carotid artery results in decreased SMC α-actin and SM myosin heavy chain staining after treatment with III-11C peptide (FIG. 4B-4C). However, peptide pUR4 prevented SMC dedifferentiation, as evidenced by the maintenance of SM α-actin and SM myosin heavy chain staining in the media (FIG. 4B-4C).

Example 5

Peptide pUR4 Decreases Cell Proliferation

Figures 5A, 5B, 5C, 5D:
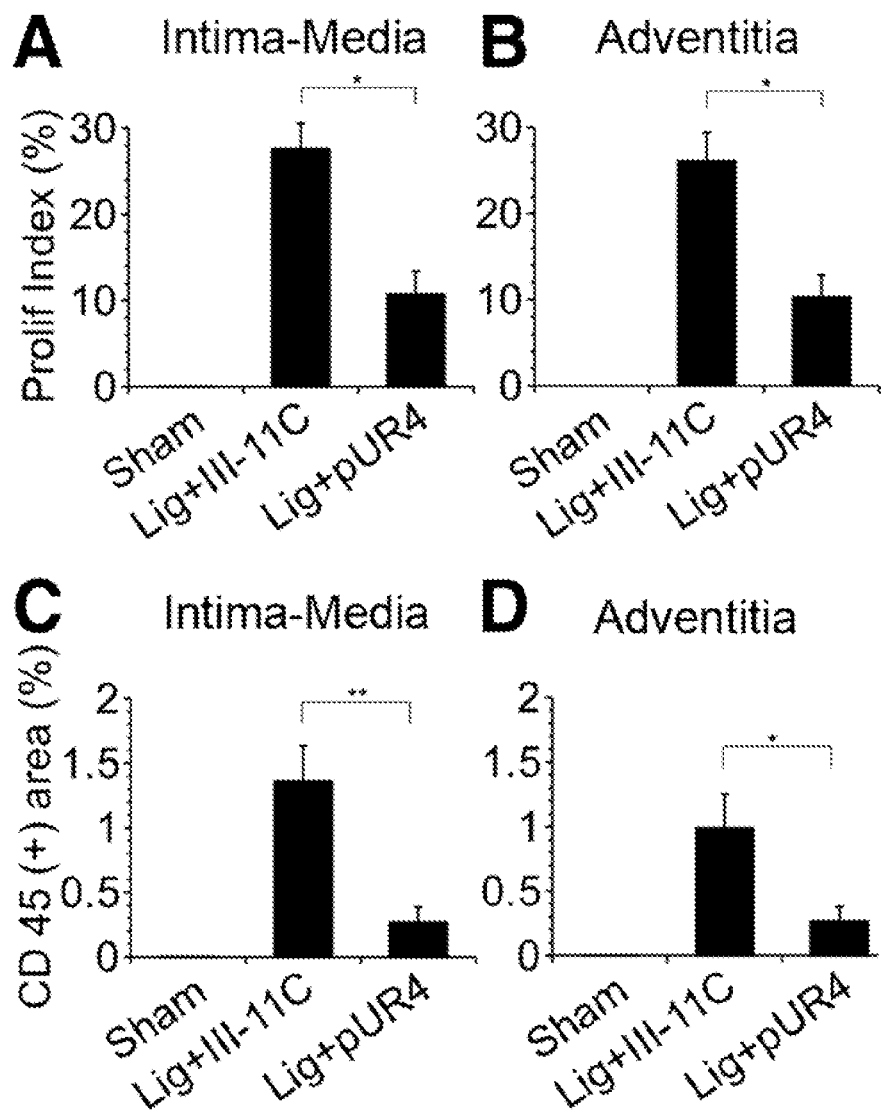
FIGS. 5A-5D show the pUR4 mediated decrease in cell proliferation and leukocyte infiltration in the left carotid artery. Sections of the left carotid artery from animals 7 days post ligation were stained for PCNA and counterstained with hematoxylin to assess cell proliferation.
Figures 6A, 6B:
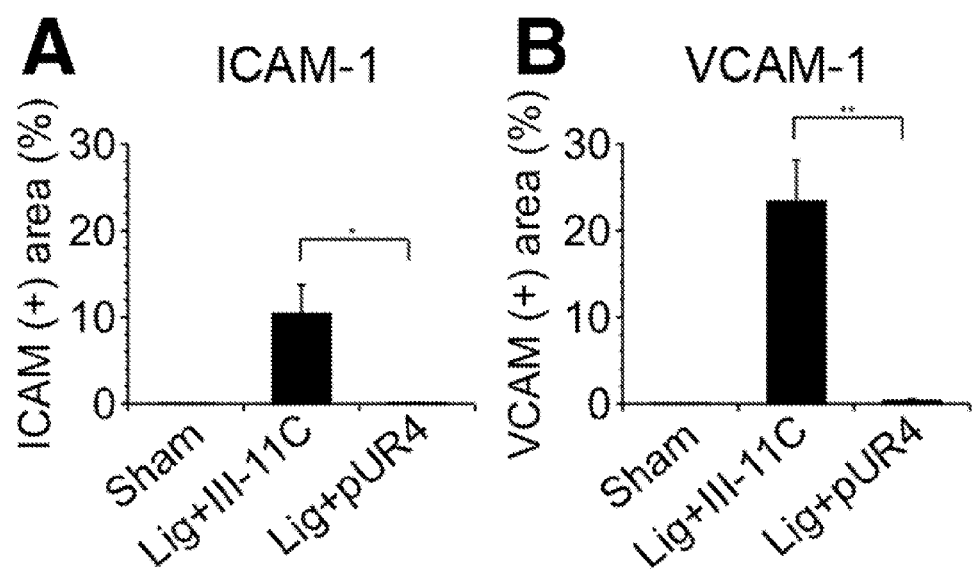
FIGS. 6A-6B show the pUR4 mediated decrease in ICAM-1 and VCAM-1 levels. Sections of the left carotid artery from animals 7 days after ligation were stained with ICAM-1 or VCAM-1. Percentage of the intima-media area which was ICAM-1 (+) (FIG. 6A) or VCAM-1 (+) (FIG. 6B) was evaluated in the intima-media of the vessels. * indicates $p<0.05$, ** indicates $p<0.01$.
Figures 10A, 10B, 10C:
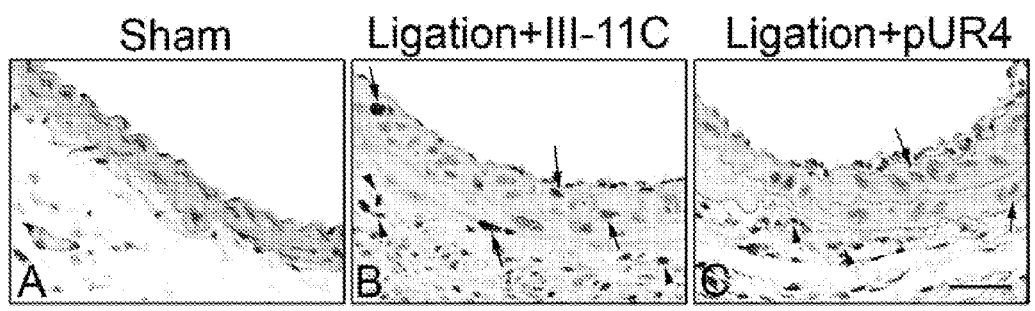
FIGS. 10A-10C depict pUR4 mediated decrease in cell proliferation in the carotid artery. Sections of the left carotid artery were stained with antibodies to PCNA seven days post ligation. Sections were counterstained with hematoxylin. Representative photomicrographs of PCNA stained sections from sham-operated animals (FIG. 10A), ligated animals with III-11C treatment (FIG. 10B), and ligated animals with pUR4 treatment (FIG. 10C). Arrows indicate PCNA (+) cells in the media, and arrowheads indicate PCNA (+) cells in the adventitia. Bar, 50 µm.
Figures 11A, 11B, 11C, 11D, 11E:
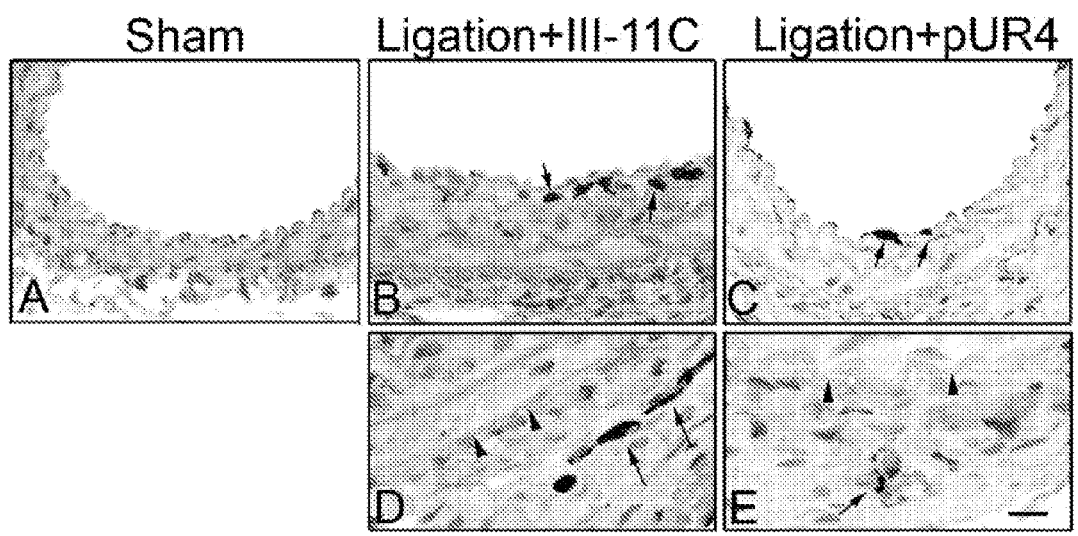
FIGS. 11A-11E show pUR4 mediated decrease in leukocyte infiltration into the vessel. Sections of the left carotid artery were stained with antibodies to CD45 seven days after ligation and counterstained with hematoxylin. Representative photomicrographs of CD45 (+) staining in the media (FIGS. 11A, 11B, and 11C) and adventitia (FIGS. 11D and 11E) of the carotid artery from sham-operated animals (FIG. 11A), ligated animals with III-11C treatment (FIGS. 11B and 11D), and ligated animals with pUR4 treatment (FIGS. 11C and 11E). Arrows indicate CD45 (+) cells in the media and adventitia. Arrowheads indicate the location of the external elastic lamina. Bar, 25 µm in (FIGS. 11A-11C) and 12.5 µm in (FIGS. 11D and 11E).
Figures 12A, 12B, 12C, 12D, 12E, 12F:
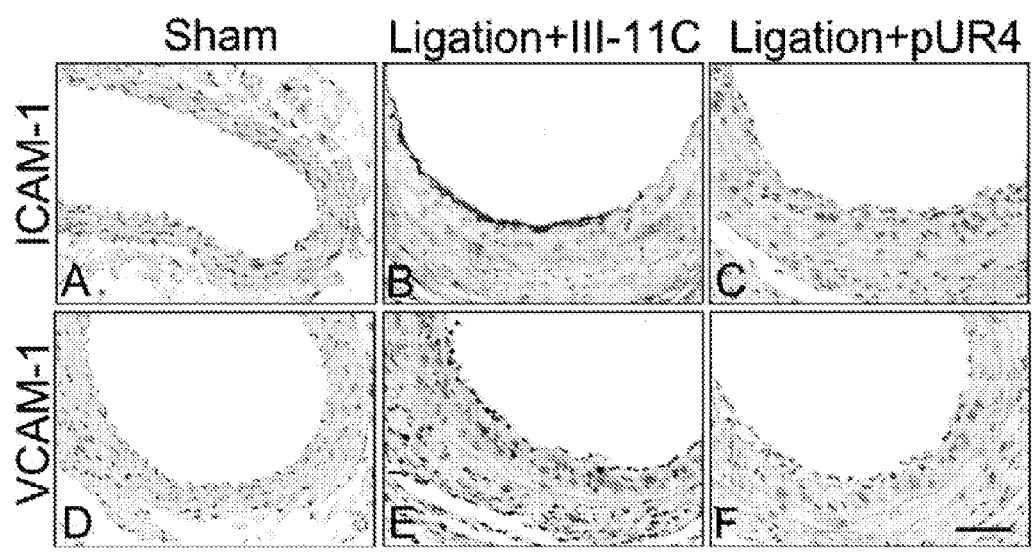
FIGS. 12A-12F show pUR4 mediated decrease in ICAM-1 and VCAM-1 levels. Sections of the left carotid artery were stained with antibodies to ICAM-1 (FIG. 12A-12C) or VCAM-1 (FIGS. 12D-12F) seven days after ligation. Sections were counterstained with hematoxylin. Representative photomicrographs of sections from sham-operated animals (FIGS. 12A and 12D), ligated animals with III-11C treatment (FIGS. 12B and 12E), and ligated animals with pUR4 treatment (FIGS. 12C and 12F). Bar, 20 µm.

Previous data with FVB mice showed that the greatest increase in cell proliferation and leukocyte infiltration was at 7 days post-ligation (Korshunov et al., "Plasminogen Activator Expression Correlates with Genetic Differences in Vascular Remodeling," *J. Vasc. Res.* 41:481-490 (2004), which is hereby incorporated by reference in its entirety). The data herein show that ligation resulted in a significant increase in cell density in the media 7 days after surgery ($6.7 \times 10^{-3}$ cells/$mm^2$ in ligated animals versus $5.0 \times 10^{-3}$ versus cells/$mm^2$ in sham operated animals). pUR4 treatment prevented this increase in cell density by 75% ($5.3 \times 10^{-3}$ cells/$mm^2$). Further, ligation of the left carotid artery increased cell proliferation in the vessel wall as shown by PCNA staining (FIGS. 10A-10C); this increase in cell proliferation was drastically reduced in pUR4-treated animals. There was a significant reduction in cell proliferation in the intima-media (70%) and adventitia (61%) in animals treated with pUR4 (FIGS. 5A and 5B). These data indicate that fibronectin promotes vascular remodeling, in part, by enhancing cell proliferation.

Example 6

Peptide pUR4 Dramatically Reduces Accumulation of Inflammatory Cells in the Carotid Artery Inflammation plays a prominent role in vascular remodeling after injury. Flow-induced vascular remodeling is also accompanied by an increase in inflammatory cells in the vessel wall (Kumar et al., "Remodeling with Neointima Formation in the Mouse Carotid Artery after Cessation of Blood Flow," *Arterioscler. Thromb. Vasc. Biol.* 17:2238-2244 (1997); Korshunov et al., "Plasminogen Activator Expression Correlates with Genetic Differences in Vascular Remodeling," *J. Vasc. Res.* 41:481-490 (2004), which are hereby incorporated by reference in their entirety). The data show that reduced flow in the left carotid artery resulted in an increase in leukocyte numbers in the intima, media, and adventitia 7 days after surgery (FIGS. 5C and 5D, and FIGS. 11A-11E). Inhibition of fibronectin polymerization significantly decreased (80%) leukocyte infiltration into the intima, media, and adventitia (FIGS. 5C and 5D). Further, pUR4 caused a dramatic decrease in adhesion molecule expression, as shown by the reduction in intercellular adhesion molecule-1 (ICAM-1) and vascular cell adhesion molecule-1 (VCAM-1) levels in the vessel wall (FIGS. 6A-6B, FIGS. 12A-12F). These data are the first to demonstrate that fibronectin plays a critical role in regulating the inflammatory response during vascular remodeling.

Discussion of Examples 1-6

Examples 1-6 show that periadventitial delivery of the peptide pUR4 reduces IMT in response to reduced blood flow (FIG. 2), and reduced fibronectin and collagen I accumulation in the vessel wall (FIG. 3). Treatment with pUR4 also resulted in a dramatic decrease in leukocyte infiltration into the vessel wall (FIG. 5), reduced ICAM-1 and VCAM-1 levels (FIGS. 6A-B), inhibited cell proliferation (FIG. 5), and prevented SMC phenotypic modulation (FIG. 4). These data are the first to show that fibronectin is an important regulator of flow induced vascular remodeling in vivo.

Fibronectin is a secreted protein that is polymerized into ECM fibrils by a cell-dependent process (McKeown-Longo et al., "Interaction of the 70,000-mol-wt Amino-Terminal Fragment of Fibronectin with the Matrix-Assembly Receptor of Fibroblasts," *J. Cell. Biol.* 100:364-374 (1985), which is hereby incorporated by reference in its entirety). There is a large literature demonstrating the importance of ECM proteins, including fibronectin and collagen, in regulating cell migration, growth, and differentiation (Koyama et al., "Fibrillar Collagen Inhibits Arterial Smooth Muscle Proliferation Through Regulation of cdk2 Inhibitors," *Cell* 87:1069-1078 (1996); Mercurius et al., "Inhibition of Vascular Smooth Muscle Cell Growth by Inhibition of Fibronectin Matrix Assembly," *Circulation Research* 82:548-556 (1998); Bourdoulous et al., "Fibronectin Matrix Regulates Activation of RHO and CDC42 GTPases and Cell Cycle Progression," *J. Cell Biol.* 143:267-276 (1998); Sottile et al., "Fibronectin Matrix Assembly Enhances Adhesion-Dependent Cell Growth," *J. Cell Sci.* 111:2933-2943 (1998); Rocnik et al., "Evidence for a Role of Collagen Synthesis in Arterial Smooth Muscle Cell Migration," *J. Clin. Invest.* 101:1889-1898 (1998), which are hereby incorporated by reference in their entirety). However, to date, in vivo evidence that fibronectin or fibronectin polymerization regulate SMC function or ECM remodeling has been lacking. Further, the ECM polymerized form of fibronectin has been shown to have distinct effects on cell behavior in comparison to protomeric fibronectin (Mercurius et al., "Inhibition of Vascular Smooth Muscle Cell Growth by Inhibition of Fibronectin Matrix Assembly," *Circulation Research* 82:548-556 (1998); Bourdoulous et al., "Fibronectin Matrix Regulates Activation of RHO and CDC42 GTPases and Cell Cycle Progression," *J. Cell Biol.* 143:267-276 (1998); Sottile et al., "Fibronectin Matrix Assembly Enhances Adhesion-Dependent Cell Growth," *J. Cell Sci.* 111:2933-2943 (1998); Sottile et al., "Fibronectin-Dependent Collagen I Deposition Modulates the Cell Response to Fibronectin," *Am. J. Physiol. Cell Physiol.* 293:C1934-1946 (2007); Hocking et al., "Fibronectin Matrix Polymerization Regulates Small Airway Epithelial Cell Migration," *Am. J. Physiol.* 285:L169-179 (2003); Sechler et al., "Control of Cell Cycle Progression by Fibronectin Matrix Architecture," *J. Biol. Chem.* 273:25533-25536 (1998), which are hereby incorporated by reference in their entirety). Similarly, polymerized collagen I has distinct effects on SMC growth in comparison to nonpolymerized collagen.

In these preceding Examples, peptide pUR4 was used to inhibit fibronectin polymerization in vivo to determine the role of fibronectin matrix deposition in vascular remodeling. pUR4 can inhibit the polymerization of both endogenously produced (FIG. 1) and exogenously supplied fibronectin into the ECM (Tomasini-Johansson et al., "Peptide from Adhesin F1 Inhibits Fibronectin Matrix Assembly," *J. Biol. Chem.* 276:23430-23439 (2001), which is hereby incorporated by reference in its entirety). pUR4 did not decrease fibronectin or collagen I mRNA production in cultured SMC (Table 2). However, there was a trend toward decreased fibronectin and collagen I mRNA in the carotid artery of animals treated with pUR4 in comparison with control peptide-treated animals (Table 3). Because pUR4 does not decrease fibronectin or collagen I mRNA in vitro, it is likely that the unexpected effect of pUR4 on mRNA levels in vivo is indirect, perhaps resulting from altered cytokine production.

Fibronectin matrix has the potential to influence multiple cell properties. Fibronectin can promote SMC growth and migration in vitro (Mercurius et al., "Inhibition of Vascular Smooth Muscle Cell Growth by Inhibition of Fibronectin Matrix Assembly," *Circulation Research* 82:548-556 (1998); DiMilla et al., "Maximal Migration of Human Smooth Muscle Cells on Fibronectin and Type IV Collagen Occurs at an Intermediate Attachment Strength," *J. Cell. Biol.* 122:729-737 (1993); String a et al., "Role of Newly Synthesized Fibronectin in Vascular Smooth Muscle Cell Migration on Matrix-Metalloproteinase-Degraded Collagen," *Biochem. Soc. Trans.* 30:102-111 (2002), which are hereby incorporated by reference in their entirety). Further, fibronectin matrix deposition regulates the deposition and stability of other ECM proteins (Sottile et al., "Fibronectin Polymerization Regulates the Composition and Stability of Extracellular Matrix Fibrils and Cell-Matrix Adhesions," *Mol. Biol. Cell.* 13:3546-3559 (2002); Sottile et al., "Fibronectin-Dependent Collagen I Deposition Modulates the Cell Response to Fibronectin," *Am. J. Physiol. Cell Physiol.* 293:C1934-1946 (2007); Velling et al., "Polymerization of Type I and III Collagens is Dependent on Fibronectin and Enhanced by Integrins Alpha 11Beta 1 and Alpha 2Beta 1," *J. Biol. Chem.* 277:37377-37381 (2002); Kinsey et al., "Fibrillin-1 Microfibril Deposition is Dependent on Fibronectin Assembly," *J. Cell. Sci.* 121:2696-2704 (2008), which are hereby incorporated by reference in their entirety). The data herein show that pUR4 causes a significant reduction in cell proliferation.

Inflammation has also been shown to play an important role in vascular remodeling in response to changes in flow (Furukawa et al., "Anti-Monocyte Chemoattractant Protein-1/Monocyte Chemotactic and Activating Factor Antibody Inhibits Neointimal Hyperplasia in Injured Rat Carotid Arteries," *Circ. Res.* 84:306-314 (1999), which is hereby incorporated by reference in its entirety). The data show that fibronectin plays an important role in regulating the recruitment of leukocytes into the vessel wall (FIG. 5). Fibronectin fragments are known to be chemotactic for neutrophils and monocytes (Hynes, R. O., "Fibronectins," New York: Springer-Verlag; 1990; Clark et al., "Cryptic Chemotactic Activity of Fibronectin for Human Monocytes Resides in the 120-kDa Fibroblastic Cell-Binding Fragment," *J. Biol.*

Chem. 263:12115-12123 (1988); Norris et al., "Fibronectin Fragment(s) are Chemotactic for Human Peripheral Blood Monocytes," J. Immunol. 129:1612-1618 (1982), which are hereby incorporated by reference in their entirety). However, most in vitro data suggest that intact fibronectin does not promote leukocyte chemotaxis (Hynes, R. O., *Fibronectins*, (Springer-Verlag 1990); Clark et al., "Cryptic Chemotactic Activity of Fibronectin for Human Monocytes Resides in the 120-kDa Fibroblastic Cell-Binding Fragment," *J. Biol. Chem.* 263:12115-12123 (1988); Norris et al., "Fibronectin Fragment(s) are Chemotactic for Human Peripheral Blood Monocytes," *J. Immunol.* 129:1612-1618 (1982), which are hereby incorporated by reference in their entirety). The data in FIGS. 6 and 12 also show that peptide pUR4 causes an unexpectedly dramatic reduction in ICAM-1 and VCAM-1 levels in the vessel wall. It is likely that the effect of pUR4 on leukocyte infiltration is due to its ability to decrease VCAM-1 and ICAM-1 levels.

Fibronectin is also known to promote SMC de-differentiation (Hedin et al., "Diverse Effects of Fibronectin and Laminin on Phenotypic Properties of Cultured Arterial Smooth Muscle Cells," *J. Cell. Biol.* 107:307-319 (1988); Serini et al., "Mechanisms of Myofibroblast Activity and Phenotypic Modulation," *Exp. Cell. Res.* 250:273-283 (1999), which are hereby incorporated by reference in their entirety). However, the effect of matrix fibronectin on SMC de-differentiation has not been previously characterized. The in vivo data show that inhibiting fibronectin polymerization results in maintenance of the SMC differentiated phenotype (FIG. 4), indicating that fibronectin polymerization is an important regulator of SMC differentiation. Phenotypic modulation of SMC is thought to play a key role during vascular remodeling, contributing to increased SMC proliferation and migration. Hence, the ability of pUR4 to limit SMC dedifferentiation may be an important mechanism that contributes to reduced intima-media thickening after ligation.

Other ECM molecules have been shown to play important roles in vascular remodeling, including thrombospondin I, (Moura et al., "Thrombospondin-1 Activates Medial Smooth Muscle Cells and Triggers Neointima Formation upon Mouse Carotid Artery Ligation," *Arterioscler. Thromb. Vasc. Biol.* 27:2163-2169 (2007), which is hereby incorporated by reference in its entirety) vitronectin, (Dufourcq et al., "Vitronectin is Up-Regulated after Vascular Injury and Vitronectin Blockade Prevents Neointima Formation," *Cardiovasc. Res.* 53:952-962 (2002), which is hereby incorporated by reference in its entirety) and osteopontin (Liaw et al., "Neutralizing Antibodies Directed Against Osteopontin Inhibit Rat Carotid Neointimal Thickening after Endothelial Denudation," *Arterioscler. Thromb. Vasc. Biol.* 17:188-193 (1997), which is hereby incorporated by reference in its entirety). Interestingly, certain ECM and cytoskeletal proteins have been shown to influence both IMT and vessel size (Li et al., "Thrombomodulin Plays an Important Role in Arterial Remodeling and Neointima Formation in Mouse Carotid Ligation Model," *Thromb. Haemost.* 95:128-133 (2006); Myers et al., "Alterations of Arterial Physiology in Osteopontin-Null Mice," *Arterioscler. Thromb. Vasc. Biol.* 23:1021-1028 (2003); Schiffers et al., "Altered Flow-Induced Arterial Remodeling in Vimentin-Deficient Mice," *Arterioscler. Thromb. Vasc. Biol.* 20:611-616 (2000), which are hereby incorporated by reference in their entirety), which is similar to the findings with fibronectin. These data suggest that the effects of ECM proteins on outward remodeling may be an important aspect of their ability to regulate vascular remodeling. However, the data of Examples 1-6 are the first to show that fibronectin is an important regulator of vascular remodeling in vivo. These results are particularly striking given that the pUR4 peptide was delivered peradventitially and that the levels of the peptide peak 1 to 3 days after application. The ability of pUR4 to inhibit the vascular remodeling response long term (2 weeks), coupled with the reduction in leukocyte infiltration and cell proliferation, indicate that the peptide acts by blocking an early step(s) in the remodeling response. This early step is likely to involve decreased leukocyte infiltration that occurs, at least in part, as a result of decreased VCAM-1 and ICAM-1 expression. Taken together, these data demonstrate that pUR4, or another fibronectin inhibitor that acts by similar mechanisms, should have therapeutic applications in treating vascular occlusive diseases.

Example 7

Fibronectin Inhibition Blocks Intimal Thickening in Ex Vivo Cultured Human Saphenous Veins Human saphenous veins cultured in serum containing media develop intimal hyperplasia after 14 days in culture (Soyombo et al., "Intimal Proliferation in an Organ Culture of Human Saphenous Vein," *Am J Pathol.* 137(6):1401-1410 (1990); Angelini et al., "Smooth Muscle Cell Proliferation in Response to Injury in an Organ Culture of Human Saphenous Vein," *Eur J Vasc Surg.* 5(1):5-12 (1991); and Slomp et al., "Nature and Origin of the Neointima in Whole Vessel Wall Organ Culture of the Human Saphenous Vein," *Virchows Arch.* 428(1):59-67 (1996), which are hereby incorporated by reference in their entirety). This system thus provides an ex vivo model system for studying mechanisms that lead to intimal hyperplasia that has distinct advantages over in vitro culture systems. Although there are likely to be some differences between intimal hyperplasia in this system and that produced in arteries, human saphenous veins are commonly used for bypass surgery. Further, intimal hyperplasia frequently (>40%) develops in these vein grafts, compromising graft function. In addition, there are common features between saphenous vein hyperplasia and that produced in arteries, including intimal hyperplasia with increased SMC and ECM expansion (Soyombo et al., "Intimal Proliferation in an Organ Culture of Human Saphenous Vein," *Am J Pathol.* 137(6):1401-1410 (1990), which is hereby incorporated by reference in its entirety). Several studies have shown that certain agents decrease intimal thickening in both ex vivo human saphenous vein cultures and in in vivo arterial remodeling models (Engelse et al., "Adenoviral Activin a Expression Prevents Intimal Hyperplasia in Human and Murine Blood Vessels by Maintaining the Contractile Smooth Muscle Cell Phenotype." *Circ Res.* 90(10):1128-1134 (2002), which is hereby incorporated by reference in its entirety).

Figure 13:
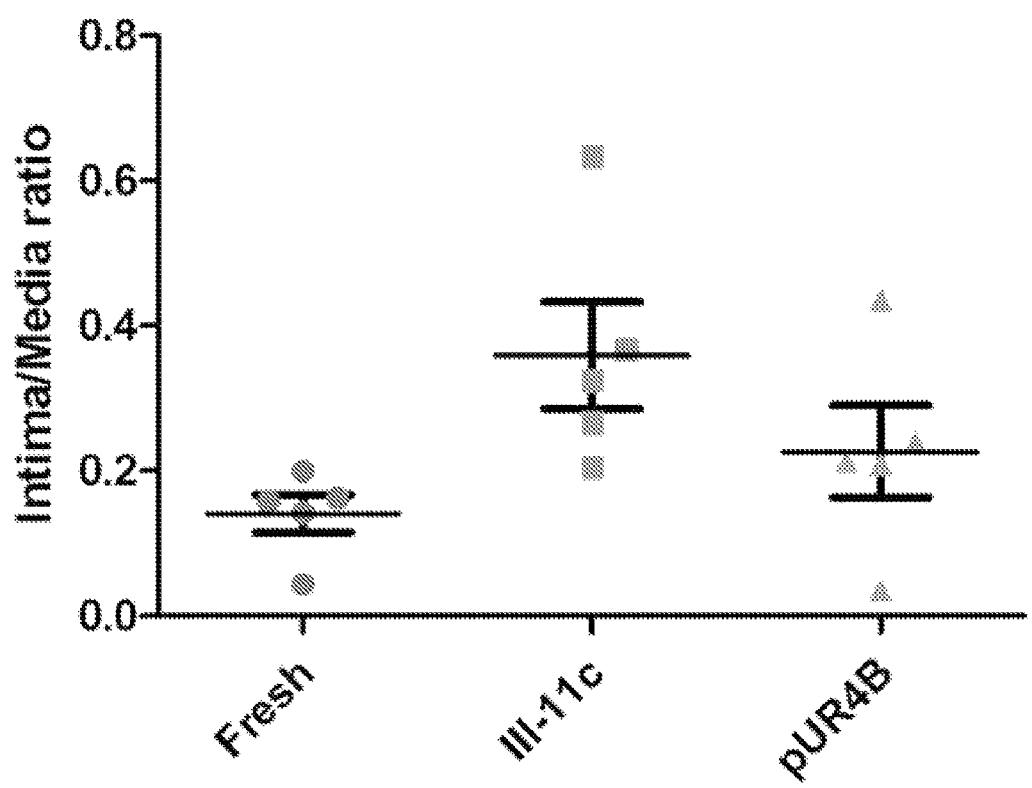
FIG. 13 shows pUR4 inhibition of intimal thickening in human saphenous veins. Saphenous veins were cut into 0.5 cm segments, and processed immediately (●) or cultured in 10% FBS/M199 containing 15 µM control III-11c peptide (■) or pUR4 (▲) at 37° C. for 14 days. Veins were fixed, paraffin embedded, sectioned, and stained. Morphometric analysis was performed on six randomly chosen sections using Image-Pro Plus software. The intima/media ratio was determined by dividing intima area by media area. Paired student t-test was used to analyze the data. Data are expressed as mean±S.E.M. *p<0.05.

As shown in FIGS. 2-3 (discussed supra) and FIG. 13, pUR4 decreases intimal thickening in both systems. The addition of pUR4 to ex vivo cultured saphenous veins decreases the intima/media ratio (FIG. 13). Because inflammatory cells are not present in this system, these data indicate that pUR4 is capable of blocking ECM remodeling in tissues by mechanisms that do not require inflammatory cells.

Example 8

Fibronectin Inhibition Reduces Cardiac Remodeling and Heart Failure

The therapeutic benefit of pUR4 mediated inhibition of fibronectin polymerization was investigated in a mouse model of myocardial infarction (MI). Male C57/Bl6 mice underwent permanent coronary artery ligation injury, verified at time of surgery by EKG S-T elevation. pUR4 or III-11C were administered via i.p. injection immediately following ligation. Animals subsequently received once daily IP injection for 6 days, and were followed for 4 weeks total. Serial, investigator blind echocardiography assessed cardiac function at baseline, 2 weeks, and 4 weeks.

Figure 14A:
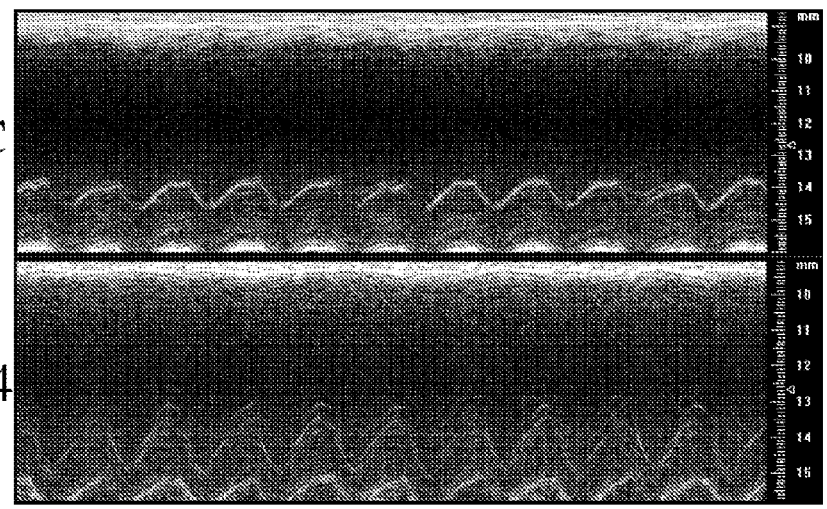
FIGS. 14A-14C demonstrate pUR4 mediated preservation of cardiac function in mice post-myocardial infarction (MI). C57/B16 male mice (12 wks) underwent permanent coronary ligation injury. pUR4 or control peptide (III-11C or del29) was delivered (25 mg/kg/day) in randomized fashion immediately following induction of EKG-verified MI, then once daily via IP injection for 6 days. Serial, investigator-blind echocardiography for 4 weeks was followed by sacrifice; hearts were excised, weighed, and prepared for histological processing.
Figure 14B:
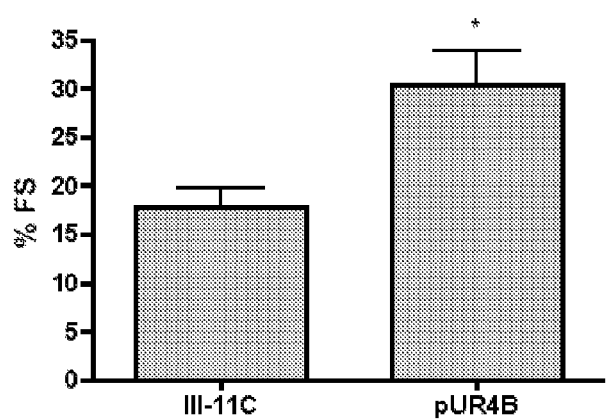
Figure 14C:
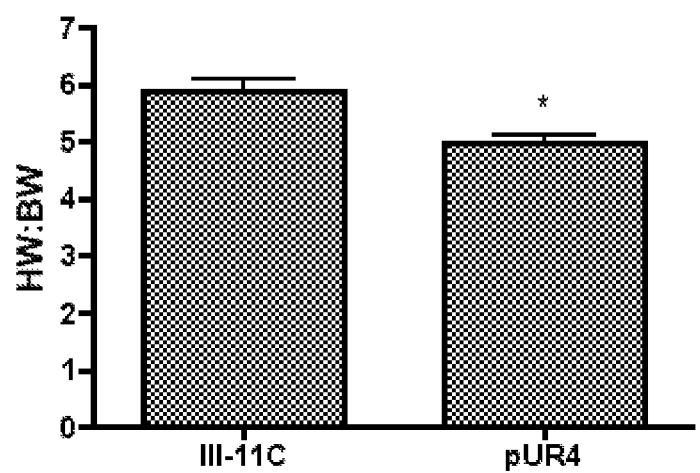

One week of pUR4 treatment preserved cardiac function (FIGS. 14A-14B) and reduced cardiac hypertrophy (FIG. 14C) up to 4 weeks post-MI. Ventricular dilation was also reduced in pUR4 treated mice as compared to control (end-diastolic diameter: $4.12\pm0.22$ vs. $4.84\pm0.19$, $p<0.05$; end systolic diameter: $2.91\pm0.27$ vs. $3.99\pm0.22$, $p<0.05$).

Figures 15A, 15B, 15C, 15D:
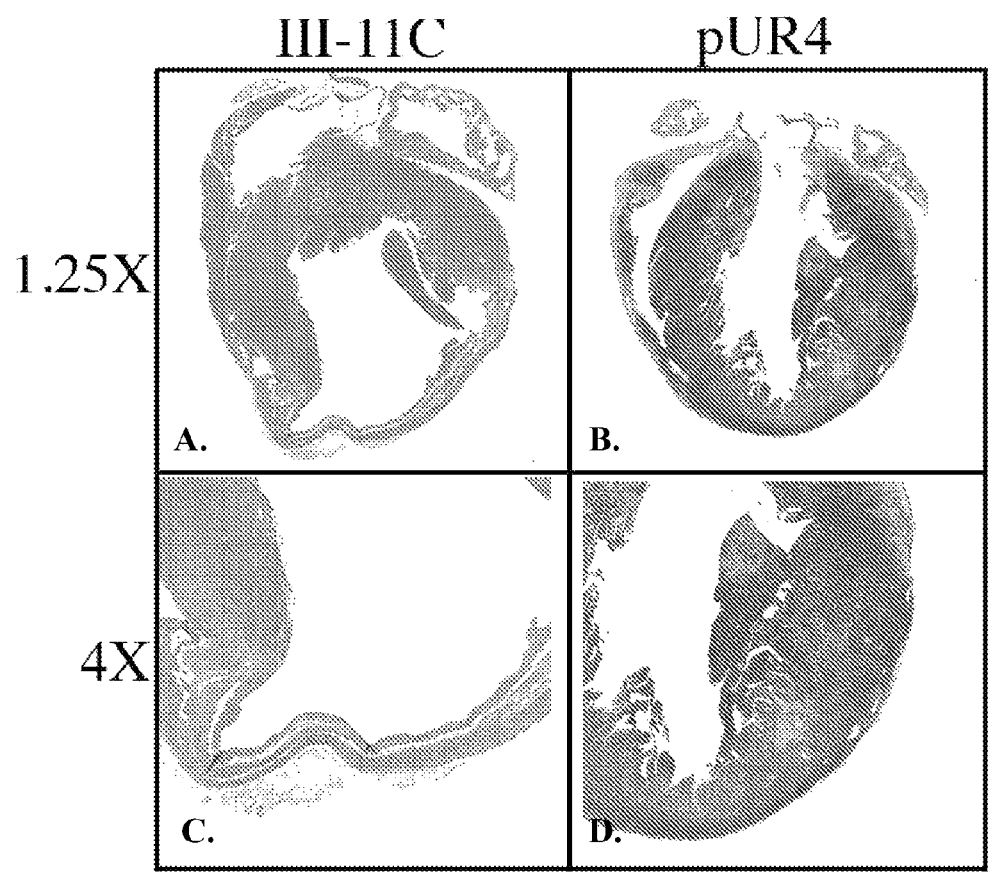
FIGS. 15A-15D show pUR4 mediated reduction in cardiac remodeling post-MI in mice administered pUR4 (FIGS. 15B, 15D) compared to control peptide (FIGS. 15A, 15C). Representative sections of heart tissue from mice described in FIG. 14 treated with Masson's Trichrome staining are shown at 1.25× (FIGS. 15A, 15B) and 4× (FIGS. 15C, 15D) magnification.
Figures 16A, 16B, 16C, 16D:
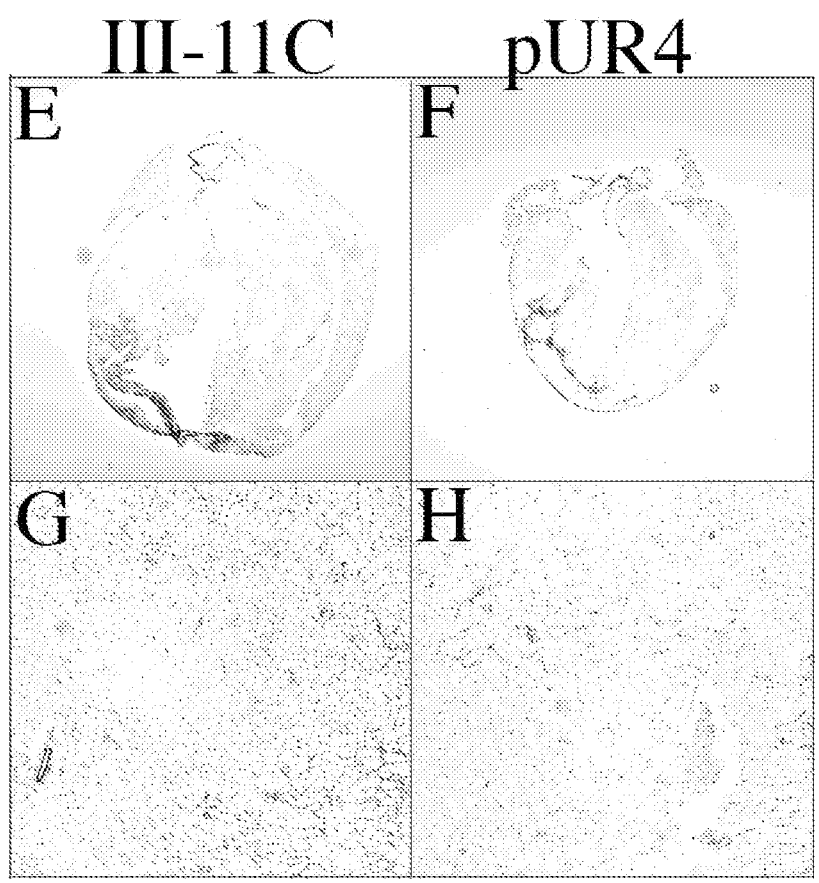
FIGS. 16A-16D show pUR4 mediated reduction in fibronectin deposition post-MI in mice administered pUR4 (FIGS. 16B, 16D) compared to control peptide (FIGS. 16A, 16C). Representative sections of heart tissue from mice described in FIG. 14 (sequential sections from the tissue sections shown in FIGS. 15A and 15B) were stained for fibronectin (brown) at 1.25× (FIGS. 16A, 16B) and 4× (FIGS. 16C, 16D).

Histological analysis of hearts 4 weeks post-MI demonstrated a pUR4-mediated reduction of cardiac remodeling, infarct size and infarct expansion (compare FIGS. 15A and 15C with FIGS. 15B and 15D). Importantly, pUR4 treatment reduced fibronectin deposition both within the infracted area, as well as in the remote myocardium (FIGS. 16A-16D).

In the initial stages of repair following injury to the heart, cardiac hypertrophy and ECM remodeling are thought to be compensatory (Cohn et al., "Cardiac Remodeling—Concepts and Clinical Implications: A Consensus Paper from an International Forum on Cardiac Remodeling," *J. Am. Coll. Cardiol.* 35:569-582 (2000), which is hereby incorporated by reference in its entirety). The delicate balance between matrix deposition and degradation is disrupted after myocardial infarction and in heart failure, including concordant elevations in expression/activity of both matrix metalloproteinases (MMP), which degrade ECM, and their tissue inhibitors (TIMPs) (Lalu et al., "Ischaemia-Reperfusion Injury activates Matrix Metalloproteinases in the Human Heart," *Eur. Heart J.* 26:27-35 (2005); Cheung et al., "Matrix Metalloproteinase-2 Contributes to Ischemia-Reperfusion Injury in the Heart," *Circ.* 101:1833-1839 (2000); Deschamps et al., "Trafficking of the Membrane Type-1 Matrix Metalloproteinase in Ischemia and Reperfusion: Relation to Interstitial Membrane Type-1 Matrix Metalloproteinase Activity," *Circ.* 111:1166-1174 (2005); Li et al., "Differential Expression of Tissue Inhibitors of Metalloproteinases in the Failing Human Heart," *Circ.* 98:1728-1734 (1998); Thomas et al., "Increased Matrix Metalloproteinase Activity and Selective Upregulation in LV Myocardium from Patients with End-Stage Dilated Cardiomyopathy," *Circ.* 97:1708-1715 (1998); Mukherjee et al., "Myocardial Infarct Expansion and Matrix Metalloproteinase Inhibition," *Circ.* 107:618-625 (2003); Ahmed et al., "Matrix Metalloproteinases/Tissue Inhibitors of Metalloproteinases: Relationship Between Changes in Proteolytic Determinants of Matrix Composition and structural, Functional, and Clinical Manifestations of Hypertensive Heart Disease," *Circ.* 113:2089-2096 (2006); Zavadzkas et al., "Cardiac-Restricted Overexpression of Extracellular Matrix Metalloproteinase Inducer Causes Myocardial Remodeling and Dysfunction in Aging Mice," *Am. J. Phusio. Heart Circ. Physiol.* 295:H1394-1402 (2008); Spinale et al., "Dynamic Changes in Matrix Metalloproteinase Activity within the Human Myocardial Interstitium During Myocardial Arrest and Reperfusion," *Circ.* 118:S16-23 (2008), which are hereby incorporated by reference in their entirety). Conflicting reports suggest either benefit or detriment of MMP and/or TIMP inhibition post-MI (Creemers et al., "Deficiency of TIMP-1 Exacerbates LV Remodeling after Myocardial Infarction in Mice," *Am. J. Physiol. Heart Circ. Physiol.* 284: H364-371 (2003); Yarbrough et al., "Selective Targeting and Timing of Matrix Metalloproteinase Inhibition in Post-Myocardial Infarction Remodeling," *Circ.* 108:1753-1759 (2003); Matsumura et al., "Targeted Deletion of Pharmacological Inhibition of MMP-2 Prevents cardiac Rupture after Myocardial Infarction in Mice," *J. Clin. Invest.* 115:599-609 (2005); Heymans et al., "Inhibition of Plasminogen Activators or Matrix Metalloproteinases Prevents Cardiac Rupture but Impairs Therapeutic Angiogenesis and Causes Cardiac Failure," *Nat. Med.* 5:1135-1142 (1999), which are hereby encorporated by reference in their entirety). Therefore, it was unexpected, and could not have been predicted, that inhibition of fibronectin deposition would be therapeutically beneficial in vivo.

Example 9

Determine pUR4 Dose-Response in Myocardial Infarction

To further evaluate pUR4 in MI, and to determine the effective dose (ED50), 10 mice per group will be subjected to permanent left anterior descending (LAD) coronary artery ligation. Mice will be injected immediately post-MI with 1, 10, 25 and 50 mg/kg/day of pUR4 or control peptide for 7d at intervals based on pharmacokinetic studies. During the course of 28 days post-MI and upon sacrifice, animals will undergo all studies as outlined below.

Conscious echocardiography is non-invasive, can be performed in serial fashion, and provides excellent data regarding in vivo cardiac morphology and function. Serial echocardiography will be performed at baseline, 1, 2 and 4 weeks after injury (10 mice per group) using the VisualSonics Vevo 770, which has been designed specifically for rodent studies to dramatically enhance visualization and assessment of cardiac function (Ng et al., "TGF-Beta-Dependent Pathogenesis of Mitral Valve Prolapse in a Mouse Model of Marfan Syndrome," *J. Clin. Invest.* 114(11):1586-1592 (2004); Zhou et al., "Comprehensive Transthoracic Cardiac Imaging in Mice Using Ultrasound Biomicroscopy with Anatomical Confirmation by Magnetic Resonance Imaging," *Physiol. Genomics* 18(2):232-244 (2004), which are hereby incorporated by reference in their entirety). Conscious echocardiography will be performed, eluding the potential pitfalls of heart rate variability and alteration of cardiac function under anesthesia. LV function will be assessed by both 2-D and M-mode echocardiography in both the long- and short-axis view. Physical and functional parameters will be assessed, including determination of cardiac function as % FS.

To determine alterations of normal cardiac rhythm (a common event in heart failure, particularly in post-MI remodeling), ECG recordings will be obtained in all mice. ECG will be recorded during the MI procedure to validate ST segment elevation characteristic of ischemia, and again at 4 weeks to investigate arrhythmia. Electrocardiography recordings are performed with three lead recordings processed through a PowerLab and analyzed with Chart Reader software. For higher resolution, a six-lead body surface ECGs is utilized in conscious mice. Signals are amplified/filtered (CyberAmp 380, Axon Instruments), and digitized (MiniDigi 1A, Axon Instruments). Signal averaging (10-15 beats) provides average interval duration measurements and improve the signal-to-noise ratio for each mouse ECG trace. ECG intervals will be defined as described previously (Pawlinski et al., "Protease-Activated Receptor-1 Contributes to Cardiac Remodeling and Hypertrophy," *Circulation* 116(20):2298-2306 (2007); Maekawa et al., "Inhibiting p90 Ribosomal S6 Kinase Prevents (Na+)-H+ Exchanger-Mediated Cardiac Ischemia-Reperfusion Injury," *Circulation* 113(21):2516-2523 (2006); Morley et al., "Characterization of Conduction in the Ventricles of Normal and Heterozygous Cx43 Knockout Mice Using Optical Mapping," *J. Cardiovasc. Electrophysiol.* 10(10):1361-1375 (1999), which are hereby incorporated by reference in their entirety).

To determine the extent of hypertrophy/dilation following injury the heart weight to body weight ratio (mg/g) and heart weight to tibia length will be analyzed at the time of sacrifice, 4 weeks post-MI.

Apoptotic cell death contributes to cardiac remodeling and heart failure, particularly after myocardial infarction. The impact of pUR4 on the rate of cardiac apoptosis will be assessed using two different methods. Hearts will be perfused with saline followed by 4% PFA in PBS for histological analysis. The TUNEL assay will be performed on heart sections to identify 3'-OH DNA ends generated during apoptosis. Tunel staining will be performed on heart sections to investigate apoptotic rate in infarct, peri-infarct, and remote myocardium. Early apoptosis in samples of the left ventricle will be determined by measuring the activity of caspase 3 using a commercial kit (Roche). In addition, caspase-3 activity will be determined in LV homogenates using a colorimetric assay, as well as Bax expression and Caspase 3 cleavage by Western Blot.

Cardiac remodeling post-MI is accompanied by an initial infarct that is replaced over time with matrix-rich scar tissue and non-myocyte cellular proliferation. The data of Example 8 demonstrate that pUR4 reduces ECM remodeling, scar formation, infarct expansion and both local and remote cardiac remodeling. Therefore, cell proliferation will be assessed by staining for proliferating cell nuclear antigen (PCNA). To assess cardiomyocyte morphology, sections will be labeled with FITC-conjugated wheat germ agglutinin (WGA), counterstained with DAPI, and cross-sectional area determined in >200 cells/animal by microscopy. To assess tissue viability and fibrosis, Masson's Trichrome and picrosirius red staining will be performed on heart sections, where infarct size will also be determined. Infarct size will be presented as a ratio of fibrotic to total area of LV. Five serial sections will be analyzed from each mouse. To determine infarct size and area at risk in a subset of animals (particularly relevant for ischemia reperfusion studies outlined below), coronary ligation will be performed, Evan's Blue will be injected, and 2,3,5-Triphenyltetrazolium chloride (TTC) staining on 4-5 serial slices of the heart will be carried out as described previously (Pawlinski et al., "Protease-Activated Receptor-1 Contributes to Cardiac Remodeling and Hypertrophy," *Circulation* 116(20):2298-2306 (2007); Itoh et al., "Role of p90 Ribosomal S6 Kinase-Mediated Prorenin-Converting Enzyme in Ischemic and Diabetic Myocardium," *Circulation* 113(14):1787-1798 (2006); Maekawa et al., "Inhibiting p90 Ribosomal S6 Kinase Prevents (Na$^+$)—H+ Exchanger-Mediated Cardiac Ischemia-Reperfusion Injury," *Circulation* 113(21):2516-2523 (2006), which are hereby incorporated by reference in their entirety).

Heart sections will be stained with Masson's trichrome and picrosirius red to visualize fibrosis. Morphological and histological examination will be performed as previously described (Itoh et al., "Role of p90 Ribosomal S6 Kinase-Mediated Prorenin-Converting Enzyme in Ischemic and Diabetic Myocardium," *Circulation* 113(14):1787-1798 (2006); Milano et al., "Myocardial Expression of a Constitutively Active Alpha 1B-Adrenergic Receptor in Transgenic Mice Induces Cardiac Hypertrophy," *Proc. Natl. Acad. Sci. U.S.A.* 91(21):10109-10113 (1994); Jaber et al., "Essential Role of Beta-Adrenergic Receptor Kinase 1 in Cardiac Development and Function," *Proc. Natl. Acad. Sci. U.S.A.* 93(23):12974-12979 (1996); Rockman et al., "Expression of a Beta-Adrenergic Receptor Kinase 1 Inhibitor Prevents the Development of Myocardial Failure in Gene-Targeted Mice," *Proc. Natl. Acad. Sci. U.S.A.* 95(12):7000-7005 (1998); Maekawa et al., "Inhibiting p90 Ribosomal S6 Kinase Prevents Na+-H+ Exchanger-Mediated Cardiac Ischemia-Reperfusion Injury," *Circulation* 113(14):1787-1798 (2006); Maekawa et al., "Improved Myocardial Ischemia/Reperfusion Injury in Mice Lacking Tumor Necrosis Factor-Alpha," *J. Am. Coll. Cardiol.* 39(7):1229-1235 (2002), which are hereby incorporated by reference in their entirety). Total RNA will be extracted from samples of the left ventricle and northern blotting will be performed to determine the levels of collagen I, II, IV and VI.

The data of Example 8 also demonstrates reduced collagen and fibronectin deposition in animals treated with pUR4 post-MI (FIGS. 15 and 16, respectively). To investigate fibronectin and collagen deposition following ischemic injury, staining will be performed as described previously (Chiang et al., "Fibronectin Is an Important Regulator of Flow-Induced Vascular Remodeling," *Arterioscler. Thromb. Vasc. Biol.* 29(7):1074-1079 (2009), which is hereby incorporated by reference in its entirety).

To investigate the role of pUR4 in recruiting inflammatory cells, sections will be stained with CD45 antibody as described previously (Chiang et al., "Fibronectin Is an Important Regulator of Flow-Induced Vascular Remodeling," *Arterioscler. Thromb. Vasc. Biol.* 29(7):1074-1079 (2009), which is hereby incorporated by reference in its entirety). Elevated plasma levels of IL-6, IL-1β and TNF-α are associated with heart failure both in humans and animals, and are both pro-inflammatory and pro-hypertrophic, both processes that contribute to pathologic cardiac remodelling (Jaffre et al., "Serotonin and Angiotensin Receptors in Cardiac Fibroblasts Coregulate Adrenergic-Dependent Cardiac Hypertrophy," *Circ. Res.* 104(1):113-123 (2009); Li et al., "Elevated Insulin-Like Growth Factor-I and Transforming Growth Factor-Beta 1 and their Receptors in Patients with Idiopathic Hypertrophic Obstructive Cardiomyopathy. A Possible Mechanism," *Circulation* (19 Suppl):II144-150 (1998); Zen et al., "Analysis of Circulating Apoptosis Mediators and Proinflammatory Cytokines in Patients with Idiopathic Hypertrophic Cardiomyopathy: Comparison Between Nonobstructive and Dilated-Phase Hypertrophic Cardiomyopathy," *Int. Heart J.* 46(2):231-244 (2005)). To investigate the role of pUR4 in reducing circulating inflammatory mediators and prohypertrophic cytokines, blood will be harvested by intracardiac puncture at time of sacrifice. Plasma will be separated by centrifugation and IL-6, TNF-α or IL-1β plasma concentration will be determined by ELISA assay as recently described (Jaffre et al., "Serotonin and Angiotensin Receptors in Cardiac Fibroblasts Coregulate Adrenergic-Dependent Cardiac Hypertrophy," *Circ. Res.* 104(1):113-123 (2009), which is hereby incorporated by reference in its entirety).

Cardiac hypertrophy induces a "fetal gene program" that includes changes in expression of ANF, BNP, α-skeletal actin, α-MHC, β-MHC and SERCA-2a. Fibronectin and collagen I and III are also closely associated with pathologic cardiac remodeling. In a subset of animals, the expression of these genes will be analyzed by SYBR-green based real-time PCR analysis and normalized to GAPDH, as previously described (Blaxall et al., "Differential Myocardial Gene Expression in the Development and Rescue of Murine Heart Failure," *Physiol. Genomics.* 15(2):105-114 (2003); Blaxall et al., "Differential Gene Expression and Genomic Patient Stratification Following Left Ventricular Assist Device Support," *J. Am. Coll. Cardiol.* 41(7):1096-1106 (2003); Pawlinski et al., "Protease-Activated Receptor-1 Contributes to Cardiac Remodeling and Hypertrophy," *Circulation* 116(20): 2298-2306 (2007); Bullard et al., "Identification of Nogo as a Novel Indicator of Heart Failure," Physiol. Genomics. 32(2):182-189 (2008), which are hereby incorporated by reference in their entirety).

Example 10

Investigate Efficacy of Peptide pUR4 Following Myocardiac Ischemia-Reperfusion (I/R) Injury Permanent coronary ligation is a widely accepted mouse model of MI. However, patients in general undergo I/R injury, where both the ischemia and the reperfusion have pathologic effects on cardiac structure, function and remodeling. To determine the efficacy of fibronectin inhibition in this relevant model of heart failure, 10 mice per group will be subjected to cardiac I/R injury and treated for the first 7 days with either pUR4 or III-11C. The cardiac ischemia-reperfusion injury model has been described previously (Pawlinski et al., "Protease-Activated Receptor-1 Contributes to Cardiac Remodeling and Hypertrophy," *Circulation* 116(20):2298-2306 (2007); Itoh et al., "Role of p90 Ribosomal S6 Kinase-Mediated Prorenin-Converting Enzyme in Ischemic and Diabetic Myocardium," *Circulation* 113(14):1787-1798 (2006); Maekawa et al., "Inhibiting p90 Ribosomal S6 Kinase Prevents (Na+)-H+ Exchanger-Mediated Cardiac Ischemia-Reperfusion Injury," *Circulation* 113(21):2516-2523 (2006), which are hereby incorporated by reference in their entirety). Briefly, male mice at 8-12 wks old will be used for all experiments. Mice are anesthetized 2% isoflurane/40% oxygen, and maintained with 0.5% isoflurane/40% oxygen during open-chest surgery. Oral tracheal intubation is performed (0.3 ml tidal volume, 120 breaths/min), and the heart is visualized by lateral intercostal incision. The LAD coronary artery is ligated for 45 min with 8-0 nylon surgical suture tied around PE-10 tubing 2.0 mm distal from tip of the left atrium. Continual ECG recording is performed to assess cardiac conduction and verify ST elevation characteristic of cardiac ischemia. The chest is sutured closed and the animals are monitored for 1-2 weeks of reperfusion. Echocardiography is performed to determine the functional course of disease progression.

This model of cardiac injury is aggressive, and mortality is often high prior to 4 weeks. Thus, the first experiment will analyze cardiac remodeling at 2 weeks (a late phase of remodeling), which is associated with LV dilation and reduced ventricular function. To investigate the effects of pUR4 in early stage remodeling, in a second experiment of 10 animals per group, animals will be analyzed at 1 week post-I/R (an early phase of remodeling). To determine infarct size and area at risk in a subset of animals, the coronary will be re-ligated, and Evan's Blue injection and TTC staining will be performed on 4-5 serial slices of the heart, calculating both area at risk (AAR) and infarct area, as described previously (Pawlinski et al., "Protease-Activated Receptor-1 Contributes to Cardiac Remodeling and Hypertrophy," *Circulation* 116(20): 2298-2306 (2007); Itoh et al., "Role of p90 Ribosomal S6 Kinase-Mediated Prorenin-Converting Enzyme in Ischemic and Diabetic Myocardium," *Circulation* 113(14):1787-1798 (2006); Maekawa et al., "Inhibiting p90 Ribosomal S6 Kinase Prevents (Na+)-H+ Exchanger-Mediated Cardiac Ischemia-Reperfusion Injury," *Circulation* 113(21):2516-2523 (2006), which are hereby incorporated by reference in their entirety). Cardioprotection with pUR4 treatment similar to what was observed in Example 8 with permanent coronary ligation is anticipated.

Example 11

Determine pUR4 Inhibition of Pulmonary Fibrosis

Bleomycin, an antineoplastic antibiotic, will be used to induce lung injury and pulmonary fibrosis in mice. This model is a well established model of lung fibrosis that recapitulates the key pathological features of human pulmonary fibrosis (Kolb et al., "Transient Transgene Expression of Decorin in the Lung Reduces the Fibrotic Response to Bleomycin," *An. J. Respir. Crit. Care. Med.* 163:770-777 (2001); Fang, K. C., "Mesenchymal Regulation of Alveolar Repair in Pulmonary Fibrosis," *Am. J. Respir. Cell Mo. Biol.* 23:142-145 (2000), which are hereby incorporated by reference in their entirety). Type I collagen is the major collagen type that accumulates during pulmonary fibrosis in humans and mice (Crouch, E., "Pathobiology of Pulmonary Fibrosis," *Am. J. Physio.* 259:L159-184 (1990), which is hereby incorporated by reference in its entirety). In the bleomycin model, there is a two-fold increase in lung collagen within three weeks of bleomycin administration (Fang, K. C., "Mesenchymal Regulation of Alveolar Repair in Pulmonary Fibrosis," *Am. J. Respir. Cell Mo. Biol.* 23:142-145 (2000); Madtes et al., "Transforming Growth Factor-Alpha Deficiency Reduces Pulmonary Fibrosis in Transgenic Mice," *Am. J. Respir. Cell Mol. Biol.* 20:924-934 (1999), which are hereby incorporated by reference in their entirety).

Bleomycin will be introduced by intratracheal installation. Pilot experiments will be conducted to determine the best route of delivery for pUR4. Initially, two approaches will be taken. In the first, pUR4 or control peptides will be administered to animals by oropharyngeal aspiration the day before bleomycin treatment, and at 2 day intervals following bleomycin treatment. Oropharyngeal aspiration to deliver solutions and proteins into the lungs has been previously described (Lakatos et al., "Oropharyngeal Aspiration of a Silica Suspension Produces a Superior Model of Silicosis in the Mouse when Compared to Intratracheal Instillation," *Exp. Lung Res.* 32:181-199 (2006); Pratt et al., "Oropharyngeal Aspiration of Ricin as a Lung Challenge Model for Evaluation of the Therapeutic Index of Antibodies Against Ricin A-Chain for Post-Exposure Treatment," *Exp. Lung Res.* 33:459-481 (2007), which are hereby incorporated by reference in their entirety). In the second approach, pUR4 or control peptides will be administered by i.p. injection the day before bleomycin treatment, and daily for 7-14 days following treatment. Intraperitoneal injection to deliver drugs and proteins into the lung in experimental models of fibrosis has been previously described (Pilling et al., "Reduction of Bleomycin-Induced Pulmonary Fibrosis by Serum Amyloid P," *J. Immunol.* 179:4035-4044 (2007); Oury et al., "Attenuation of Bleomycin-Induced Pumonary Fibrosis by a Catalytic Antioxidant Metalloporphyrin," *Am. J. Respir. Cell Mol. Biol.* 25:164-169 (2001); Huang et al., "IL-7 Inhibits Fibroblast TGF-Beta Production and Signaling in Pulmonary Fibrosis," *J. Clin. Invest.* 109:931-937 (2002); Inayama et al., "A Novel Ikβ Kinase-Beta Inhibitor Ameliorates Bleomycin-Induced Pulmonary Fibrosis in Mice," *Am. J. Respir. Crit. Care Med.* 173:1016-1022 (2006), which are hereby incorporated by reference in their entirety).

Pilot experiments will be performed to determine the optimal dose and timing of pUR4 administration. In the first study, the half-life of pUR4 in blood will be determined. Various doses of pUR4 (1, 10, 25, or 50 mg/kg) will be injected i.p. into mice. These doses include the dose of pUR4 that was used (25 mg/kg) in the mouse model of myocardial infarction that was effective in improving heart function (Example 8). These doses are also similar to peptide doses that others have injected i.p. into mice or rats that were efficacious in inhibiting integrin or thrombospondin activity (Kondou et al., "A Blocking Peptide for Transforming Growth Factor-Beta1 Activation Prevents Hepatic Fibrosis in vivo," *J. Hepatol.* 39:742-748 (2003); Reiher et al., "Inhibition of Tumor Growth by Systemic Treatment with Thrombospondin-1 Peptide Mimetics," *Int. J. Cancer* 98:682-689 (2002); Stoeltzing et al, Inhibition of Integrin Alpha5Beta1 Function with a Small Peptide (ATN-161) Plus Continuous 5-FU Infusion Reduces Colorectal Liver Metastases and Improves Survival in Mice," *Int. J. Cancer* 104:496-503 (2003), which are hereby incorporated by reference in their entirety). Blood samples will be obtained from mice at times ranging from 0.5 to 24 hours, and the level of pUR4 determined by competitive or capture ELISA.

In the second pilot study, the tissue levels of pUR4, the consistency of peptide delivery, and the levels of pUR4 in the lung will be determined. Two doses of pUR4 (determined from pilot study 1) will be injected i.p. Tissue levels of the peptide will be determined by ELISA and/or western blot analysis at the t½ of the peptide, and at 24 hours post injection. pUR4 contains a His-tag, and is readily detectable using an anti-His antibody. Alternatively, Texas Red (TR) labeled pUR4 will be used for these studies. TR-pUR4 is functionally active in inhibiting fibronectin assembly.

In the third pilot study, the effective dose of pUR4 will be determined. For this study, mice will undergo the bleomycin procedure. Mice will be injected with two different doses of pUR4 at intervals based on the plasma half life of pUR4, and the persistence of the peptide within the lung. Twenty-one days after injection, mice will be perfusion fixed, and the fibrosis score determined as described below. These studies will determine the optimal dose and frequency of administration of pUR4 for the bleomycin experiments. Similar studies will be done to determine the optimal dose and frequency of application of the R1R2 peptide.

The blood half life may have little relevance to determining the optimal dose and frequency of delivery of peptides by oropharyngeal aspiration. Determining the dose and frequency of application will be guided by previous experience in the carotid artery and heart, and by the known doses of pUR4 and R1R2 that are effective at inhibiting fibronectin binding to cells, fibronectin matrix assembly or fibronectin-collagen binding in vitro. pUR4 inhibits fibronectin binding to the cell surface with an EC50 of 10 nM. Cell culture experiments indicate that pUR4 is effective at inhibiting fibronectin matrix assembly at 50-100 nM. Further, in vivo experiments indicate that local delivery of 20 µM pUR4 is effective at inhibiting vascular remodeling (Examples 2 and 3). In addition, when used in a mouse model of heart failure, daily i.p. injection of pUR4 (25 mg/kg) for 7 days was effective in preserving heart function. For oropharyngeal aspiration, two initial doses of 0.5 and 5 mM will be tried. These doses are based on the doses of pUR4 known to be effective in other models, calculations of the surface area of the lung, and the calculated local concentration of pUR4 that would result from application of this amount of peptide. It is estimated that peptides will be diluted 50-100 fold in the alveolar lining fluid. Based on studies in the carotid artery, it is anticipated that pUR4 will persist in tissues for several days (see Example 2 and FIG. 8). Although the kinetics of peptide retention could be different in the lung and the carotid artery, it is anticipated that a two day treatment regimen should be sufficient to maintain relatively constant levels of pUR4 in the lung. Hence, initial doses of 0.5 and 5 mM of the peptide will be administered one day prior to bleomycin treatment, and then at 2 day intervals following bleomycin treatment.

Cell culture experiments indicate that R1R2 is effective at blocking fibronectin-collagen interactions at nM concentrations (100-500 nM). Experiments with ex vivo saphenous vein segments indicate that 10× higher levels of R1R2 can attenuate intimal hyperplasia. Based on the considerations described above, two doses will be tried in the pilot experiments, 0.5 mM and 5 mM. Subsequent experiments will be performed at the dose that is found to be most effective in attenuating fibrosis development.

The experimental groups will include: 1) bleomycin alone; 2) bleomycin+pUR4 peptide; and 3) bleomycin+control del29 peptide. Control animals will undergo the instillation procedure with PBS and will also receive: 4) pUR4; 5) the del29 control; or 6) PBS the day prior to instillation. Del29 is a mutant pUR4 protein that contains a 1 amino acid deletion and retains its ability to bind to fibronectin, but does not prevent fibronectin matrix polymerization and does not block the ability of fibronectin to promote angiogenesis in vitro or in vivo (5).

To determine the effects of pUR4 on fibrosis, mice will be sacrificed 7, 14, and 21 days post bleomycin. Lungs will be removed, sectioned, and processed for immunocytochemistry. The levels of individual matrix components will be assessed by immunohistochemistry using antibodies to collagen I, collagen III, and fibronectin, as described in the preceding examples. Protein levels of fibronectin and collagens I and III will be quantitated by western blot analysis of tissue extracts. Total collagen content will be determined by measuring the hydroxyproline content of lung extracts.

The fibrotic score will be determined by examining histological sections of lung sections stained with Masson trichrome to provide a quantitative index of lung scarring/fibrosis. Slides will be examined by two people in a blinded fashion, using the following grading system, as previously described (Kolb et al., "Transient Transgene Expression of Decorin in the Lung Reduces the Fibrotic Response to Bleomycin," *An. J. Respir. Crit. Care. Med.* 163:770-777 (2001); Madtes et al., "Transforming Growth Factor-Alpha Deficiency Reduces Pulmonary Fibrosis in Transgenic Mice," *Am. J. Respir. Cell Mol. Biol.* 20:924-934 (1999), which are hereby incorporated by reference in their entirety): Grade 0=normal lung; Grade 1=sparse fibrosis (fine connective tissue fibrils in less than 50% of the area); Grade 2=mild fibrosis (fine fibrils in 50-100% of the area and/or patchy peribronchial and parenchymal scars involving less than 50% of the area; Grade 4=severe fibrosis (disseminated scars involving 50-100% of the section).

The persistence of the peptides in the lung will be determined by immunohistochemical methods. Since R1R2 and pUR4 will bind fibronectin in tissues, lung tissue sections will be stained with an anti-His antibody to determine the distribution of the His-tagged pUR4 and R1R2 peptides. Quantitative immunohistochemistry will be used to estimate the levels of the peptide in the tissue over time, as described supra in Example 2, which is hereby incorporated by reference in its entirety). To more precisely monitor the levels of R1R2 and pUR4 in the tissues, proteins will be extracted from tissues and detected by western blot.

Example 12

Determine pUR4 Prevention of Pulmonary Fibrosis Progression Post Injury

The ability of pUR4 to prevent the progression of fibrosis would have translational significance, as administering this peptide after lung injury has occurred is relevant to the clinical situation, where patients typically present with ongoing disease. pUR4 will be administered 10 days post bleomycin treatment to determine whether it can prevent the progression of fibrosis. Early fibrotic changes, including the acute inflammatory response and increased collagen content are evident within 10 days of bleomycin treatment (Kolb et al., "Transient Transgene Expression of Decorin in the Lung Reduces the Fibrotic Response to Bleomycin," *An. J. Respir. Crit. Care. Med.* 163:770-777 (2001); Madtes et al., "Transforming Growth Factor-Alpha Deficiency Reduces Pulmonary Fibrosis in Transgenic Mice," *Am. J. Respir. Cell Mol. Biol.* 20:924-934 (1999); Hattori et al., "Bleomycin-Induced Pulmonary Fibrosis in Fibrinogen-Null Mice," *J. Clin. Invest.* 106:1341-1350 (2000); Kaminski et al., "Global Analysis of Gene Expression in Pulmonary Fibrosis Reveals Distinct Programs Regulating Lung Inflammation and Fibrosis," *Proc. Natl. Acad. Sci. U.S.A.* 97:1778-1783 (2000), which are hereby incorporated by reference in their entirety). Lung tissue will be analyzed to determine the effect of pUR4 treatment on fibronectin accumulation, collagen I accumulation, myofibroblast content, fibrosis score, and inflammation. For these experiments, the time points examined will be 10, 14, 21, and 28 days. It is anticipated that pUR4 will be able to prevent the progression of fibrosis in this model of ongoing fibrosis.

Example 13

Determine pUR4 Affect on Myofibroblast Accumulation in Pulmonary Fibrosis

Myofibroblast accumulation is thought to be an important contributor to the development and persistence of pulmonary fibrosis. Therefore, whether pUR4 affects myofibroblast number will be assessed by immunohistochemical analysis of tissue sections. Sections will be stained with antibodies to smooth muscle α-actin to identify myofibroblasts, and counter stained with hematoxylin. The number of positive cells will be counted per unit area and expressed as percent positive cells per cross sectional area. Whether pUR4 affects cell proliferation will also be assessed by staining tissue sections with PCNA. Sections will be co-stained with antibodies to smooth muscle α-actin or CD45 (leukocyte common antigen) to distinguish between myofibroblasts and immune cells. It is anticipated that pUR4 will prevent increased myofibroblast numbers following bleomycin induced injury.

Example 14

Determine pUR4 Affects on Inflammatory Response in Pulmonary Fibrosis

Bleomycin induces an acute inflammatory response, which is thought to contribute to the development of fibrosis. Therefore, inflammatory cells present in the lung will also be characterized and quantitated by analyzing cells present in bronchiolar lavage (BAL) fluid as previously described (Kolb et al., "Transient Transgene Expression of Decorin in the Lung Reduces the Fibrotic Response to Bleomycin," *An. J. Respir. Crit. Care. Med.* 163:770-777 (2001), which is hereby incorporated by reference in its entirety). Tissue sections will also be stained for the presence of immune cells, and quantitative immunohistochemistry will be performed to determine whether pUR4 decreases inflammatory cell infiltration in the lung as it was shown to do in the context of vascular remodeling (Example 6). If pUR4 decreases inflammatory cell infiltration in the lung, then immunohistochemistry, western blotting, quantitative RT PCR, and/or ELISA assays will be used to analyze lung sections, lung tissue, or BAL for the presence of various inflammatory mediators that play an important role in regulating lung fibrosis, including: NFκβ, TGFβ, TNFα, and IL-1β as described (Kolb et al., "Transient Transgene Expression of Decorin in the Lung Reduces the Fibrotic Response to Bleomycin," *An. J. Respir. Crit. Care. Med.* 163:770-777 (2001); Lakatos et al., "Oropharyngeal Aspiration of a Silica Suspension Produces a Superior Model of Silicosis in the Mouse when Compared to Intratracheal Instillation," *Exp. Lung Res.* 32:181-199 (2006); Inayama et al., "A Novel Iκβ Kinase-Beta Inhibitor Ameliorates Bleomycin-Induced Pulmonary Fibrosis in Mice," *Am. J. Respir. Crit. Care Med.* 173:1016-1022 (2006); Sime et al., "Adenovector-Mediated Gene Transfer of Active Transforming Growth Factor-Beta1 Induces Prolonged Severe Fibrosis in Rat Lung," *J. Clin. Invest.* 100:768-776 (1997); Gasse et al., "IL-1R1/MyD88 Signaling and the Inflammasome are Essential in Pulmonary Inflammation and Fibrosis in Mice," *J. Clin. Invest.* 117:3786-3799 (2007); Muro et al., "An Essential Role for Fibronectin Extra Type III Domain A in Pulmonary Fibrosis," *Am. J. Respir. Crit. Care. Med.* 177:638-645 (2008), which are hereby incorporated by reference in their entirety). The wet/dry weight ratio of the lungs and the total protein concentration in the BAL will also be determined as measures of the inflammatory response. These experiments will be performed at days 3, 7, and 14 post bleomycin, since the inflammatory response peaks between days 3-9 in this model (Moeller et al., "The Bleomycin Animal Model: A Useful Tool to Invesigate Treatment Options for Idiopathic Pulmonary Fibrosis?" *Int. J. Biochem. Cell Biol.* 40:362-382 (2008); Chaudhary et al., "Pharmacologic Differentiation of Inflammation and Fibrosis in the Rat Bleomycin Model," *Am. J. Respir. Crit. Care Med.* 173:769-776 (2006), which are hereby incorporated by reference in their entirety). It is expected that pUR4 will inhibit fibrosis, in part, by inhibiting associated inflammatory events.

Example 15

Determine Whether pUR4 Leads to the Production of Fibronectin and Collagen Fragments Fibronectin and collagen fragments have been detected in vivo, especially in areas of tissue injury (Sukhova et al., "Evidence for Increased Collagenolysis by Interstitial Collegenases-1 and -3 in Vulnerable Human Atheromatous Plaques," *Circ.* 99:2503-2509 (1999); Barilla et al., "Fibronectin Fragments and their Role in Inflammatory Arthritis," *Semin. Arthritis Rheum.* 29:252-265 (2000), which are hereby incorporated by reference in their entirety). Fibronectin fragments can have potent biological effects, including effects on cell migration, proliferation, fibronectin matrix assembly, and lung fibroblast apoptosis (Tellier et al., "Superfibronectin, a Multimeric form of Fibronectin, Increases HIV Infection of Primary CD4+T Lymphocytes," *J. Immunol.* 164:3236-3245 (2000); Bourdoulous et al., "Fibronectin Matrix Regulates Activation of RHO and CDC42 GTPases and Cell Cycle Progression," *J. Cell Biol.* 143:267-276 (1998); Pasqualini et al., "A Polymeric Form of Fibronectin has Antimetastatic Effects Against Multiple Tumor Types," *Nat. Med.* 2:1197-11203 (1996); Schor et al., "Substratum-Dependent Stimulation of Fibroblast Migration by the Gelatin-Binding Domain of Fibronectin," *J. Cell Sci.* 109:2581-2590 (1996); Hadden et al., "Induction of Lung Fibroblast Apoptosis by Soluble Fibronectin Peptides," *Am. J. Respir. Crit. Care Med.* 162:1553-1560 (2000), which are hereby incorporated by reference in their entirety). Collagen fragments have also been shown to be biologically active, and can influence cell proliferation and migration (Carragher et al., "Degraded Collagen Fragments Promote Rapid Disassembly of Smooth Muscle Focal Adhesions that Correlates with Cleavage of pp 125(FAK), Paxillin, and Talin," *J. Cell Biol.* 147:619-630 (1999); String a et al., Collagen Degradation and Platelet-Dreived Growth Factor Stimulate the Migration of Vascular Smooth Muscle Cells," *J. Cell Sci.* 113:2055-2064 (2000), which are hereby incorporated by reference in their entirety). Collagen fragments have been detected in the BAL of mice treated with lipopolysaccharide, and in humans with chronic obstructive pulmonary disease (Weathington et al., "A Novel Peptide CVCR Ligand Derived from Extracellular Matrix Degradation During Airway Inflammation," *Nat. Med.* 12:317-323 (2006), which is hereby incorporated by reference in its entirety). These collagen fragments can bind to CXC receptors and promote the recruitment of inflammatory cells into the lung (Weathington et al., "A Novel Peptide CVCR Ligand Derived from Extracellular Matrix Degradation During Airway Inflammation," *Nat. Med.* 12:317-323 (2006), which is hereby incorporated by reference in its entirety). Hence, whether fibronectin or collagen degradation products accumulate in the lungs following treatment with pUR4 will be determined. Protein extracts will be analyzed by Western blotting using polyclonal antibodies that recognize different epitopes within the fibronectin molecule, or that recognize cleaved collagen I. The presence of fibronectin and collagen fragments in bronchoaveolar lavage (BAL) fluid will also be assessed. These ECM fragments could contribute to altered cell proliferation, migration, and matrix synthesis and deposition that occur during fibrosis. If such fragments accumulate, then future studies will be directed towards characterizing these fragments, and determining if they play an important role in regulating the fibrotic response.

Example 16 pUR4 Blocks Fibrosis and Inflammation Following Liver Injury

One of the hallmarks of liver fibrosis is the excess deposition of ECM proteins, including collagen and fibronectin. Given the ability of peptide pUR4 to inhibit fibronectin and collagen deposition in vascular remodeling, the effect of pUR4 in limiting the development or progression of liver fibrosis was investigated.

Liver fibrosis was induced in mice by administration of dimethylnitrosamine (DMN) for 4 weeks as previously described (Yoshida et al., "SOCS1 is a Suppressor of Liver Fibrosis and Hepatitis-Induced Carcinogenesis," *J. Exp. Med.* 199:1701-1707 (2004)). This is a well established model of liver fibrosis and some of the key pathological features that develop in DMN induced fibrosis are similar to those seen in humans with liver fibrosis (Wu et al., "Animal Models of Liver Fibrosis," *Scand. J. Gastroenterol.* 31:1137-1143 (1996); Jenkins et al., "A Dimethylnitrosamine-Induced Model of Cirrhosis and Portal Hypertension in the Rat," *J. Hepatol.* 1:489-499 (1985), which are hereby incorporated by reference in their entirety). pUR4 was either administered for the last 10 days of DMN treatment (simultaneous treatment regimen), or for 14 days following cessation of DMN treatment (sequential treatment regimen). The latter model was performed to determine whether the peptide is effective when administered after fibrosis is established.

Figures 17A, 17B, 17C:
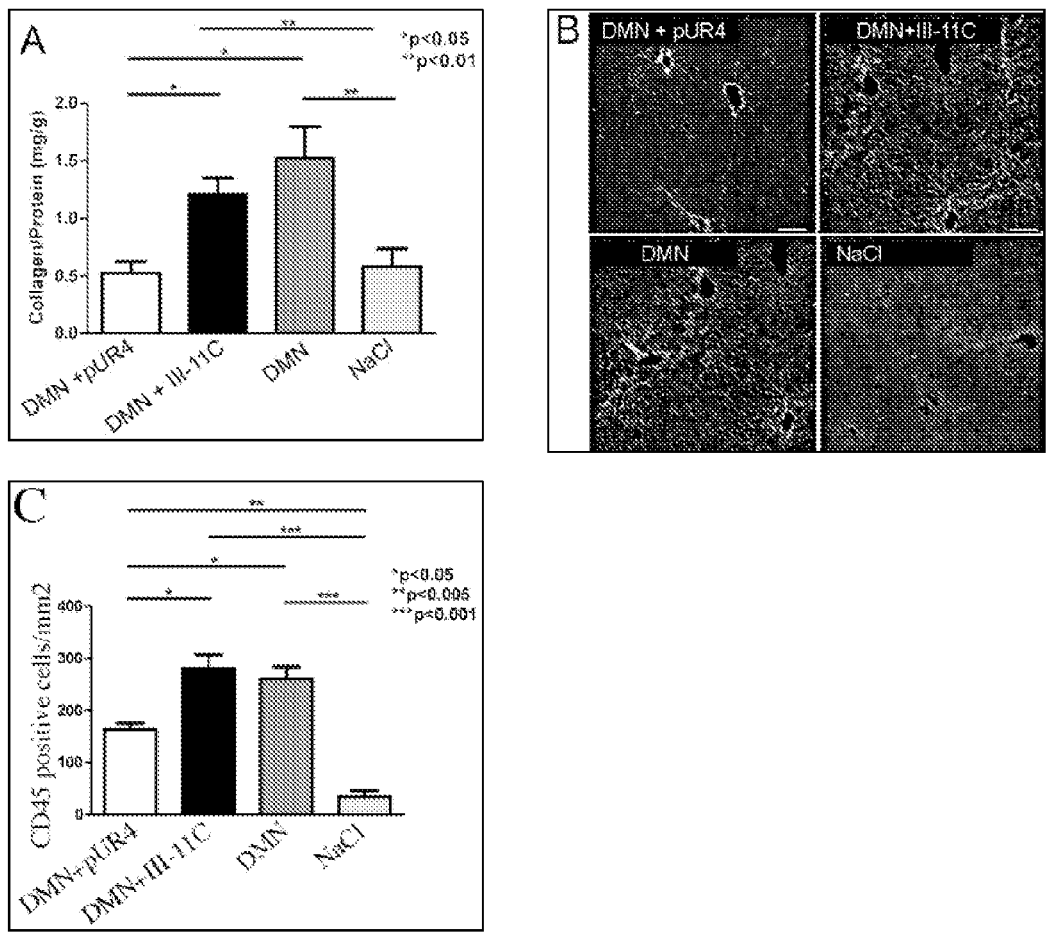
FIGS. 17A-17C show that pUR4 decreases fibronectin and collagen I deposition and inflammatory cell infiltration in a liver fibrosis model. Collagen content in the liver of mice was measured by quantitating hydroxyproline levels (FIG. 17A). Treatment groups were DMN treated mice that were post treated with pUR4 or control III-11C peptide, DMN without peptide, and saline treated control mice. Fibronectin content in the liver of mice was assessed by immunohistochemistry of liver sections using a fibronectin antibody (FIG. 17B). Inflammatory cell infiltration into the liver was assessed by quantitating the CD45 positive cells per unit area (FIG. 17C). Sequential model (FIGS. 17A, 17B); Simultaneous model (FIG. 17C). n=3 in each group.

In the sequential treatment model, the pUR4 peptide reduced fibronectin (FIG. 17B) and collagen I (FIG. 17A) content in the liver. Similar results were found with the simultaneous treatment regimen. pUR4 significantly reduced the infiltration of immune cells into the liver in the simultaneous treatment regimen (FIG. 17C). There was a trend towards reduced inflammation in the sequential treatment model.

Importantly, these experiments show that animals treated with pUR4 in the absence of injury for up to 2 weeks do not show any adverse effects, or any decrease in the normal levels of ECM fibronectin or collagen I, indicating that the peptide preferentially affects newly deposited ECM proteins.

Example 17

Determine pUR4 Inhibition Development and Progression of Liver Fibrosis

Dimethylnitrosamine (DMN) will be used to induce liver injury and fibrosis in mice (10 mg/kg body weight, 3×/week for 4 weeks) as described in Example 16. The experimental groups will include: 1) DMN alone; 2) DMN+pUR4 peptide; and 3) DMN+control peptide. Non DMN-treated control animals will receive i.p. injections of 0.9% saline plus: 4) pUR4; or 5) the control peptide. Two treatment strategies will be used, as described in Example 16. In the simultaneous treatment strategy, peptides will be administered daily during the last 10 days of DMN treatment. This will allow assessment of pUR4 on preventing fibrosis development. In the sequential treatment strategy, DMN will be injected for 4 weeks. Peptides will then be administered daily for 14 days in the absence of DMN. This will allow assessment of pUR4 on preventing fibrosis progression.

Fibrosis progresses in the DMN model after cessation of DMN treatment (Madden et al., "Dimethylnitrosamine-Induced Hepatic Cirrhosis: A New Canine Model of an Ancient Human Disease," *Surgery* 68:260-267 (1970)). As demonstrated in Example 16, pUR4 administration resulted in a significant decrease in the amount of accumulating collagen suggesting fibrosis regression in the sequential strategy (FIG. 17A). The same dose of pUR4 (20 mg/kg/d) that has proven to be effective in pilot studies (FIGS. 17A-17C) will be used here. To determine the effects of pUR4 on fibrosis, mice will be sacrificed 28 (simultaneous model) or 42 days (sequential model) after the start of DMN treatment. To establish the level of fibrosis present at the time of pUR4 administration, some mice will also be sacrificed at 18 (simultaneous model) or 28 days (sequential model), just prior to pUR4 administration. The liver will be removed, sectioned, and processed for immunohistochemistry (IHC). The levels of individual matrix components will be assessed by IHC using antibodies to collagen I, collagen III, and fibronectin, as described supra (Example 3). Protein levels of fibronectin will be quantitated by sandwich ELISA, and collagens I and III will be quantitated by western blot analysis of tissue extracts. Total collagen content will be determined by measuring the hydroxyproline content of liver extracts (Stegemann, H., "Microdetermination of Hydroxyproline with Chloramine-T and p-Dimethlamino-Benzaldehyde," *Hoppe-seylers Z. Physiol. Chem.* 311:41-45 (1958), which is hereby incorporated by reference in its entirety). The persistence of the peptides in the liver will be determined essentially as described supra (Example 2); see also Bentmann et al., "Circulating Fibronectin Affects Bone Matrix, Whereas Osteoblast Fibronectin Modulates Osteoblast Function," *J. Bone Miner. Res.* 25:706-715 (2010), which is hereby incorporated by reference in its entirety). Liver function will be assessed by measuring the levels of albumin, since others have shown that there are reduced levels of circulating albumin following DMN treatment (Saha et al., "Study of Plasma Protein C and Inflammatory Pathways: Biomarkers for Dimethylnitrosamine-Induced Liver Fibrosis in Rats," *Eur. J. Pharmacol.* 575:158-167 (2007), which is hereby incorporated by reference in its entirety).

Example 18

Determine pUR4 Affect on Myofibroblast Accumulation in Liver Fibrosis

Activation of hepatic stellate cells (HSC) is an event that contributes to the development and persistence of fibrosis (Friedman, S. L., "Hepatic Stellate Cells: Protean, Multifunctional, and Enigmatic Cells of the Liver," *Physiol. Rev.* 88:125-172 (2008), which is hereby incorporated by reference in its entirety). Therefore, IHC analysis of tissue sections will be employed to determine whether pUR4 affects activated hepatic stellate cell number. Sections will be stained with antibodies to smooth muscle a-actin to identify activated hepatic stellate cells. DAPI will be used to identify cell nuclei. The number of positive cells will be counted per unit area and expressed as percent positive cells per cross sectional area. Whether pUR4 affects cell proliferation will be assessed by staining tissue sections with PCNA. Sections will be co-stained with antibodies to smooth muscle α-actin or CD45 (leukocyte common antigen) to distinguish between HSC and immune cells. Quantitation will be performed as described supra. It is expected that pUR4 administration will prevent the accumulation of HSC associated with the progression of liver fibrosis.

Example 19

Determine pUR4 Affect on Inflammatory Response in Liver Fibrosis

DMN induces an inflammatory response, which contributes to the development of fibrosis (Saha et al., "Study of Plasma Protein C and Inflammatory Pathways: Biomarkers for Dimethylnitrosamine-Induced Liver Fibrosis in Rats," *Eur. J. Pharmacol.* 575:158-167 (2007), which is hereby incorporated by reference in its entirety). Therefore, inflammatory cells present in the liver will be characterized and quantitated by IHC using antibodies to CD45 as shown in FIG. 17B. Luminex technology will be used to determine whether the levels of a panel of cytokines change in liver extracts from DMN treated versus control animals that were treated with pUR4 or control peptides. Any changes found by IHC and Western blotting will be verified. Whether changes occur at the RNA level by qRT PCR will also be assessed. Inflammatory mediators/cytokines that are known to play an important role in regulating liver fibrosis that will be assessed include: TGFβ, PDGF, TNFα, and MCP-1 (Friedman, S. L., "Hepatic Stellate Cells: Protean, Multifunctional, and Enigmatic Cells of the Liver," *Physiol. Rev.* 88:125-172 (2008), which is hereby incorporated by reference in its entirety). Samples will be analyzed just prior to peptide administration and at the time of euthanasia. It is expected that pUR4 treatment will attenuate the inflammatory events associated with the progression of liver fibrosis.

Example 20

Determine Whether pUR4 Administration Leads to the Production and Accumulation of Fibronectin and Collagen Fragments in Fibrotic Liver Tissue Whether fibronectin or collagen degradation products accumulate in the liver during fibrosis will be determined, and whether the levels of fibronectin fragments change following treatment with pUR4 will also be determined. Liver extracts will be analyzed by Western blotting using polyclonal antibodies that recognize different epitopes within the fibronectin molecule, or that recognize cleaved collagen I (Billinghurst et al., "Immunoassay for Collagenase-Mediated Cleavage of Types I and II Collagens," *Methods Mol. Biol.* 151:457-472 (2001), which is hereby incorporated by reference in its entirety). If it is found that such fragments accumulate, then these fragments will be characterize and their role in promoting activities that are upregulated during fibrosis, including cell migration, proliferation, and inflammation will be determined.

Example 21

Determine Whether pUR4 Treatment Alters the Levels of Proteins in Liver Tissue that Modulate Fibronectin and Collagen I Turnover Upregulation of tissue inhibitor of metalloproteinases (TIMPs) are important for the establishment of fibrosis (Hemmann et al., "Expression of MMPs and TIMPs in Liver Fibrosis—a Systematic Review with Special Emphasis on Anti-Fibrotic Strategies," *J. Hepatol.* 46:955-975 (2007), which is hereby incorporated by reference in its entirety). Further, the presence of mutant collagen I that cannot be degraded by MMPs results in persistent activation of hepatic stellate cells, and reduced recovery from CCl4 induced liver fibrosis (Issa et al., "Mutation in Collagen-1 that Confers Resistance to the Action of Collagenase Results in Failure of Recovery from CCl4-Induced Liver Fibrosis, Persistence of Activated Hepatic Stellate Cells, and Diminished Hepatocyte Regeneration," *FASEB J.* 17:47-49 (2003), which is hereby incorporated by reference in its entirety). Hence, whether pUR4 treatment alters the levels of TIMP-1, TIMP-2, MMP13, MMP 2, MMP8, MMP9, MMP3 and MT1-MMP in the liver will be analyzed by qRT PCR and ELISA or western blotting. These MMPs have been shown to be upregulated during liver fibrosis and/or to be involved in the development or resolution of fibrosis (Hemmann et al., "Expression of MMPs and TIMPs in Liver Fibrosis—a Systematic Review with Special Emphasis on Anti-Fibrotic Strategies," *J. Hepatol.* 46:955-975 (2007), which is hereby incorporated by reference in its entirety). Because of data showing that Endo180 and β1 integrin regulate matrix turnover, and because both are found in stellate cells (Friedman, S. L., "Hepatic Stellate Cells: Protean, Multifunctional, and Enigmatic Cells of the Liver," *Physiol. Rev.* 88:125-172 (2008); Mousavi et al., "Up-Regulation of uPARAP/Endo180 During Culture Activation of Rat Hepatic Stellate Cells and its Presence in Hepatic Stellate Cell Lines from Different Species," *BMC Cell Biol.* 10:39 (2009), which are hereby incorporated by reference in their entirety) how these two molecules are modified by treatment with pUR4 will also be examined by qRT PCR and Western blotting.

Although the invention has been described in detail for the purpose of illustration, it is understood that such detail is solely for that purpose, and variations can be made therein by those skilled in the art without departing from the spirit and scope of the invention which is defined in the following claims.

What is claimed:
1. A method of improving heart function in a subject having an ischemic cardiac injury, said method comprising:
   administering to the subject a peptide derived from a fibronectin binding bacterial adhesin protein, wherein the peptide binds fibronectin and inhibits deposition of fibronectin into the cardiac extracellular matrix to improve heart function in the subject.
2. The method according to claim 1, wherein the peptide blocks fibronectin polymerization.
3. The method according to claim 1, wherein the peptide blocks fibronectin-collagen binding.
4. A method of improving heart function in a subject having an ischemic cardiac injury, said method comprising:
   administering to the subject a peptide derived from a fibronectin binding bacterial adhesin protein, wherein the peptide is selected from the group consisting of $pUR_4$, $FNZ_{r2}$, and $FNBPA_{9-10}$, and wherein the peptide binds fibronectin and inhibits deposition of fibronectin into the cardiac extracellular matrix to improve heart function in the subject.
5. The method according to claim 1, wherein the subject has suffered or is suffering from a cardiac infarction and/or heart failure.
6. The method according to claim 4, wherein the subject has suffered or is suffering from a cardiac infarction and/or heart failure.
7. The method according to claim 4, wherein the peptide is $pUR_4$.
8. A method of improving heart function in a subject having an ischemic cardiac injury, said method comprising:
   administering to the subject a peptide comprising at least about 85 percent sequence identity to SEQ ID NO: 1, SEQ ID NO: 2, or SEQ ID NO: 3, wherein the peptide binds fibronectin and inhibits deposition of fibronectin into the cardiac extracellular matrix to improve heart function in the subject.
9. The method according to claim 8, wherein the subject has suffered or is suffering from a cardiac infarction and/or heart failure.
10. The method according to claim 8, wherein the peptide comprises at least about 90 percent sequence identity to SEQ ID NO: 1, SEQ ID NO: 2, or SEQ ID NO: 3.
11. The method according to claim 8, wherein the peptide comprises at least about 95 percent sequence identity to SEQ ID NO: 1, SEQ ID NO: 2, or SEQ ID NO: 3.
12. The method according to claim 8, wherein the peptide is selected from the group consisting of the amino acids 6-101 of SEQ ID NO:2 or the amino acids 6-81 of SEQ ID NO:3.
13. A method of improving heart function in a subject having an ischemic cardiac injury, said method comprising:
   administering to the subject a peptide consisting of the amino acid residues 13-61 of SEQ ID NO: 1, wherein the peptide binds fibronectin and inhibits deposition of fibronectin into the cardiac extracellular matrix to improve heart function in the subject.

* * * * *

SEQUENCE LISTING

<160> NUMBER OF SEQ ID NOS: 5

<210> SEQ ID NO 1
<211> LENGTH: 64
<212> TYPE: PRT
<213> ORGANISM: artificial
<220> FEATURE:
<223> OTHER INFORMATION: Bacterial adhesin derived peptide pUR4

<400> SEQUENCE: 1

Met Arg Gly Ser His His His His His His Gly Ser Lys Asp Gln Ser
1               5                   10                  15

Pro Leu Ala Gly Glu Ser Gly Glu Thr Glu Tyr Ile Thr Glu Val Tyr
            20                  25                  30

Gly Asn Gln Gln Asn Pro Val Asp Ile Asp Lys Lys Leu Pro Asn Glu
        35                  40                  45

Thr Gly Phe Ser Gly Asn Met Val Glu Thr Glu Asp Thr Lys Leu Asn
    50                  55                  60

<210> SEQ ID NO 2
<211> LENGTH: 101
<212> TYPE: PRT
<213> ORGANISM: artificial
<220> FEATURE:
<223> OTHER INFORMATION: Bacterial adhesin dervice peptide FNZr2

<400> SEQUENCE: 2

Gly Pro Leu Gly Ser Arg Asn Pro His Leu Met Gly Ile Gly Gly Gly
1               5                   10                  15

Leu Ala Gly Glu Ser Gly Glu Thr Thr Pro Lys Pro Gly Gln Thr Gly
            20                  25                  30

Gly Gln Gly Pro Val Ile Glu Thr Thr Glu Asp Thr Gln Lys Gly Met
        35                  40                  45

Ser Gly Gln Ser Gly Gly Thr Ile Glu Ser Glu Asn Thr Lys Lys Pro
    50                  55                  60

Glu Val Met Ile Gly Gly Gln Gly Gln Thr Ile Glu Thr Thr Glu Asp
65                  70                  75                  80

Thr Gln Lys Gly Met Ser Gly Gln Ser Gly Gly Thr Ile Glu Ser Glu
                85                  90                  95

Asp Thr Lys Lys Pro
            100

<210> SEQ ID NO 3
<211> LENGTH: 81
<212> TYPE: PRT
<213> ORGANISM: artificial
<220> FEATURE:
<223> OTHER INFORMATION: Bacterial adhesin derived peptide FNBPA9-10

<400> SEQUENCE: 3

Gly Pro Leu Gly Ser Lys Tyr Glu Gln Gly Gly Asn Ile Val Asp Ile
1               5                   10                  15

Asp Phe Asp Ser Val Pro Gln Ile His Gly Gln Asn Lys Gly Asn Gln
            20                  25                  30

Ser Phe Glu Glu Asp Thr Glu Lys Asp Lys Pro Lys Tyr Glu His Gly
        35                  40                  45

Gly Asn Ile Ile Asp Ile Asp Phe Asp Ser Val Pro His Ile His Gly
    50                  55                  60

Phe Asn Lys His Thr Glu Ile Ile Glu Glu Asp Thr Asn Lys Asp Lys
65                  70                  75                  80

Pro

```
<210> SEQ ID NO 4
<211> LENGTH: 68
<212> TYPE: PRT
<213> ORGANISM: artificial
<220> FEATURE:
<223> OTHER INFORMATION: Bacterial adhesin derived peptide R1R2

<400> SEQUENCE: 4
```

His His His His His His Gly Ser Gly Leu Asn Gly Glu Asn Gln Lys
1               5                   10                  15

Glu Pro Glu Gln Gly Glu Arg Gly Glu Ala Gly Pro Pro Leu Ser Gly
            20                  25                  30

Leu Ser Gly Asn Asn Gln Gly Arg Pro Ser Leu Pro Gly Leu Asn Gly
        35                  40                  45

Glu Asn Gln Lys Glu Pro Glu Gln Gly Glu Arg Gly Glu Ala Gly Pro
    50                  55                  60

Pro Lys Ser Asn
65

```
<210> SEQ ID NO 5
<211> LENGTH: 576
<212> TYPE: PRT
<213> ORGANISM: artificial
<220> FEATURE:
<223> OTHER INFORMATION: Fibronectin peptide

<400> SEQUENCE: 5
```

Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Asn Val Leu Val Cys Thr Cys Tyr
        35                  40                  45

Gly Gly Ser Arg Gly Phe Asn Cys Glu Ser Lys Pro Glu Ala Glu Glu
    50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
            85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
    130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
            165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
    210                 215                 220

```
Leu Gln Cys Ile Cys Thr Gly Asn Gly Arg Gly Glu Trp Lys Cys Glu
225                 230                 235                 240

Arg His Thr Ser Val Gln Thr Ser Ser Gly Ser Gly Pro Phe Thr
            245                 250                 255

Asp Val Arg Ala Ala Val Tyr Gln Pro Gln Pro His Pro Gln Pro Pro
            260                 265                 270

Pro Tyr Gly His Cys Val Thr Asp Ser Gly Val Val Tyr Ser Val Gly
            275                 280                 285

Met Gln Trp Leu Lys Thr Gln Gly Asn Lys Gln Met Leu Cys Thr Cys
290                 295                 300

Leu Gly Asn Gly Val Ser Cys Gln Glu Thr Ala Val Thr Gln Thr Tyr
305                 310                 315                 320

Gly Gly Asn Leu Asn Gly Glu Pro Cys Val Leu Pro Phe Thr Tyr Asn
            325                 330                 335

Gly Arg Thr Phe Tyr Ser Cys Thr Thr Glu Gly Arg Gln Asp Gly His
            340                 345                 350

Leu Trp Cys Ser Thr Thr Ser Asn Tyr Glu Gln Asp Gln Lys Tyr Ser
            355                 360                 365

Phe Cys Thr Asp His Thr Val Leu Val Gln Thr Gln Gly Gly Asn Ser
            370                 375                 380

Asn Gly Ala Leu Cys His Phe Pro Phe Leu Tyr Asn Asn His Asn Tyr
385                 390                 395                 400

Thr Asp Cys Thr Ser Glu Gly Arg Arg Asp Asn Met Lys Trp Cys Gly
            405                 410                 415

Thr Thr Gln Asn Tyr Asp Ala Asp Gln Lys Phe Gly Phe Cys Pro Met
            420                 425                 430

Ala Ala His Glu Glu Ile Cys Thr Thr Asn Glu Gly Val Met Tyr Arg
            435                 440                 445

Ile Gly Asp Gln Trp Asp Lys Gln His Asp Met Gly His Met Met Arg
            450                 455                 460

Cys Thr Cys Val Gly Asn Gly Arg Gly Glu Trp Thr Cys Ile Ala Tyr
465                 470                 475                 480

Ser Gln Leu Arg Asp Gln Cys Ile Val Asp Asp Ile Thr Tyr Asn Val
            485                 490                 495

Asn Asp Thr Phe His Lys Arg His Glu Glu Gly His Met Leu Asn Cys
            500                 505                 510

Thr Cys Phe Gly Gln Gly Arg Gly Arg Trp Lys Cys Asp Pro Val Asp
            515                 520                 525

Gln Cys Gln Asp Ser Glu Thr Gly Thr Phe Tyr Gln Ile Gly Asp Ser
            530                 535                 540

Trp Glu Lys Tyr Val His Gly Val Arg Tyr Gln Cys Tyr Cys Tyr Gly
545                 550                 555                 560

Arg Gly Ile Gly Glu Trp His Cys Gln Pro Leu Gln Thr Tyr Pro Ser
            565                 570                 575
```